(12) United States Patent
Dowling et al.

(10) Patent No.: US 9,611,248 B2
(45) Date of Patent: Apr. 4, 2017

(54) CHEMICAL COMPOUNDS

(71) Applicants: Syngenta Participations AG, Basel (CH); Syngenta Limited, Guildford, Surrey (CH)

(72) Inventors: Alan John Dowling, Bracknell (GB); John Martin Clough, Bracknell (GB); Jutta Martin Boehmer, Bracknell (GB); Mangala Phadte, Ilhas (IN); Ravindra Sonawane, Ilhas (IN); Adrian Longstaff, Bracknell (GB); James Alan Morris, Bracknell (GB); Timothy Robert Desson, Bracknell (GB); Matthew Brian Hotson, Bracknell (GB); Sally Russell, Bracknell (GB); Kenneth Ling, Bracknell (GB); Susan Patricia Barnett, Bracknell (GB); David Philip Bacon, Bracknell (GB); Donn Warwick Moseley, Bracknell (GB); William Roderick Mound, Bracknell (GB)

(73) Assignees: Syngenta Limited, Guildford, Surrey (GB); Syngenta Participations AG, Basel (CH)

( * ) Notice: Subject to any disclaimer, the term of this patent is extended or adjusted under 35 U.S.C. 154(b) by 0 days.

(21) Appl. No.: 14/906,138

(22) PCT Filed: Aug. 5, 2013

(86) PCT No.: PCT/EP2013/066393
§ 371 (c)(1),
(2) Date: Jan. 19, 2016

(87) PCT Pub. No.: WO2015/018432
PCT Pub. Date: Feb. 12, 2015

(65) Prior Publication Data
US 2016/0159767 A1    Jun. 9, 2016

(51) Int. Cl.
| | | |
|---|---|---|
| *C07D 401/04* | (2006.01) | |
| *A01N 43/40* | (2006.01) | |
| *C07D 403/04* | (2006.01) | |
| *C07D 403/14* | (2006.01) | |
| *C07D 407/14* | (2006.01) | |
| *C07D 409/14* | (2006.01) | |
| *A01N 43/42* | (2006.01) | |
| *A01N 43/54* | (2006.01) | |
| *A01N 43/58* | (2006.01) | |
| *A01N 43/84* | (2006.01) | |
| *A01N 55/00* | (2006.01) | |
| *C07D 405/14* | (2006.01) | |
| *C07F 7/08* | (2006.01) | |

(52) U.S. Cl.
CPC .......... *C07D 401/04* (2013.01); *A01N 43/40* (2013.01); *A01N 43/42* (2013.01); *A01N 43/54* (2013.01); *A01N 43/58* (2013.01); *A01N 43/84* (2013.01); *A01N 55/00* (2013.01); *C07D 403/04* (2013.01); *C07D 403/14* (2013.01); *C07D 405/14* (2013.01); *C07D 407/14* (2013.01); *C07D 409/14* (2013.01); *C07F 7/0812* (2013.01)

(58) Field of Classification Search
CPC ........ A01N 43/40; A01N 43/42; A01N 43/54; A01N 43/58; A01N 43/84; A01N 55/00; C07D 401/04; C07D 403/04; C07D 403/14; C07D 405/14; C07D 407/14; C07D 409/14; C07F 7/0812
USPC .......................................................... 504/103
See application file for complete search history.

(56) References Cited

FOREIGN PATENT DOCUMENTS

CH          633678 A5  * 12/1982  ............. A01N 43/36

OTHER PUBLICATIONS

International Search Report for International Application PCT/EP2013/066393 mailed Sep. 16, 2013.

* cited by examiner

*Primary Examiner* — Janet Epps-Smith
*Assistant Examiner* — Courtney Brown
(74) *Attorney, Agent, or Firm* — James Cueva

(57) ABSTRACT

The invention relates to pyrrolone compounds of the formula (I)

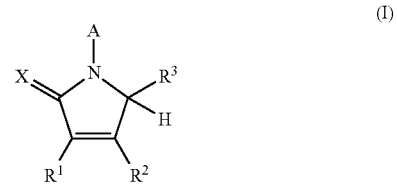

wherein X, $R^1$, $R^2$, $R^3$ and A are as defined in the specification. Furthermore, the present invention relates to processes and intermediates for making compounds of formula (I), to herbicidal compositions comprising these compounds and to methods of using these compounds to control plant growth.

14 Claims, No Drawings

CHEMICAL COMPOUNDS

RELATED APPLICATION INFORMATION

This application is a 371 national stage entry of International Application No. PCT/EP2013/066393, filed 5 Aug. 2013.

The present invention relates to certain substituted pyrrolone derivatives, to processes for their preparation, herbicidal compositions comprising them, and their use in controlling plants or inhibiting plant growth.

Herbicidal pyrrolones of the formula

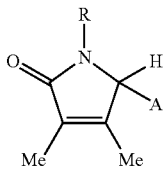

wherein A is hydroxy, halogen or OAcyl; and R is an optionally substituted aryl, aralkyl or heteroaryl group are taught in Swiss patent application CH633678.

A problem that remains is the provision of alternative herbicidal pyrrolones.

A further problem that remains is the provision of herbicidal compounds having improved potency relative to known compounds.

A further problem that remains is the provision of herbicidal compounds having an improved spectrum of activity relative to known compounds.

A further problem that remains is the provision of herbicidal compounds having enhanced selectivity relative to known compounds.

These and other problems of the art are addressed by the present invention.

SUMMARY OF THE INVENTION

In a first aspect, the invention provides compounds of the formula (I)

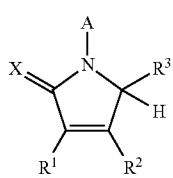

wherein
X is selected from S and O;
A is selected from

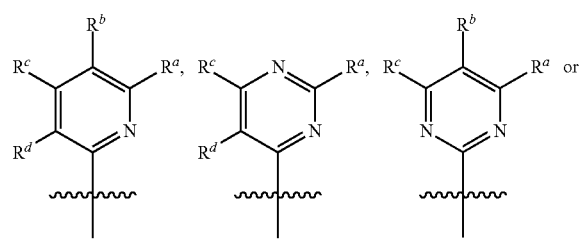

-continued

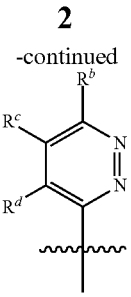

$R^a$ is selected from hydrogen and halogen.

$R^b$ is selected from hydrogen, formyl, hydroxyl, halogen, nitro, cyano, $C_1$-$C_6$ alkyl, $C_1$-$C_6$ cyanoalkyl, $C_3$-$C_6$ cycloalkyl, $C_3$-$C_6$ cyanocycloalkyl, $C_1$-$C_6$ haloalkyl, $C_1$-$C_6$ alkylthio, $C_1$-$C_6$ alkoxy, $C_1$-$C_6$ alkoxy $C_1$-$C_6$ alkyl, $C_1$-$C_6$ alkoxy $C_1$-$C_6$ alkoxy, $C_1$-$C_6$ alkylthio $C_1$-$C_6$ alkyl, aryl $C_1$-$C_6$ alkylthio, $C_3$-$C_6$ cycloalkoxy, aryl $C_1$-$C_6$ alkoxy, aryl $C_1$-$C_6$ alkoxy $C_1$-$C_6$ alkoxy, $C_1$-$C_6$ cyanoalkoxy, $C_1$-$C_6$ haloalkoxy, $C_2$-$C_6$ alkenyl, $C_2$-$C_6$ alkynyl, $C_2$-$C_6$ cyanoalkenyl, $C_2$-$C_6$ cyanoalkynyl, $C_2$-$C_6$ alkenyloxy, $C_2$-$C_6$ alkynyloxy, $C_2$-$C_6$ haloalkenyl, $C_2$-$C_6$ haloalkynyl, $C_2$-$C_6$ haloalkenyloxy, $C_2$-$C_6$ haloalkynyloxy, $C_1$-$C_6$ alkoxy $C_2$-$C_6$ alkenyl, $C_1$-$C_6$ alkoxy $C_2$-$C_6$ alkynyl, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, $C_1$-$C_6$ alkylsulfonyloxy, $C_1$-$C_6$ alkylcarbonyl, $C_1$-$C_6$ haloalkylcarbonyl, a group $R^{10}O(O)C$—, $C_2$-$C_6$ alkenylcarbonyl, $C_2$-$C_6$ alkynylcarbonyl, $C_2$-$C_6$ haloalkenylcarbonyl, $C_2$-$C_6$ haloalkynylcarbonyl, $C_1$-$C_6$ alkoxycarbonyloxy, $C_1$-$C_6$ alkenyloxycarbonyloxy, $C_1$-$C_6$ alkynyloxycarbonyloxy, $C_1$-$C_6$ haloalkoxycarbonyloxy, tri $C_1$-$C_6$ alkylsilyl $C_2$-$C_6$ alkynyl, a group $R^5R^6N$—, a group $R^5C(O)N(R^6)$—, a group $R^5S(O_2)N(R^6)$—, a group $R^5R^6NC(O)$—, a group $R^5R^6NC(O)O$—, a group $R^6R^6NSO_2$—, a $C_6$-$C_{10}$ aryl group optionally substituted by from 1 to 3 groups independently selected from halogen, nitro, cyano, $C_1$-$C_3$ alkyl, $C_1$-$C_3$ alkoxy, $C_1$-$C_3$ haloalkyl, $C_1$-$C_3$ haloalkoxy and $C_1$-$C_6$ alkyl $S(O_2)$— or any two groups on adjacent carbon atoms together with the carbon atoms to which they are attached form a 3-6 membered saturated or partially unsaturated ring optionally comprising from 1 to 3 heteroatoms independently selected from S, O and N; a $C_5$-$C_{10}$ heteroaryl group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy; a $C_6$-$C_{10}$ aryloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy; a $C_6$-$C_{10}$ benzyl group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy; a $C_6$-$C_{10}$ benzyloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy; a $C_3$-$C_6$ heterocyclyl group optionally substituted by from 1 to 3 groups independently selected from $C_1$-$C_4$ alkyl; a $C_5$-$C_{10}$ heteroaryl $C_1$-$C_6$ alkoxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy; a heterocyclyl $C_1$-$C_6$ alkoxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy; and a $C_3$-$C_6$ cycloalkyl ring optionally comprising from 1 to 3 heteroatoms independently selected from S, O and N and optionally substituted with from 1 to 3 groups independently selected from halogen or $C_1$-$C_6$ alkyl; or $R^b$ and $R^c$ together with the carbon atoms to which they are attached form a 3-6 membered saturated or partially unsaturated ring optionally comprising from 1 to 3 heteroatoms independently selected from S, O and N and optionally substituted with from 1 to 3 groups independently selected from halogen or $C_1$-$C_6$ alkyl;

$R^c$ is selected from hydrogen, formyl, halogen, cyano, $C_1$-$C_6$ alkyl, $C_1$-$C_6$ cyanoalkyl, $C_3$-$C_6$ cycloalkyl, $C_3$-$C_6$ cyanocycloalkyl, $C_1$-$C_6$ haloalkyl, $C_1$-$C_6$ alkoxy, $C_1$-$C_6$ cyanoalkoxy, $C_1$-$C_6$ haloalkoxy, $C_2$-$C_6$ alkenyl, $C_2$-$C_6$ alkynyl, $C_2$-$C_6$ cyanoalkenyl, $C_2$-$C_6$ cyanoalkynyl, $C_2$-$C_6$ alkenyloxy, $C_1$-$C_6$ alkoxy $C_1$-$C_6$ alkyl, $C_2$-$C_6$ alkynyloxy, $C_2$-$C_6$ haloalkenyl, $C_2$-$C_6$ haloalkynyl, $C_2$-$C_6$ haloalkenyloxy, $C_1$-$C_6$ alkthio $C_1$-$C_6$ alkyl, $C_2$-$C_6$ haloalkynyloxy, $C_1$-$C_6$ alkylthio, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, $C_1$-$C_6$ alkylcarbonyl, $C_1$-$C_6$ haloalkylcarbonyl, a group $R^5R^6N-$ and, when $R^b$ is other than hydrogen or methyl, nitro; or $R^b$ and $R^c$ together with the carbon atoms to which they are attached form a 3-6 membered saturated or partially unsaturated ring optionally comprising from 1 to 3 heteroatoms independently selected from S, O and N and optionally substituted with from 1 to 3 groups independently selected from halogen or $C_1$-$C_6$ alkyl;

$R^d$ is selected from hydrogen, cyano and halogen;

$R^1$ is $C_1$-$C_6$ alkyl or $C_1$-$C_3$ alkoxy;

$R^2$ is chlorine or bromine, $C_2$-$C_6$ alkenyloxy, $C_1$-$C_6$ haloalkoxy or $C_1$-$C_3$ alkoxy;

with the proviso that $R^1$ and $R^2$ are not both $C_1$-$C_3$ alkoxy;

$R^3$ is selected from halogen, hydroxyl, or any one of the following groups

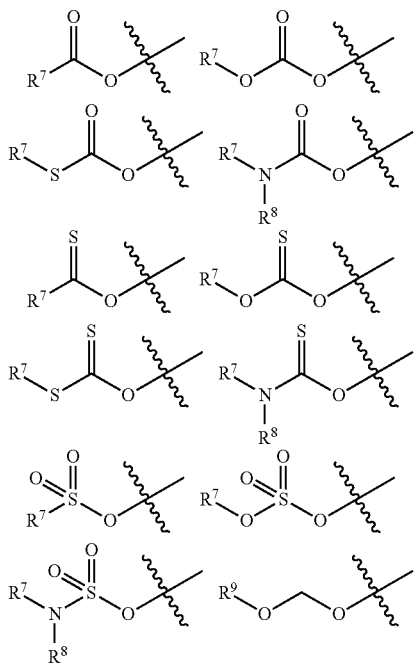

$R^5$ and $R^6$ are independently selected from hydrogen, $C_1$-$C_6$ alkyl, $C_1$-$C_6$ haloalkyl, $C_2$-$C_6$ alkenyl, $C_2$-$C_6$ alkynyl, aryl $C_1$-$C_6$ alkyl, or $R^5$ and $R^6$ together with the carbon atoms to which they are attached form a 3-6 membered saturated or partially unsaturated ring optionally comprising from 1 to 3 heteroatoms independently selected from S, O and N and optionally substituted with from 1 to 3 groups independently selected from halogen or $C_1$-$C_6$ alkyl;

$R^7$ and $R^8$ are independently selected from hydrogen, $C_1$-$C_6$ alkyl, $C_1$-$C_6$ haloalkyl, $C_2$-$C_6$ alkenyl, $C_2$-$C_6$ alkynyl; 5 to 10 membered heteroaryl which can be mono- or bicyclic comprising from 1 to 4 heteroatoms independently selected from N, O and S, optionally substituted with 1 to 3 groups independently selected from halogen, $C_1$-$C_3$ alkyl, $C_1$-$C_3$ haloalkyl and $C_1$-$C_3$ alkoxy; $C_6$-$C_{10}$ aryl optionally substituted with 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy; or $R^7$ and $R^8$ together with the carbon atoms to which they are attached form a 3-6 membered saturated or partially unsaturated ring optionally comprising from 1 to 3 heteroatoms independently selected from S, O and N and optionally substituted with from 1 to 3 groups independently selected from halogen or $C_1$-$C_6$ alkyl;

$R^9$ is selected from $C_1$-$C_6$ alkyl or benzyl optionally substituted with 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy;

$R^{10}$ is selected from hydrogen, $C_1$-$C_6$ alkyl, $C_1$-$C_6$ haloalkyl, $C_2$-$C_6$ alkenyl and $C_2$-$C_6$ alkynyl;

with the provisos that (i) if $R^b$ is methylthio, methoxy, methoxycarbonyl, fluorine or trifluoromethyl and $R^2$ is chlorine or bromine, $R^c$ cannot be hydrogen and (ii) if $R^b$ is tri $C_1$-$C_6$ alkylsilyl $C_2$-$C_6$ alkynyl, $R^2$ cannot be chlorine or bromine;

or an N-oxide or salt form thereof.

In a second aspect, the invention provides herbicidal compositions comprising a compound of the invention together with at least one agriculturally acceptable adjuvant or diluent.

In a third aspect, the invention provides the use of a compound or a composition of the invention for use as a herbicide.

In a fourth aspect, the invention provides a method of controlling weeds in crops of useful plants, comprising applying to said weeds or to the locus of said weeds, or to said useful crop plants, a compound or a composition of the invention.

In a fifth aspect, the invention relates to processes useful in the preparation of compounds of the invention.

In a sixth aspect, the invention relates to intermediates useful in the preparation of compounds of the invention.

DETAILED DESCRIPTION

In particularly preferred embodiments of the invention, the preferred groups for X, A, $R^1$, $R^2$, $R^3$, $R^5$, $R^6$. $R^a$, $R^b$, $R^c$ and $R^d$, in any combination thereof, are as set out below.

Preferably, X is O.

In one embodiment, A is

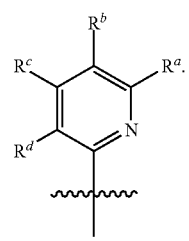

In another embodiment, A is

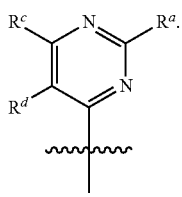

In another embodiment, A is

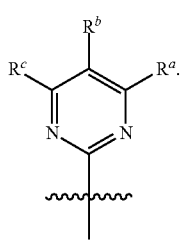

In another embodiment, A is

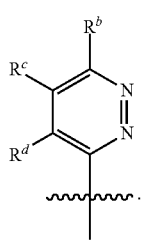

In a preferred embodiment, A is

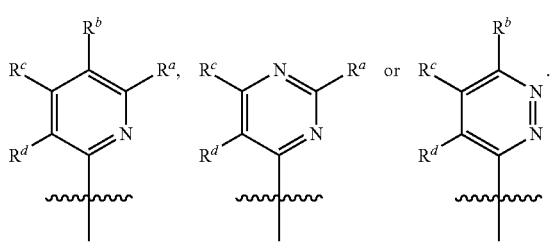

In a more preferred embodiment, A is

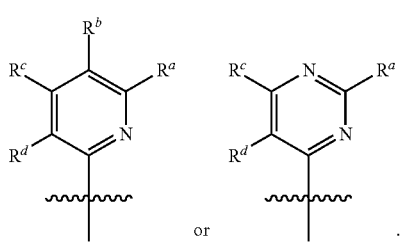

In a preferred embodiment, A is 5-[2-ethoxyvinyl]-4-(trifluoromethyl)pyridine-2-yl.

In a preferred embodiment, A is 5-(1,2-dimethylprop-1-enyl)-4-(trifluoromethyl)pyridine-2-yl.
In a preferred embodiment, A is 3-fluoro-4-trifluoromethylpyridin-2-yl.
In a preferred embodiment, A is 5-(2-methylprop-1-enyl)-4-(trifluoromethyl)pyridine-2-yl.
In a preferred embodiment, A is 5-[prop-1-enyl]-4-(trifluoromethyl)pyridine-2-yl.
In a preferred embodiment, A is 5-methylsulfanylpyridine-2-yl.
In a preferred embodiment, A is 5-bromo-4-methylpyridin-2-yl.
In a preferred embodiment, A is 6-chloro-4-trifluoromethylpyridin-2-yl.
In a preferred embodiment, A is 4-methylpyridin-2-yl.
In a preferred embodiment, A is 5-methylpyridin-2-yl.
In a preferred embodiment, A is 4-methylsulfinyl pyridin-2-yl.
In a preferred embodiment, A is 5-methoxy-pyridin-2-yl.
In a preferred embodiment, A is 5-bromo-4-trifluoromethylpyridin-2-yl.
In a preferred embodiment, A is 5-chloropyridin-2-yl.
In a preferred embodiment, A is 4-methoypyridin-2-yl.
In a preferred embodiment, A is 5-trifluoromethylpyridin-2-yl.
In a preferred embodiment, A is 5-trifluoromethoxypyridin-2-yl.
In a preferred embodiment, A is 4-trifluoromethylpyridin-2-yl.
In a preferred embodiment, A is 4-cyanopyridin-2-yl.
In a preferred embodiment, A is 5-fluoropyridin-2-yl.
In a preferred embodiment, A is 4-chloropyridin-2-yl.
In a preferred embodiment, A is 4,5-dichloropyridin-2-yl.
In a preferred embodiment, A is 4-bromopyridin-2-yl.
In a preferred embodiment, A is 4-fluoropyridin-2-yl.
In a preferred embodiment, A is 5-chloro-4-trifluoromethylpyridin-2-yl.
In a preferred embodiment, A is 5-methoxy-4-trifluoromethylpyridin-2-yl.
In a preferred embodiment, A is 5-cyano-4-trifluoromethylpyridin-2-yl.
In a preferred embodiment, A is 5-methyl-4-trifluoromethylpyridin-2-yl.
In a preferred embodiment, A is 5-vinyl-4-trifluoromethylpyridin-2-yl.
In a preferred embodiment, A is 5-(1-propen-1-yl)-4-trifluoromethylpyridin-2-yl.
In a preferred embodiment, A is 4-(2-fluoroethyl)pyridin-2-yl.
In a preferred embodiment, A is 4-(2,2-difluoroethyl)pyridin-2-yl.
In a preferred embodiment, A is 4-(2,2-difluoromethyl)pyridin-2-yl.
In a preferred embodiment, A is 4-(2-fluoro-2-methylethyl)pyridin-2-yl.
In a preferred embodiment, A is 5-bromo-4-trifluoromethylpyridin-2-yl.
In a preferred embodiment, A is 5-methoxycabonyl-4-trifluoromethylpyridin-2-yl.
In a preferred embodiment, A is 5-isopropoxycabonyl-4-isopropylpyridin-2-yl.
In a preferred embodiment, A is 4-tert-butyl pyridin-2-yl.
In a preferred embodiment, A is 5-methylsulfinyl pyridin-2-yl.
In a preferred embodiment, A is 4,5-bistrifluoromethyl pyridin-2-yl.

In a preferred embodiment, A is 6-chloropyridazin-3-yl.
In a preferred embodiment, A is 5-methyl-6-methoxypyridazin-3-yl.
In a preferred embodiment, A is 6-methoxy-pyridazin-3-yl.
In a preferred embodiment, A is 6-trifluoromethyl-pyridazin-3-yl.
In a preferred embodiment, A is 6-methylpyridazin-3-yl.
In a preferred embodiment, A is 6-phenylpyridazin-3-yl.
In a preferred embodiment, A is 6-chloro-5-tert-butylpyridazin-3-yl.
In a preferred embodiment, A is 6-trifluoromethylpyrimidin-4-yl.
In a preferred embodiment, A is 6-tert-butylpyrimidin-4-yl.
In a preferred embodiment, A is 6-cyclopropylpyrimidin-4-yl.
In a preferred embodiment, A is 6-isopropoxypyrimidin-4-yl.
In a preferred embodiment, A is 4-tert-butylpyrimidin-2-yl.
In a preferred embodiment, A is 4-trifluoromethylpyrimidin-2-yl.

Preferably, $R^a$ is selected from hydrogen and fluorine. Most preferably, $R^a$ is hydrogen.

Preferably $R^b$ is selected from hydrogen, formyl, hydroxyl, halogen, nitro, cyano, $C_1$-$C_6$ alkyl, $C_1$-$C_6$ cyanoalkyl, $C_3$-$C_6$ cycloalkyl, $C_3$-$C_6$ cyanocycloalkyl, $C_1$-$C_6$ haloalkyl, $C_1$-$C_6$ alkylthio, $C_1$-$C_6$ alkoxy, $C_1$-$C_6$ alkoxy $C_1$-$C_6$ alkyl, $C_1$-$C_6$ alkoxy $C_1$-$C_6$ alkoxy, $C_1$-$C_6$ alkylthio $C_1$-$C_6$ alkyl, $C_1$-$C_6$ cyanoalkoxy, $C_1$-$C_6$ haloalkoxy, $C_2$-$C_6$ alkenyl, $C_2$-$C_6$ alkynyl, $C_2$-$C_6$ cyanoalkenyl, $C_2$-$C_6$ cyanoalkynyl, $C_2$-$C_6$ alkenyloxy, $C_2$-$C_6$ alkynyloxy, $C_2$-$C_6$ haloalkenyl, $C_2$-$C_6$ haloalkynyl, $C_2$-$C_6$ haloalkenyloxy, $C_2$-$C_6$ haloalkynyloxy, $C_1$-$C_6$ alkoxy $C_2$-$C_6$ alkenyl, $C_1$-$C_6$ alkoxy $C_2$-$C_6$ alkynyl, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, $C_1$-$C_6$ alkylsulfonyloxy, $C_1$-$C_6$ alkylcarbonyl, $C_1$-$C_6$ haloalkylcarbonyl, a group $R^{10}O(O)C$—, $C_2$-$C_6$ alkenylcarbonyl, $C_2$-$C_6$ alkynylcarbonyl, $C_2$-$C_6$ haloalkenylcarbonyl, $C_2$-$C_6$ haloalkynylcarbonyl, $C_1$-$C_6$ alkoxycarbonyloxy, $C_1$-$C_6$ alkenyloxycarbonyloxy, $C_1$-$C_6$ alkynyloxycarbonyloxy, $C_1$-$C_6$ haloalkoxycarbonyloxy, tri $C_1$-$C_6$ alkylsilyl $C_2$-$C_6$ alkynyl, a group $R^6R^6N$—, a group $R^6C(O)N(R^6)$—, a group $R^5S(O_2)N(R^6)$—, a group $R^6R^6NC(O)$—, a group $R^5R^6NC(O)O$—, a group $R^6R^6NSO_2$—, a $C_6$-$C_{10}$ aryl group optionally substituted by from 1 to 3 groups independently selected from halogen, nitro, cyano, $C_1$-$C_3$ alkyl, $C_1$-$C_3$ alkoxy, $C_1$-$C_3$ haloalkyl, $C_1$-$C_3$ haloalkoxy and a $C_5$-$C_{10}$ heteroaryl group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy; a $C_6$-$C_{10}$ aryloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy; a $C_6$-$C_{10}$ benzyl group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy; a $C_6$-$C_{10}$ benzyloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy; a $C_3$-$C_6$ heterocyclyl group optionally substituted by from 1 to 3 groups independently selected from $C_1$-$C_4$ alkyl; a heterocyclyl $C_1$-$C_6$ alkoxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy; and a $C_3$-$C_6$ cycloalkyl ring optionally comprising from 1 to 3 heteroatoms independently selected from S, O and N and optionally substituted with from 1 to 3 groups independently selected from halogen or $C_1$-$C_6$ alkyl; or $R^b$ and $R^c$ together with the carbon atoms to which they are attached form a 3-6 membered saturated or partially unsaturated ring optionally comprising from 1 to 3 heteroatoms independently selected from S, O and N and optionally substituted with from 1 to 3 groups independently selected from halogen or $C_1$-$C_6$ alkyl;

More preferably, $R^b$ is selected from hydrogen, halogen, cyano, $C_1$-$C_6$ alkyl, $C_1$-$C_6$ haloalkyl, $C_1$-$C_6$ alkylthio, $C_1$-$C_6$ cyanoalkenyl, $C_1$-$C_6$ alkoxy, $C_1$-$C_6$ haloalkoxy, $C_1$-$C_6$ alkoxy $C_1$-$C_6$ alkoxy, $C_2$-$C_6$ alkenyl, $C_2$-$C_6$ alkynyl, $C_1$-$C_6$ alkoxy $C_2$-$C_6$ alkenyl, $C_1$-$C_6$ alkylsulfinyl, $C_1$-$C_6$ alkylsulfonyl, $C_1$-$C_6$ alkylcarbonyl, a group $R^{10}O(O)C$—, a group $R^5R^6NC(O)$—, a group $R^5C(O)N(R^6)$—, a group $R^6R^6NSO_2$—, tri $C_1$-$C_6$ alkylsilyl $C_2$-$C_6$ alkynyl, a $C_6$-$C_{10}$ aryl group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy, a $C_6$-$C_{10}$ aryloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy; a $C_5$-$C_{10}$ heteroaryl group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy; a $C_3$-$C_6$ heterocyclyl group optionally substituted by from 1 to 3 groups independently selected from $C_1$-$C_4$ alkyl and a heterocyclyl $C_1$-$C_6$ alkoxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy. More preferably, $R^b$ is selected from hydrogen, halogen, cyano, $C_1$-$C_4$ alkyl, $C_1$-$C_4$ alkylcarbonyl, $C_1$-$C_4$ haloalkyl, $C_2$-$C_4$ alkenyl, a group $R^{10}O(O)C$—, $C_1$-$C_6$ haloalkoxy or $C_1$-$C_4$ alkoxy. Even more preferably, $R^b$ is selected from hydrogen, halogen, cyano, $C_1$-$C_4$ alkyl, $C_1$-$C_4$ alkenyl or $C_1$-$C_4$ haloalkyl. Even more preferably $R^b$ is selected from hydrogen, bromo, chloro, fluoro, methyl, vinyl, 1-propen-1-yl, trifluoromethyl, isopropoxycarbonyl, methoxy, methylcarbonyl. Most preferably, $R^b$ is hydrogen, chloro or trifluoromethyl.

Preferably, $R^c$ is selected from hydrogen, halogen, cyano, $C_1$-$C_6$ alkyl, $C_1$-$C_6$ cycloalkyl, $C_1$-$C_6$ alkylcarbonyl, $C_1$-$C_6$ haloalkyl, $C_1$-$C_6$ cyanoalkyl, $C_1$-$C_6$ alkoxy, $C_1$-$C_6$ haloalkoxy, $C_2$-$C_6$ alkenyl, $C_1$-$C_6$ alkylsulfinyl, a group $R^6R^6N$—. More preferably, $R^c$ is selected from hydrogen, cyano, halogen, $C_1$-$C_4$ alkyl or $C_1$-$C_4$ haloalkyl. Even more preferably, $R^c$ is selected from halogen, $C_1$-$C_4$ alkyl or $C_1$-$C_4$ haloalkyl. Even more preferably $R^c$ is selected from bromo, chloro, fluoro, 1-fluoroethyl, 1,1-difluoroethyl, difluoromethyl, 1-fluoro-1-methylethyl, methyl, iso-propyl, tert-butyl or trifluoromethyl. Most preferably, $R^c$ is iso-propyl, tert-butyl or trifluoromethyl.

Preferably, $R^d$ is selected from hydrogen, cyano, fluoro or chloro. More preferably, $R^d$ is selected from hydrogen, chloro and fluoro. Most preferably, $R^d$ is hydrogen.

Preferably, $R^1$ is methyl, ethyl, methoxy or ethoxy, with the proviso that when $R^1$ is methoxy or ethoxy, $R^2$ is not methoxy, ethoxy, allyloxy or 2,2,2-trifluoroethyloxy.

Preferably, $R^2$ is bromo, chloro, methoxy, ethoxy, allyloxy or 2,2,2-trifluoroethyloxy with the proviso that when $R^1$ is methoxy or ethoxy, $R^2$ is not methoxy, ethoxy, allyloxy or 2,2,2-trifluoroethyloxy.

Preferably, (i) $R^1$ is methyl and $R^2$ is bromo, (ii) $R^1$ is methyl and $R^2$ is chloro, (iii) $R^1$ is methyl and $R^2$ is methoxy, (iv) $R^1$ is methoxy and $R^2$ is bromo, (v) $R^1$ is methoxy and $R^2$ is chloro, (vi) $R^1$ is methyl and $R^2$ is allyloxy or (vi) $R^1$ is methyl and $R^2$ is 2,2,2-trifluoroethyloxy. Even more preferrably, (i) $R^1$ is methyl and $R^2$ is chloro, (ii) $R^1$ is methyl and $R^2$ is methoxy or (iii) $R^1$ is methoxy and $R^2$ is bromo.

Preferably, $R^3$ is halogen, hydroxyl or $C_1$-$C_6$ alkylcarbonyloxy. More preferably, $R^3$ is hydroxyl or halogen. Most preferably, $R^3$ is hydroxyl.

Preferably, $R^5$ and $R^6$ are independently selected from hydrogen, $C_1$-$C_6$ alkyl, $C_1$-$C_6$ haloalkyl, $C_2$-$C_6$ alkenyl, and $C_2$-$C_6$ alkynyl, or $R^5$ and $R^6$ together with the carbon atoms to which they are attached form a saturated or partially unsaturated 3-6 membered ring optionally comprising from 1 to 3 heteroatoms independently selected from S, O and N and optionally substituted with from 1 to 3 groups independently selected from halogen or $C_1$-$C_6$ alkyl. More preferably, $R^5$ and $R^6$ are independently selected from hydrogen, $C_1$-$C_4$ alkyl and $C_1$-$C_4$ haloalkyl. Most preferably, where both $R^5$ and $R^6$ are present, one of $R^5$ and $R^6$ is selected from hydrogen or methyl and the other is $C_1$-$C_4$ alkyl, preferably t-butyl.

Preferably, $R^{10}$ is selected from $C_1$-$C_6$ alkyl, $C_1$-$C_6$ haloalkyl, $C_2$-$C_6$ alkenyl and $C_2$-$C_6$ alkynyl.

In a particularly preferred embodiment, X is O, A, $R^b$, $R^1$, $R^2$ and $R^3$ are as described above, $R^a$ and $R^d$ are hydrogen and $R^c$ is (i) $C_1$-$C_6$ alkyl, (ii) $C_1$-$C_6$ haloalkyl, (iii) halogen or (iv) cyano.

The herbicidal compounds of formula (I) may exist as different geometric isomers, or in different tautomeric forms. This invention covers all such isomers and tautomers, and mixtures thereof in all proportions, as well as isotopic forms such as deuterated compounds.

The herbicidal compounds of this invention may contain an asymmetric carbon atom and some of the compounds of this invention may contain one or more asymmetric centers and may thus give rise to optical isomers and diastereomers. While shown without respect to stereochemistry, the present invention includes such optical isomers and diastereomers; as well as the racemic and resolved, enantiomerically pure R and S stereoisomers; as well as other mixtures of the R and S stereoisomers and agrochemically acceptable salts thereof. It is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

Alkyl, as used herein refers to an aliphatic hydrocarbon chain and includes straight and branched chains e. g. of 1 to 6 carbon atoms such as methyl, ethyl, n-propyl, isopropyl, n-butyl, isobutyl, sec-butyl, t-butyl, n-pentyl, isopentyl, neo-pentyl, n-hexyl, and isohexyl.

Alkenyl, as used herein, refers to an aliphatic hydrocarbon chain having at least one double bond, and preferably one double bond, and includes straight and branched chains e. g. of 2 to 6 carbon atoms such as ethenyl (vinyl), prop-1-enyl, prop-2-enyl (allyl), isopropenyl, but-1-enyl, but-2-enyl, but-3-enyl, 2-methypropenyl.

Alkynyl, as used herein, refers to an aliphatic hydrocarbon chain having at least one triple bond, and preferably one triple bond, and includes straight and branched chains e. g. of 2 to 6 carbon atoms such as ethynyl, prop-1-ynyl, prop-2-ynyl (propargyl) but-1-ynyl, but-2-ynyl and but-3-ynyl.

Cycloalkyl, as used herein, refers to a cyclic, saturated hydrocarbon group having from 3 to 6 ring carbon atoms. Examples of cycloalkyl groups are cyclopropyl, cyclobutyl, cyclopentyl and cyclohexyl.

Alkoxy as used herein refers to the group —OR, wherein R is alkyl as defined above. Examples of alkoxy groups include methoxy, ethoxy, n-propoxy, isopropoxy, n-butoxy, isobutoxy, sec-butoxy, t-butoxy, n-pentoxy, isopentoxy, neo-pentoxy, n-hexyloxy, and isohexyloxy.

Alkenyloxy refers to the group —OR, wherein R is alkenyl as defined above. Examples of alkenyloxy groups are ethenyloxy, propenyloxy, isopropenyloxy, but-1-enyloxy, but-2-enyloxy, but-3-enyloxy, 2-methypropenyloxy etc.

Alkynyloxy refers to the group —OR, wherein R is alkynyl is as defined above. Examples of alkynyloxy groups are ethynyloxy, propynyloxy, but-1-ynyloxy, but-2-ynyloxy and but-3-ynyloxy.

Alkoxyalkyl as used herein refers to the group —ROR, wherein each R is, independently, an alkyl group as defined above.

Alkoxyalkenyl as used herein refers to the group —ROR', wherein R' is an alkyl group as defined above and R is an alkenyl group as defined above.

Alkoxyalkynyl as used herein refers to the group —ROR', wherein R' is an alkyl group as defined above and R' is an alkynyl group as defined above.

Alkoxyalkoxy, as ued herein, refers to the group —OROR, wherein each R is, independently, an alkyl group as defined above.

Cyanoalkyl as used herein refers to an alkyl group substituted with one or more cyano groups.

Cyanoalkenyl as used herein refers to an alkenyl group substituted with one or more cyano groups.

Cyanoalkynyl as used herein refers to an alkynyl group substituted with one or more cyano groups.

Cyanocycloalkyl as used herein refers to an cycloalkyl group substituted with one or more cyano groups.

Cyanoalkoxy as used herein refers to the group —OR, wherein R is cyanoalkyl as defined above.

Halogen, halide and halo refer to iodine, bromine, chlorine and fluorine.

Haloalkyl as used herein refers to an alkyl group as defined above wherein at least one hydrogen atom has been replaced with a halogen atom as defined above. Examples of haloalkyl groups include chloromethyl, dichloromethyl, trichloromethyl, fluoromethyl, difluoromethyl and trifluoromethyl. Preferred haloalkyl groups are fluoroalkyl groups {i.e. haloalkyl groups, containing fluorine as the only halogen). More highly preferred haloalkyl groups are perfluoroalkyl groups, i.e. alkyl groups wherein all the hydrogen atoms are replaced with fluorine atoms.

Haloalkenyl as used herein refers to an alkenyl group as defined above wherein at least one hydrogen atom has been replaced with a halogen atom as defined above.

Haloalkynyl as used herein refers to an alkynyl group as defined above wherein at least one hydrogen atom has been replaced with a halogen atom as defined above.

Haloalkoxy as used herein refers to the group —OR, wherein R is haloalkyl as defined above.

Haloalkenyloxy as used herein refers to the group —OR, wherein R is haloalkenyl as defined above.

Haloalkynyloxy as used herein refers to the group —OR, wherein R is haloalkynyl as defined above.

Alkylthio as used herein refers to the group —SR, wherein R is an alkyl group as defined above.

Alkylthio groups include, but are not limited to, methylthio, ethylthio, propylthio, tert-butylthio, and the like.

Alkylthioalkyl as used herein refers to the group —RSR, wherein each R is, independently, an alkyl group as defined above.

Haloalkylthio as used herein refers to the group —SR, wherein R is a haloalkyl group as defined above.

Alkylsulfinyl as used herein refers to the group —S(O)R, wherein R is an alkyl group as defined above.

Alkylsulfonyl as used herein refers to the group —S(O)$_2$R, wherein R is an alkyl group as defined above.

Haloalkylsulfinyl as used herein refers to the group —S(O)R, wherein R is a haloalkyl group as defined above.

Haloalkylsulfonyl as used herein refers to the group —S(O)$_2$R, wherein R is a haloalkyl group as defined above.

Alkylsulfonyloxy, as used herein refers to the group —OS(O)$_2$R, wherein R is an alkyl group as defined above.

Alkylcarbonyl, as used herein refers to the group —C(O)R, wherein R is an alkyl group as defined above. Examples of alkylcarbonyl groups include ethanoyl, propanoyl, n-butanoyl, etc.

Alkenylcarbonyl, as used herein refers to the group —C(O)R, wherein R is an alkenyl group as defined above.

Alkynylcarbonyl, as used herein refers to the group —C(O)R, wherein R is an alkynyl group as defined above.

Haloalkylcarbonyl, as used herein refers to the group —C(O)R, wherein R is a haloalkyl group as defined above.

Haloalkenylcarbonyl, as used herein refers to the group —C(O)R, wherein R is a haloalkenyl group as defined above.

Haloalkynylcarbonyl, as used herein refers to the group —C(O)R, wherein R is a haloalkynyl group as defined above.

Alkoxycarbonyloxy as used herein, refers to the group —OC(O)OR, wherein R is an alkyl group as defined above. Examples of alkoxycarbonyloxy groups are methoxycarbonyloxy, ethoxycarbonyloxy, propoxycarbonyloxy, but-1-oxycarbonyloxy, but-2-oxycarbonyloxy and but-3-oxycarbonyloxy.

Alkenyloxycarbonyloxy, as used herein, refers to the group —OC(O)OR, wherein R is an alkenyl group as defined above.

Alkynyloxycarbonyloxy, as used herein, refers to the group —OC(O)OR, wherein R is an alkynyl group as defined above.

Haloalkoxycarbonyloxy, as used herein, refers to the group —OC(O)OR, wherein R is a haloalkyl group as defined above.

Trialkylsilylalkynyl, as used herein, refers to the group —RSi(R')$_3$, wherein R is an alkynyl group as defined above and each R' is, independently, selected from an alkyl group as defined above.

Formyl, as used herein, refers to the group —C(O)H.

Hydroxy or hydroxyl, as used herein, refers to the group —OH.

Nitro, as used herein, refers to the group —NO$_2$.

Cyano, as used herein, refers to the group —CN.

Aryl, as used herein, refers to an unsaturated aromatic carbocyclic group of from 6 to 10 carbon atoms having a single ring (e.g., phenyl) or multiple condensed (fused) rings, at least one of which is aromatic (e.g., indanyl, naphthyl). Preferred aryl groups include phenyl, naphthyl and the like. Most preferably, an aryl group is a phenyl group.

Aryloxy, as used herein, refers to the group —O-aryl, wherein aryl is as defined above.

Preferred aryloxy groups include phenoxy, naphthyloxy and the like.

Benzyl, as used herein, refers to the group —CH$_2$C$_6$H$_5$. Benzyl groups may be substituted on the alkyl linker or on the ring.

Benzyloxy, as used herein, refers to the group —OCH$_2$C$_6$H$_5$. Benzyloxy groups may be substituted on the linker or on the ring.

Heterocyclyl, as used herein, refers to a non-aromatic ring system containing 3 to 10 ring atoms, at least one ring heteroatom and consisting either of a single ring or of two or more fused rings. Preferably, single rings will contain up to three and bicyclic systems up to four heteroatoms which will preferably be chosen from nitrogen, oxygen and sulfur. When a ring system contains a sulphur atom, the sulphur atom may be present in any one of its oxidation states e.g. —S—, —S(=O)— or —S(=O$_2$)—. Examples of such groups include pyrrolidinyl, imidazolinyl, pyrazolidinyl, piperidyl, piperazinyl, quinuclidinyl, morpholinyl, together with unsaturated or partially unsaturated analogues such as 4,5,6,7-tetrahydro-benzothiophenyl, chromen-4-onyl, 9H-fluorenyl, 3,4-dihydro-2H-benzo-1,4-dioxepinyl, 2,3-dihydro-benzofuranyl, piperidinyl, 1,3-dioxolanyl, 1,3-dioxanyl, 4,5-dihydro-isoxazolyl, tetrahydrofuranyl and morpholinyl.

Heteroaryl, as used herein, refers to a ring system containing 5 to 10 ring atoms, 1 to 4 ring heteroatoms and consisting either of a single aromatic ring or of two or more fused rings, at least one of which is aromatic. Preferably, single rings will contain up to three and bicyclic systems up to four heteroatoms which will preferably be independently chosen from nitrogen, oxygen and sulfur. When a ring system contains a sulphur atom, the sulphur atom may be present in any one of its oxidation states e.g. —S—, —S(=O)— or —S(=O$_2$)—. Examples of such groups include pyridyl, pyridazinyl, pyrimidinyl, pyrazinyl, triazinyl, furanyl, thiophenyl, oxazolyl, isoxazolyl, oxadiazolyl, thiazolyl, isothiazolyl, thiadiazolyl, pyrrolyl, pyrazolyl, imidazolyl, triazolyl and tetrazolyl. Examples of bicyclic groups are benzothiophenyl, benzimidazolyl, benzothiadiazolyl, quinolinyl, cinnolinyl, quinoxalinyl and pyrazolo[1,5-a]pyrimidinyl.

'Saturated ring', as used herein, refers to a ring system in which the atoms in the ring are linked by single bonds and may consist of either a single ring or two or more fused rings.

'Partially unsaturated ring', as used herein, refers to a ring system in which at least two atoms in the ring are linked by a double bond and may consist of either a single ring or two or more fused rings. Partially unsaturated ring systems do not include aromatic rings.

"Optionally substituted" as used herein means the group referred to can be substituted at one or more positions by any one or any combination of the radicals listed thereafter. For most groups, one or more hydrogen atoms are replaced by the radicals listed thereafter. For halogenated groups, for example, haloalkyl groups, one or more halogen atoms are replaced by the radicals listed thereafter.

Suitable salts include those derived from alkali or alkaline earth metals and those derived from ammonia and amines. Preferred cations include sodium, potassium, magnesium, and ammonium cations of the formula N$^+$(R$^{19}$R$^{20}$R$^{21}$R$^{22}$) wherein R$^{19}$, R$^{20}$, R$^{21}$ and R$^{22}$ are independently selected from hydrogen, C$_1$-C$_6$ alkyl and C$_1$-C$_8$ hydroxyalkyl. Salts of the compounds of Formula I can be prepared by treatment of compounds of Formula I with a metal hydroxide, such as sodium hydroxide, or an amine, such as ammonia, trimethylamine, diethanolamine, 2-methylthiopropylamine, bisallylamine, 2-butoxyethylamine, morpholine, cyclododecylamine, or benzylamine. Amine salts are often preferred forms of the compounds of Formula I because they are water-soluble and lend themselves to the preparation of desirable aqueous based herbicidal compositions.

Acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety.

In another aspect the present invention provides intermediates useful in the preparation of compounds of the invention.

In one embodiment, there are provided intermediates of formula (II)

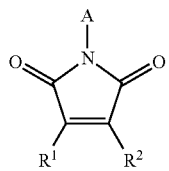

(II)

wherein $R^1$, $R^2$ and A are as defined above.

In a further embodiment, there are provided intermediates of formula (III)

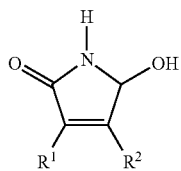

(III)

wherein $R^1$ and $R^2$ are as defined above.

In a further embodiment, there are provided intermediates of formula (IX)

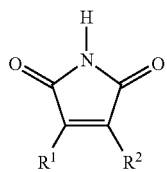

(IX)

wherein $R^1$ and $R^2$ are as defined above.

Compounds of the invention may be prepared by techniques known to the person skilled in the art of organic chemistry. General methods for the production of compounds of formula (I) are described below. Unless otherwise stated in the text, the substituents X, A, $R^1$, $R^2$, $R^3$, $R^a$, $R^b$, $R^c$ and $R^d$ are as defined hereinbefore. The starting materials used for the preparation of the compounds of the invention may be purchased from usual commercial suppliers or may be prepared by known methods. The starting materials as well as the intermediates may be purified before use in the next step by state of the art methodologies such as chromatography, crystallization, distillation and filtration.

For example, compounds of formula (I) wherein $R^3$ is a hydroxyl group may be prepared by reaction of substituted maleic anhydride (IV) with amine (V) under neutral, acidic or Lewis acidic conditions to give maleimide (II), and subsequent reduction with a reducing agent e.g. sodium borohydride to give compound (VI) (compound (I) wherein X=O and $R^3$ is hydroxyl), potentially in a mixture with regioisomer (VII) as a side-product (scheme 1). Suitable conditions for achieving these transformations are disclosed in CH633678. Maleic anhydrides (IV) can be prepared by literature methods (Journal of the Chemical Society, Perkin Transactions 1: Organic and Bio-Organic Chemistry (1972-1999), 1982, p. 215-222, EP1426365 A1, 2004, Journal of Organic Chemistry, 1998, vol. 63, 8, p. 2646-2655).

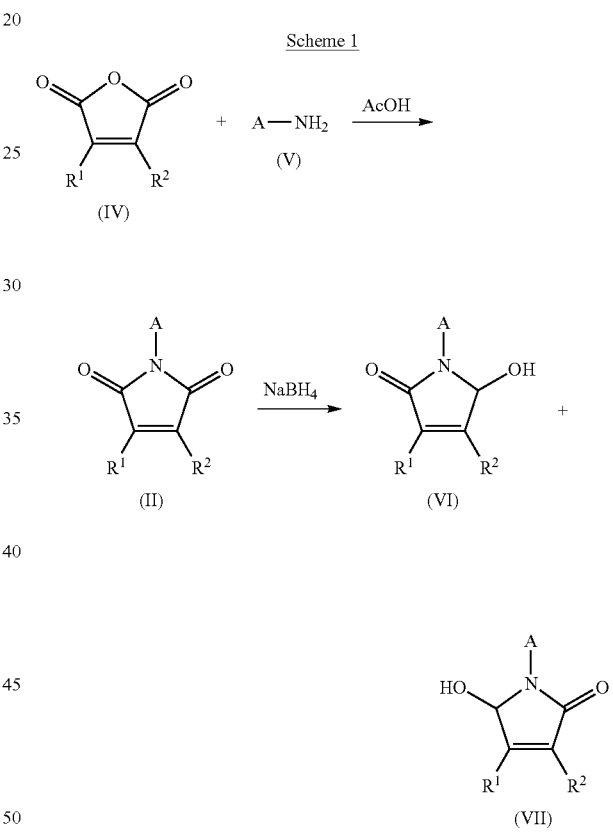

Scheme 1

Alternatively, compounds of formula (I) wherein $R^3$ is a hydroxyl group may be prepared by reaction of a substituted hydroxyl pyrrolone (III) with a group A-X (VIII), where A is as defined above and X is a suitable leaving group, eg. a halogen, in the presence of a transition metal complex [M], often Palladium, e.g. $Pd_2(dba)_3$ or $Pd(OAc)_2$, often in presence of a ligand, e.g. Xantphos or Brettphos, often in presence of a base, e.g. potassium carbonate or cesium carbonate in an inert solvent, e.g. toluene or dioxane to give compound (VI) (compound (I) wherein X=O and $R^3$ is hydroxyl) (scheme 2).

Suitable conditions for effecting transformations as shown in scheme 2 will be known to those skilled in the art, related examples are set out for example in Org. Lett., Vol. 2, No. 8, 2000, 1101-1104.

Scheme 2

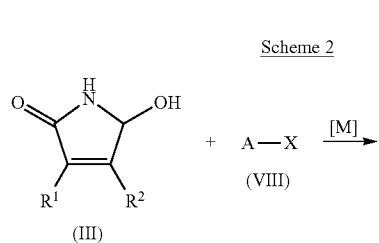

Substituents $R^a$, $R^b$, $R^c$ and $R^d$ on the heteroaromatic ring can either be in place in the amine A-NH2 (V) as shown in scheme 1, or in the A-X (VIII) as shown in scheme 2 or, alternatively, can be introduced at various stages of a reaction sequence through functional group interconversion (FGI) as shown through Schemes 3 to 8, wherein $R^b$, $R^c$, $R^1$, $R^2$, $R^5$ and $R^6$ are as described above and $R^{10}$ is selected from hydrogen, $C_1$-$C_6$ alkyl, $C_1$-$C_6$ haloalkyl, $C_2$-$C_6$ alkenyl or $C_2$-$C_6$ alkynyl. Examples of these transformations are given vide infra.

Scheme 3

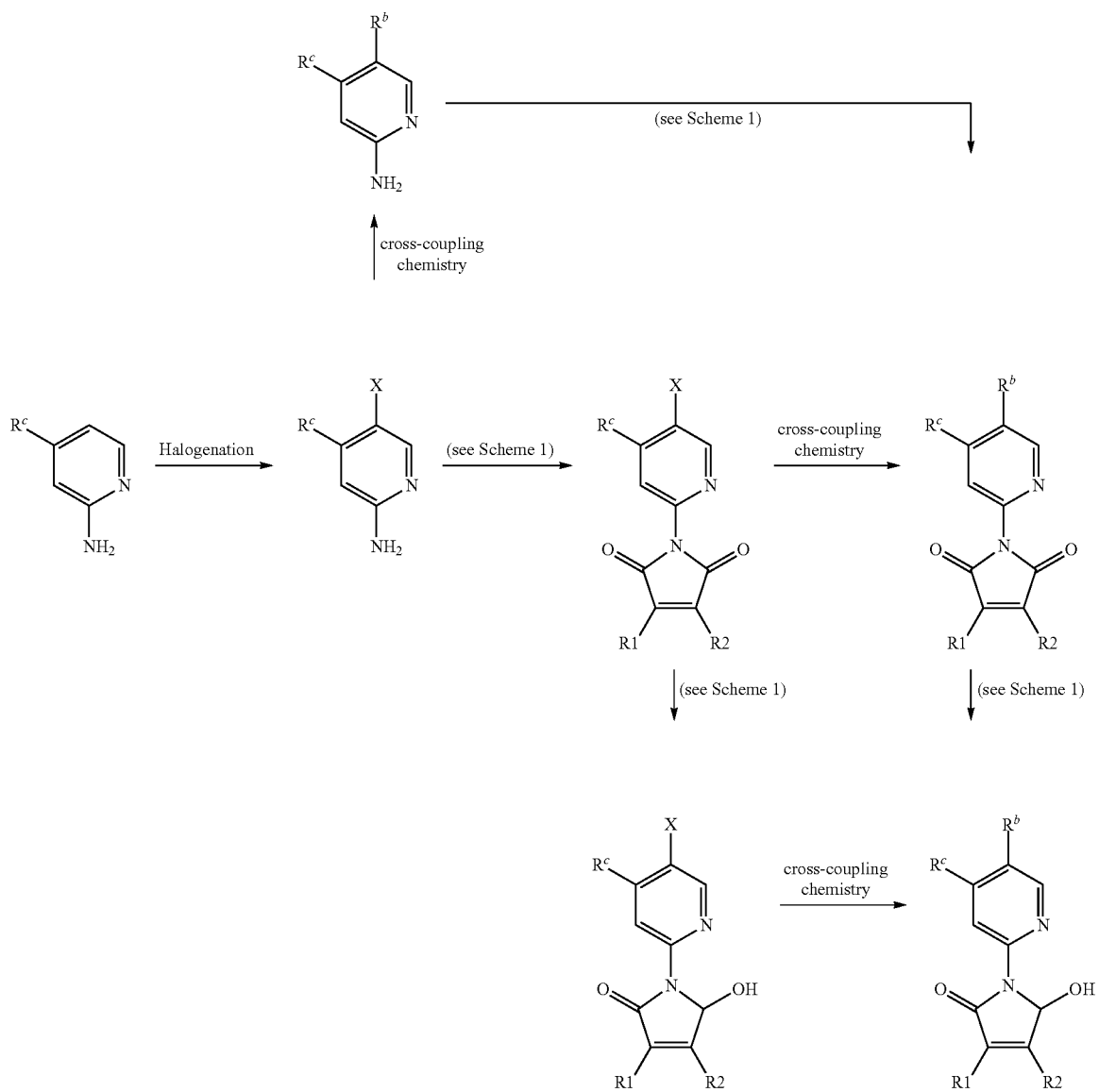

X = Cl, Br, I
Scheme 4
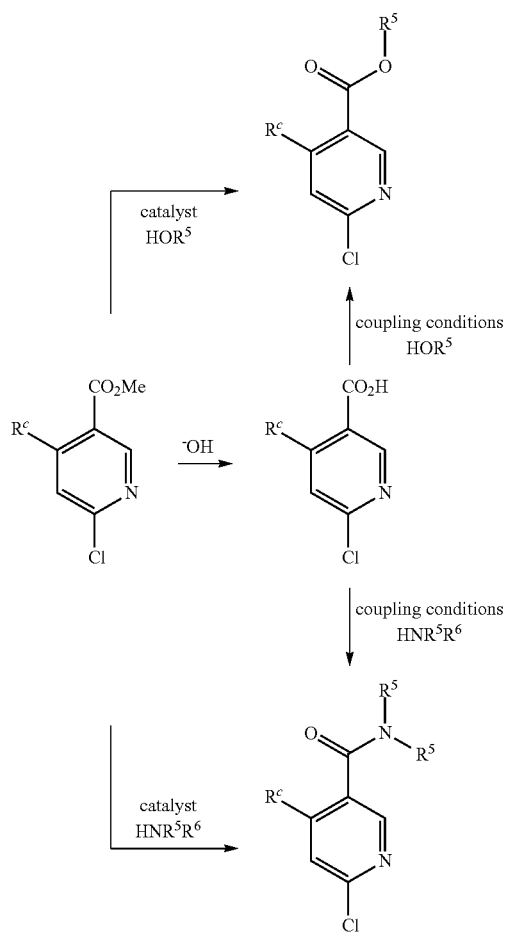
Scheme 5
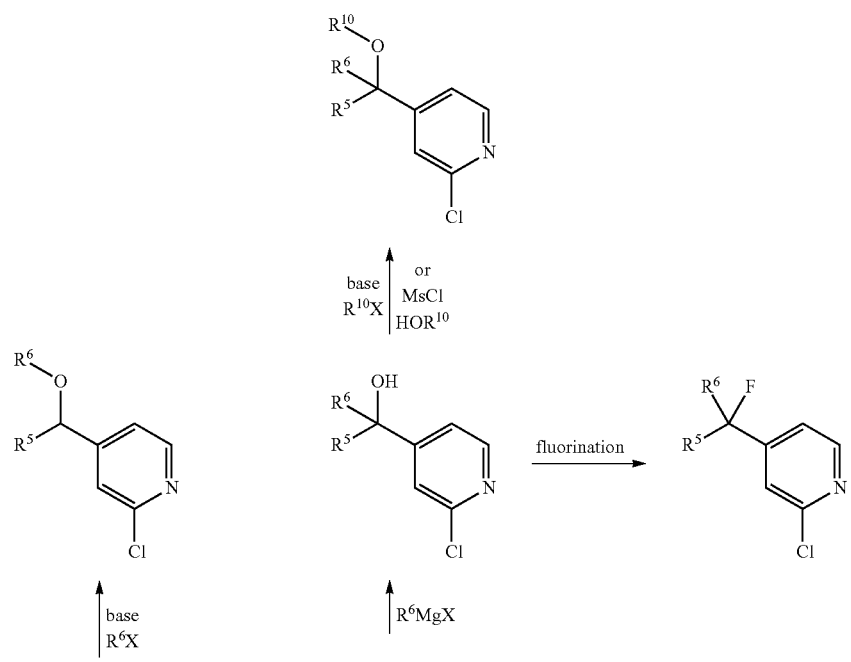

-continued
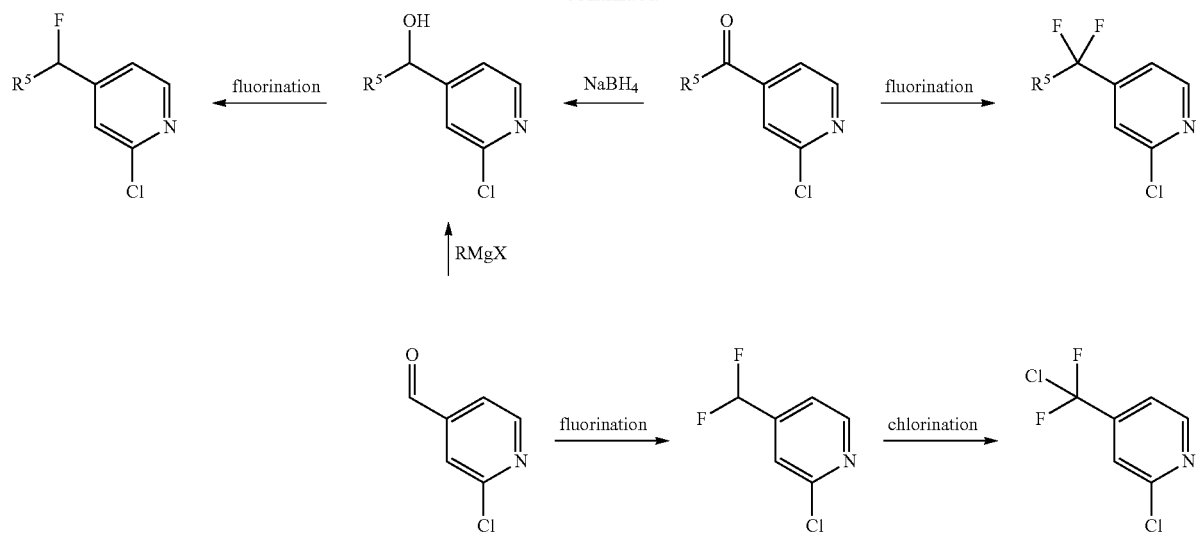
Suitable fluorination reagents include for example diethylaminosulfur trifluoride.
Scheme 6
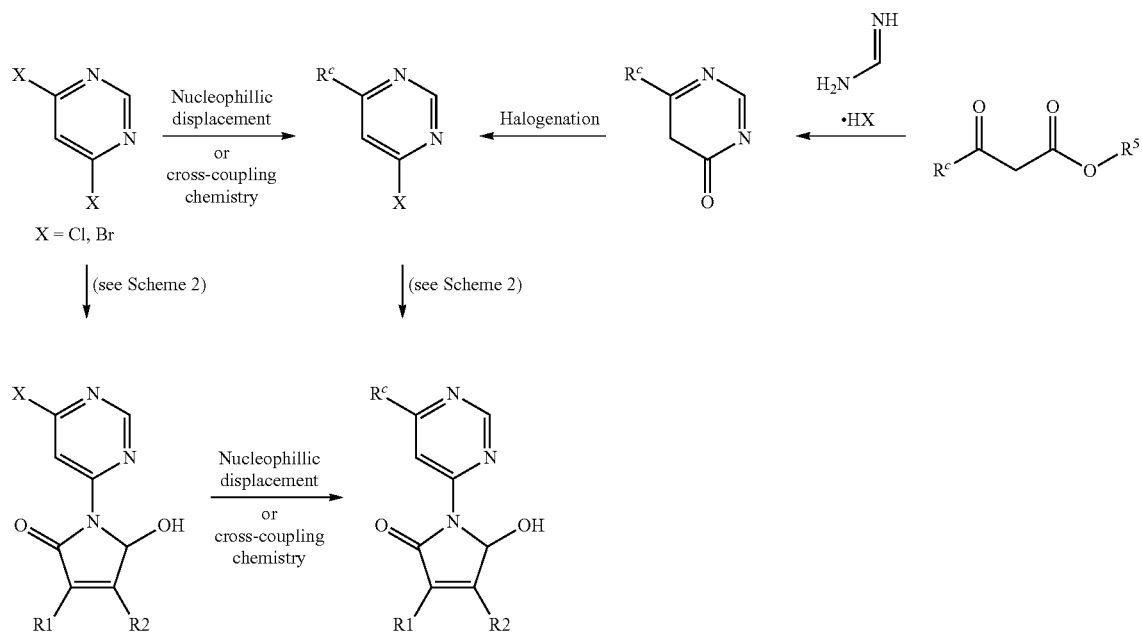
Scheme 7
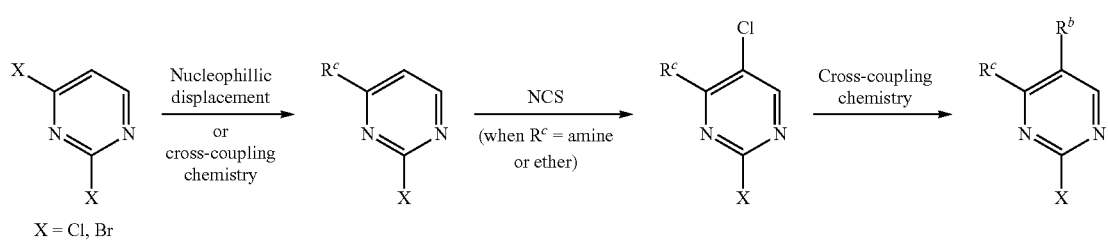

-continued
Scheme 8
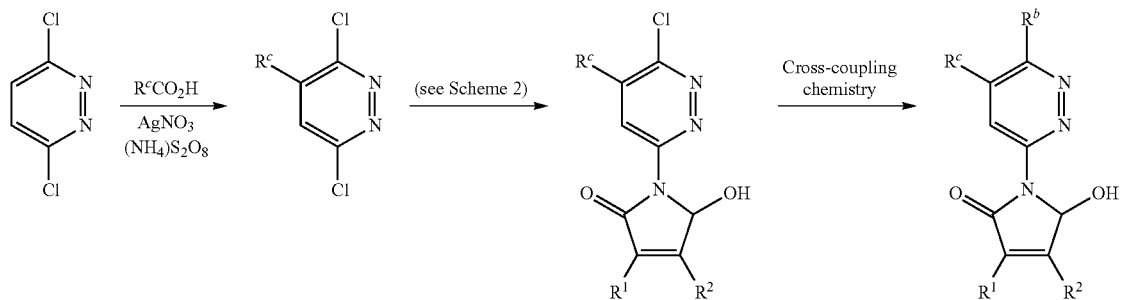
The hydroxypyrrolones (III) can be prepared from the appropriate anhydride (IV), via the imide intermediate (IX), as shown in scheme 9.
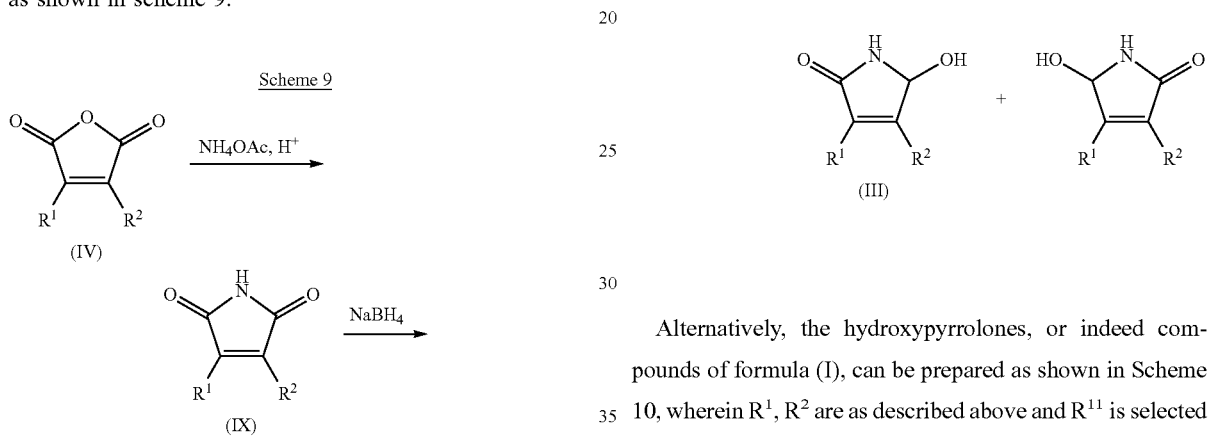
Alternatively, the hydroxypyrrolones, or indeed compounds of formula (I), can be prepared as shown in Scheme 10, wherein $R^1$, $R^2$ are as described above and $R^{11}$ is selected from hydrogen or A as described above.
Scheme 10
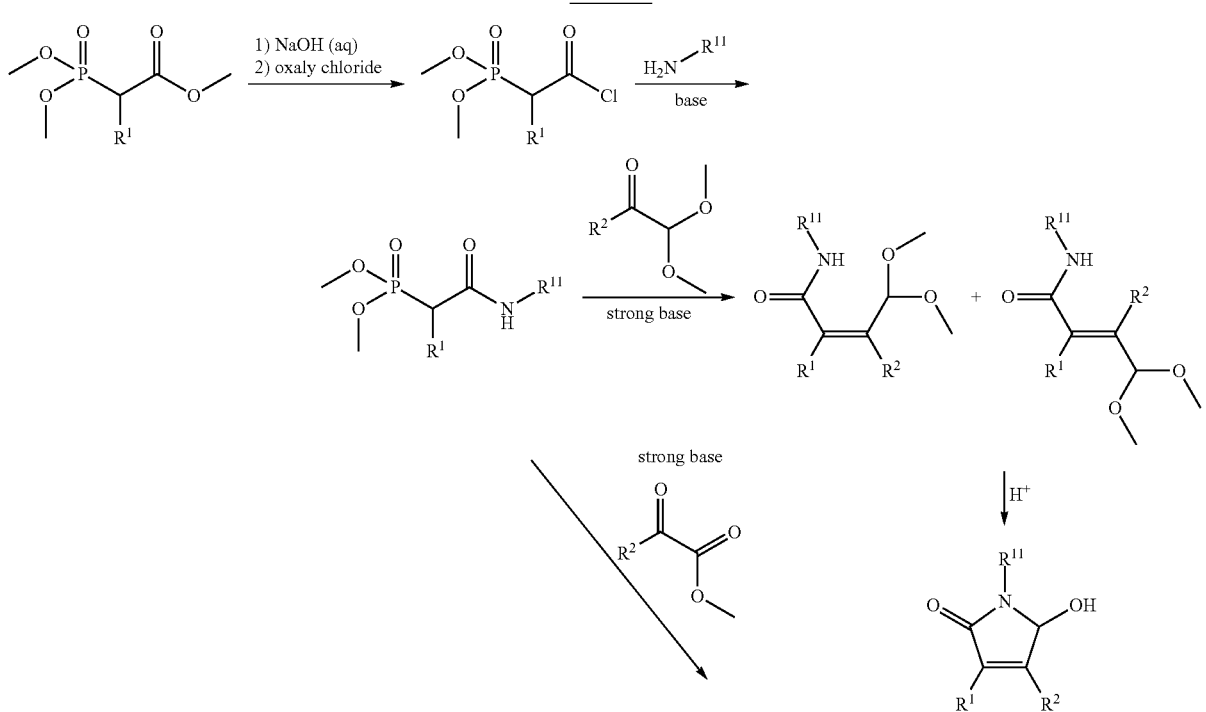

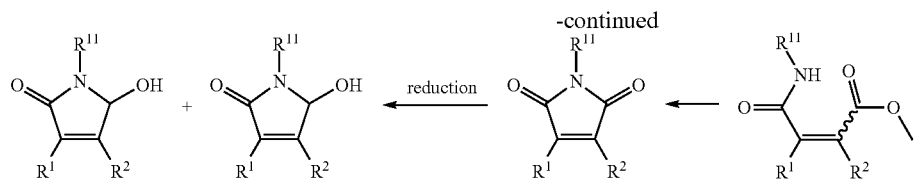

Alternatively, compounds of formula (I) wherein R¹ is halogen may be prepared by halogenation of a maleimide (X) to give 3-halomaleimide (XI). Subsequent reduction with NaBH₄ gives compounds of formula (I) wherein R³ is OH, potentially in a mixture with regioisomer (Ib) as a side-product (Scheme 11).

Scheme 11

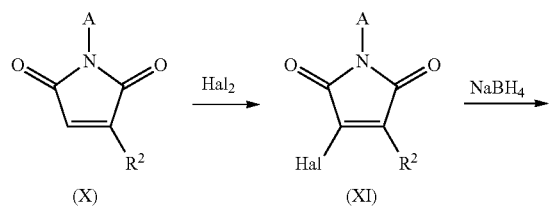

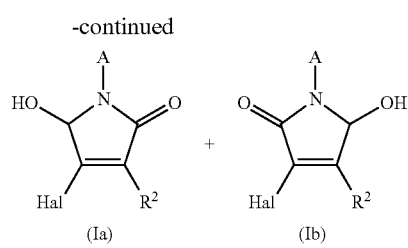

wherein $R^2$ and A are as defined above, and Hal is halogen.

Compound (VI) may be halogenated (i), alkylated (ii), acylated (iii), alkoxyacylated (iv), or sulfonylated (iv) under standard conditions to access other compounds having different values of $R^3$ (scheme 12)

Scheme 12

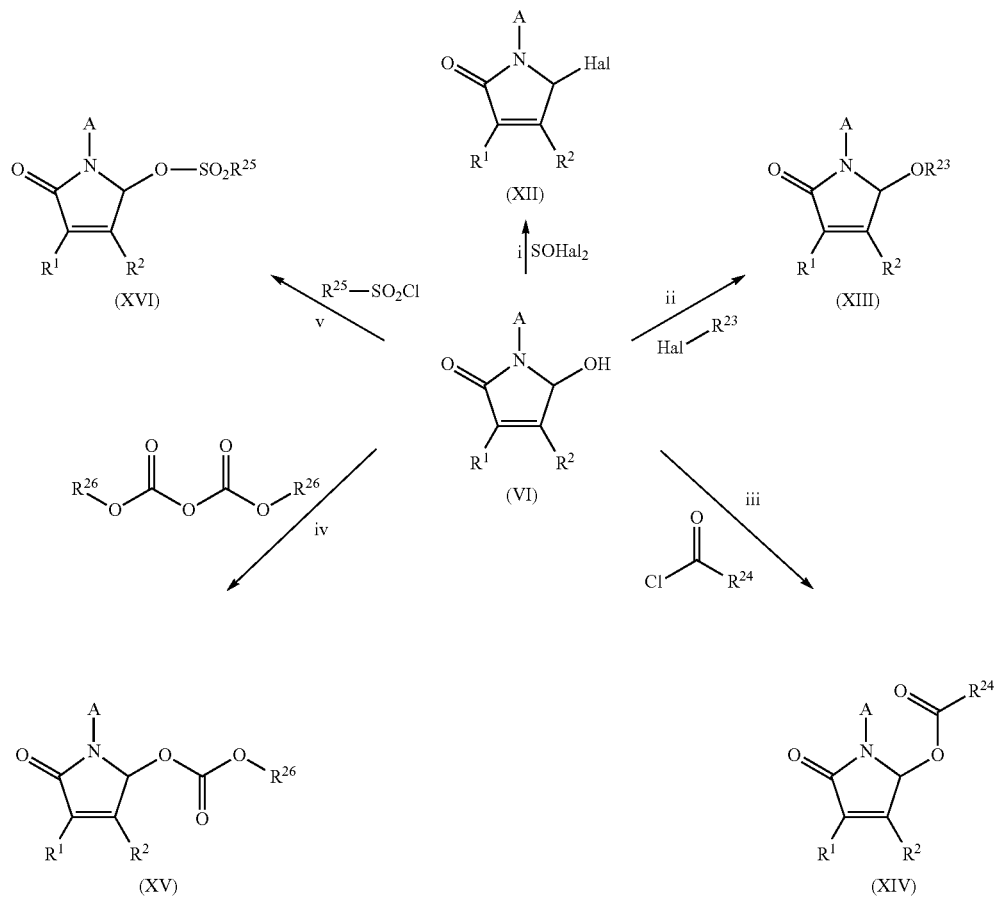

wherein $R^1$, $R^2$ and A are as defined above, Hal is halogen as defined above, $R^{23}$ is selected from $C_1$-$C_6$ alkyl, $C_2$-$C_6$ alkenyl, $C_2$-$C_6$ alkynyl, $R^{24}$ is selected from H and $C_1$-$C_5$ alkyl, $R^{25}$ is selected from $C_1$-$C_6$ alkyl and $C_6$-$C_{10}$ aryl optionally substituted with 1 to 3 groups independently selected from halogen, $C_1$-$C_3$ alkyl, and $C_1$-$C_3$ alkoxy and $R^{26}$ is selected from $C_1$-$C_5$ alkyl.

In general, the chemistry described above is interchangeable across the various azaaryls described (pyridines, pyriminides and pyridazines).

The compounds of formula (I) according to the invention can be used as herbicides in unmodified form, as obtained in the synthesis, but they are generally formulated into herbicidal compositions in various ways using formulation adjuvants, such as carriers, solvents and surface-active substances. Therefore, the invention also relates to a herbicidal composition which comprises a herbicidally effective amount of a compound of formula (I) in addition to formulation adjuvants. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO Specifications for Plant Protection Products, 5th Edition, 1999. Such formulations can either be used directly or they are diluted prior to use. The dilutions can be made, for example, with water, liquid fertilizers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof. The active ingredients can also be contained in very fine microcapsules consisting of a polymer. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art in this connection. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like. Water is generally the carrier of choice for diluting the concentrates. Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances, as described, for example, in CFR 180.1001. (c) & (d).

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in "McCutcheon's Detergents and Emulsifiers Annual" MC Publishing Corp., Ridgewood N.J., 1981.

Further adjuvants that can usually be used in pesticidal formulations include crystallization inhibitors, viscosity modifiers, suspending agents, dyes, anti-oxidants, foaming agents, light absorbers, mixing auxiliaries, antifoams, complexing agents, neutralizing or pH-modifying substances and buffers, corrosion inhibitors, fragrances, wetting agents, take-up enhancers, micronutrients, plasticisers, glidants, lubricants, dispersants, thickeners, antifreezes, microbicides, and also liquid and solid fertilizers.

The compositions according to the invention can additionally include an additive comprising an oil of vegetable or animal origin, a mineral oil, alkyl esters of such oils or mixtures of such oils and oil derivatives. The amount of oil additive in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being of importance. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combination with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyloxide-modified heptamethyltriloxanes which are commercially available e.g. as Silwet L-77®, and also perfluorinated surfactants. The concentration of the surface-active substances in relation to the total additive is generally from 1 to 30% by weight. Examples of oil additives consisting of mixtures of oil or mineral oils or derivatives thereof with surfactants are Edenor ME SU®, Turbocharge® (Syngenta AG, CH) or ActipronC (BP Oil UK Limited, GB).

If desired, it is also possible for the mentioned surface-active substances to be used in the formulations on their own, that is to say, without oil additives.

Furthermore, the addition of an organic solvent to the oil additive/surfactant mixture may contribute to an additional enhancement of action. Suitable solvents are, for example, Solvesso® (ESSO) or Aromatic Solvent® (Exxon Corporation). The concentration of such solvents can be from 10 to 80% by weight of the total weight. Oil additives that are present in admixture with solvents are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada).

In addition to the oil additives listed above, for the purpose of enhancing the action of the compositions according to the invention it is also possible for formulations of alkylpyrrolidones (e.g. Agrimax®) to be added to the spray mixture. Formulations of synthetic lattices, e.g. polyacrylamide, polyvinyl compounds or poly-1-p-menthene (e.g. Bond®, Courier® or Emerald®) may also be used. It is also possible for solutions that contain propionic acid, for example Eurogkem Pen-e-trate®, to be added to the spray mixture as action-enhancing agent.

The herbicidal compositions generally comprise from 0.1 to 99% by weight, especially from 0.1 to 95% by weight, compounds of formula (I) and from 1 to 99.9% by weight of a formulation adjuvant which preferably includes from 0 to 25% by weight of a surface-active substance. Whereas commercial products will preferably be formulated as concentrates, the end user will normally employ dilute formulations.

The rates of application of compounds of formula (I) may vary within wide limits and depend on the nature of the soil, the method of application (pre- or post-emergence; seed dressing; application to the seed furrow; no tillage application etc.), the crop plant, the grass or weed to be controlled, the prevailing climatic conditions, and other factors governed by the method of application, the time of application and the target crop. The compounds of formula (I) according to the invention are generally applied at a rate of from 10 to 2000 g/ha, especially from 50 to 1000 g/ha.

Preferred formulations have especially the following compositions (%=percent by weight):
Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%
The following Examples further illustrate, but do not limit, the invention.

Formulation Examples for Herbicides of Formula (I) (%=% by Weight)

| F1. Emulsifiable concentrates | | | | |
|---|---|---|---|---|
| | a) | b) | c) | d) |
| active ingredient | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |

F1. Emulsifiable concentrates

|  | a) | b) | c) | d) |
|---|---|---|---|---|
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be obtained from such concentrates by dilution with water.

F2. Solutions

|  | a) | b) | c) | d) |
|---|---|---|---|---|
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for use in the form of microdrops.

F3. Wettable powders

|  | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

F4. Coated granules

|  | a) | b) | c) |
|---|---|---|---|
| active ingredient | 0.1% | 5% | 15% |
| highly dispersed silicic acid | 0.9% | 2% | 2% |
| inorganic carrier (diameter 0.1-1 mm) e.g. $CaCO_3$ or $SiO_2$ | 99.0% | 93% | 83% |

The active ingredient is dissolved in methylene chloride and applied to the carrier by spraying, and the solvent is then evaporated off in vacuo.

F5. Coated granules

|  | a) | b) | c) |
|---|---|---|---|
| active ingredient | 0.1% | 5% | 15% |
| polyethylene glycol MW 200 | 1.0% | 2% | 3% |
| highly dispersed silicic acid | 0.9% | 1% | 2% |
| inorganic carrier (diameter 0.1-1 mm) e.g. $CaCO_3$ or $SiO_2$ | 98.0% | 92% | 80% |

The finely ground active ingredient is uniformly applied, in a mixer, to the carrier moistened with polyethylene glycol. Non-dusty coated granules are obtained in this manner.

F6. Extruder granules

|  | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

F7. Dusts

|  | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

F8. Suspension concentrates

|  | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

The invention also provides a method of controlling plants which comprises applying to the plants or to the locus thereof a herbicidally effective amount of a compound of formula (I).

The invention also provides a method of inhibiting plant growth which comprises applying to the plants or to the locus thereof a herbicidally effective amount of a compound of formula (I).

The invention also provides a method of controlling weeds in crops of useful plants, comprising applying to said weeds or to the locus of said weeds, or to said useful crop plants, a compound or a composition of the invention. Preferably, said crop of useful plants is a crop of maize plants.

The invention also provides a method of selectively controlling grasses and/or weeds in crops of useful plants which comprises applying to the useful plants or locus thereof or to the area of cultivation a herbicidally effective amount of a compound of formula (I). Preferably, said crop of useful plants is a crop of maize plants.

The term "herbicide" as used herein means a compound that controls or modifies the growth of plants. The term "herbicidally effective amount" means the quantity of such a compound or combination of such compounds that is capable of producing a controlling or modifying effect on the growth of plants. Controlling or modifying effects include all deviation from natural development, for example: killing, retardation, leaf burn, albinism, dwarfing and the like. The term "plants" refers to all physical parts of a plant, including seeds, seedlings, saplings, roots, tubers, stems, stalks, foliage, and fruits. The term "locus" is intended to include soil, seeds, and seedlings, as well as established vegetation and includes not only areas where weeds may already be growing, but also areas where weeds have yet to emerge, and also to areas under cultivation with respect to crops of useful plants. "Areas under cultivation" include land on which the crop plants are already growing and land intended for cultivation with such crop plants. The term "weeds" as used herein means any undesired plant, and thus includes not only agronomically important weeds as described below, but also volunteer crop plants.

The compounds of the invention can be applied before or after planting of the crops, before weeds emerge (pre-emergence application) or after weeds emerge (post-emergence application), and are particularly effective when applied post-emergence to the weeds.

Crops of useful plants in which the composition according to the invention can be used include, but are not limited to, perennial crops, such as citrus fruit, grapevines, nuts, oil palms, olives, pome fruit, stone fruit and rubber, and annual arable crops, such as cereals, for example barley and wheat, cotton, oilseed rape, maize, rice, soy beans, sugar beet, sugar cane, sunflowers, ornamentals, switchgrass, turf and vegetables, especially cereals, maize and soy beans.

The grasses and weeds to be controlled may be both monocotyledonous species, for example *Agrostis, Alopecurus, Avena, Brachiaria, Bromus, Cenchrus, Cyperus, Digitaria, Echinochloa, Eriochloa, Lolium, Monochoria, Panicum, Poa, Rottboellia, Sagittaria, Scirpus, Setaria, Sida* and *Sorghum*, and *dicotyledonous* species, for example *Abutilon, Amaranthus, Chenopodium, Chrysanthemum, Euphorbia, Galium, Ipomoea, Kochia, Nasturtium, Polygonum, Sida, Sinapis, Solanum, Stellaria, Veronica, Viola* and *Xanthium*.

Crops are to be understood as also including those crops which have been rendered tolerant to herbicides or classes of herbicides (e.g. auxins or ALS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink@, respectively.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesize such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

Any method of application to weeds/crop of useful plant, or locus thereof, which is routinely used in agriculture may be used, for example application by spray or broadcast method typically after suitable dilution of a compound of formula (I) (whether said compound is formulated and/or in combination with one or more further active ingredients and/or safeners, as described herein).

The compounds of formula (I) according to the invention can also be used in combination with other active ingredients, e.g. other herbicides, and/or insecticides, and/or acaricides, and/or nematocides, and/or molluscicides, and/or fungicides, and/or plant growth regulators. Such mixtures, and the use of such mixtures to control weeds and/or undesired plant growth, form yet further aspects of the invention. For the avoidance of doubt, mixtures of invention also include mixtures of two or more different compounds of formula (I). In particular, the present invention also relates to a composition of the invention which comprises at least one further herbicide in addition to the compound of formula (I).

When a compound of formula (I) is combined with at least one additional herbicide, the following mixtures of the compound of formula (I) are preferred. Compound of formula (I)+acetochlor, compound of formula (I)+acifluorfen, compound of formula (I)+acifluorfen-sodium, compound of formula (I)+aclonifen, compound of formula (I)+acrolein, compound of formula (I)+alachlor, compound of formula (I)+alloxydim, compound of formula (I)+allyl alcohol, compound of formula (I)+ametryn, compound of formula (I)+amicarbazone, compound of formula (I)+amidosulfuron, compound of formula (I)+aminocyclopyrachlor, compound of formula (I)+aminopyralid, compound of formula (I)+amitrole, compound of formula (I)+ammonium sulfamate, compound of formula (I)+anilofos, compound of formula (I)+asulam, compound of formula (I)+atrazine, formula (I)+aviglycine, formula (I)+azafenidin, compound of formula (I)+azimsulfuron, compound of formula (I)+BCPC, compound of formula (I)+beflubutamid, compound of formula (I)+benazolin, formula (I)+bencarbazone, compound of formula (I)+benfluralin, compound of formula (I)+benfuresate, compound of formula (I)+bensulfuron, compound of formula (I)+bensulfuron-methyl, compound of formula (I)+bensulide, compound of formula (I)+bentazone, compound of formula (I)+benzfendizone, compound of formula (I)+ benzobicyclon, compound of formula (I)+benzofenap, compound of formula (I)+bicyclopyrone, compound of formula (I)+bifenox, compound of formula (I)+bilanafos, compound of formula (I)+bispyribac, compound of formula (I)+bispyribac-sodium, compound of formula (I)+borax, compound of formula (I)+bromacil, compound of formula (I)+bromobutide, formula (I)+bromophenoxim, compound of formula (I)+bromoxynil, compound of formula (I)+butachlor, compound of formula (I)+butafenacil, compound of formula (I)+butamifos, compound of formula (I)+butralin, compound of formula (I)+butroxydim, compound of formula (I)+butylate, compound of formula (I)+cacodylic acid, compound of formula (I)+calcium chlorate, compound of formula (I)+cafenstrole, compound of formula (I)+carbetamide, compound of formula (I)+carfentrazone, compound of formula (I)+carfentrazone-ethyl, compound of formula (I)+CDEA, compound of formula (I)+CEPC, compound of formula (I)+chlorflurenol, compound of formula (I)+chlorflurenol-methyl, compound of formula (I)+chloridazon, compound of formula (I)+chlorimuron, compound of formula (I)+chlorimuron-ethyl, compound of formula (I)+chloroacetic acid, compound of formula (I)+chlorotoluron, compound of formula (I)+chlorpropham, compound of formula (I)+chlorsulfuron, compound of formula (I)+chlorthal, compound of formula (I)+chlorthal-dimethyl, compound of formula (I)+cinidon-ethyl, compound of formula (I)+cinmethylin, compound of formula (I)+cinosulfuron, compound of formula (I)+cisanilide, compound of formula (I)+clethodim, compound of formula (I)+clodinafop, compound of formula (I)+clodinafop-propargyl, compound of formula (I)+clomazone, compound of formula (I)+clomeprop, compound of formula (I)+clopyralid, compound of formula (I)+cloransulam, compound of formula (I)+cloransulam-methyl, compound of formula (I)+CMA, compound of formula (I)+4-CPB, compound of formula (I)+CPMF, compound of formula (I)+4-CPP, compound of formula (I)+CPPC, compound of formula (I)+cresol, compound of formula (I)+cumyluron, compound of formula (I)+cyanamide, compound of formula (I)+cyanazine, compound of formula (I)+cycloate, compound of formula (I)+cyclosulfamuron, compound of formula (I)+cycloxydim, compound of formula (I)+cyhalofop, compound of formula (I)+cyhalofop-butyl, compound of formula (I)+2,4-D, compound of formula (I)+3,4-DA, compound of formula (I)+daimuron, compound of formula (I)+dalapon, compound of formula (I)+dazomet, compound of formula (I)+2,4-DB, compound of formula (I)+3,4-DB, compound of formula (I)+2,4-DEB, compound of formula (I)+desmedipham, formula (I)+desmetryn, compound of formula (I)+dicamba, compound of formula (I)+dichlobenil, compound of formula (I)+ortho-dichlorobenzene, compound of formula (I)+para-dichlorobenzene, compound of formula (I)+dichlorprop, compound of formula (I)+dichlorprop-P, compound of formula (I)+diclofop, compound of formula (I)+diclofop-methyl, compound of formula (I)+diclosulam, compound of formula (I)+difenzoquat, compound of formula (I)+difenzoquat metilsulfate, compound of formula (I)+diflufenican, compound of formula (I)+diflufenzopyr, compound of formula (I)+dimefuron, compound of formula (I)+dimepiperate, compound of formula (I)+dimethachlor, compound of formula (I)+dimethametryn, compound of formula (I)+dimethenamid, compound of formula (I)+dimethenamid-P, compound of formula (I)+dimethipin, compound of formula (I)+dimethylarsinic acid, compound of formula (I)+dinitramine, compound of formula (I)+dinoterb, compound of formula (I)+diphenamid, formula (I)+dipropetryn, compound of formula (I)+diquat, compound of formula (I)+diquat dibromide, compound of formula (I)+dithiopyr, compound of formula (I)+diuron, compound of formula (I)+DNOC, compound of formula (I)+3,4-DP, compound of formula (I)+DSMA, compound of formula (I)+EBEP, compound of formula (I)+endothal, compound of formula (I)+EPTC, compound of formula (I)+esprocarb, compound of formula (I)+ethalfluralin, compound of formula (I)+ethametsulfuron, compound of formula (I)+ethametsulfuron-methyl, formula (I)+ethephon, compound of formula (I)+ethofumesate, compound of formula (I)+ethoxyfen, compound of formula (I)+ethoxysulfuron, compound of formula (I)+etobenzanid, compound of formual (I)+fenoxaprop, compound of formula (I)+fenoxaprop-P, compound of formula (I)+fenoxaprop-ethyl, compound of formula (I)+fenoxaprop-P-ethyl, compound of formula (I)+fentrazamide, compound of formula (I)+ferrous sulfate, compound of formula (I)+flamprop-M, compound of formula (I)+flazasulfuron, compound of formula (I)+florasulam, compound of formula (I)+fluazifop, compound of formula (I)+fluazifop-butyl, compound of formula (I)+fluazifop-P, compound of formula (I)+fluazifop-P-butyl, formula (I)+fluazolate, compound of formula (I)+flucarbazone, compound of formula (I)+flucarbazone-sodium, compound of formula (I)+flucetosulfuron, compound of formula (I)+fluchloralin, compound of formula (I)+flufenacet, compound of formula (I)+flufenpyr, compound of formula (I)+flufenpyr-ethyl, formula (I)+flumetralin, compound of formula (I)+flumetsulam, compound of formula (I)+flumiclorac, compound of formula (I)+flumiclorac-pentyl, compound of formula (I)+flumioxazin, formula (I)+flumipropin, compound of formula (I)+fluometuron, compound of formula (I)+fluoroglycofen, compound of formula (I)+fluoroglycofen-ethyl, formula (I)+fluoxaprop, formula (I)+flupoxam, formula (I)+flupropacil, compound of formula (I)+flupropanate, compound of formula (I)+flupyrsulfuron, compound of formula (I)+flupyrsulfuron-methyl-sodium, compound of formula (I)+flurenol, compound of formula (I)+fluridone, compound of formula (I)+flurochloridone, compound of formula (I)+fluroxypyr, compound of formula (I)+flurtamone, compound of formula (I)+fluthiacet, compound of formula (I)+fluthiacet-methyl, compound of formula (I)+fomesafen, compound of formula (I)+foramsulfuron, compound of formula (I)+fosamine, compound of formula (I)+glufosinate, compound of formula (I)+glufosinate-ammonium, compound of formula (I)+glyphosate, compound of formula (I)+halauxifen, compound of formula (I)+halauxifen-methyl, compound of formula (I)+halosulfuron, compound of formula (I)+halosulfuron-methyl, compound of formula (I)+haloxyfop, compound of formula (I)+haloxyfop-P, compound of formula (I)+HC-252, compound of formula (I)+hexazinone, compound of formula (I)+imazamethabenz, compound of formula (I)+imazamethabenz-methyl, compound of formula (I)+imazamox, compound of formula (I)+imazapic, compound of formula (I)+imazapyr, compound of formula (I)+imazaquin, compound of formula (I)+imazethapyr, compound of formula (I)+imazosulfuron, compound of formula (I)+indanofan, compound of formula (I) and indaziflam, compound of formula (I)+iodomethane, compound of formula (I)+iodosulfuron, compound of formula (I)+iodosulfuron-methyl-sodium, compound of formula (I)+ioxynil, compound of formula (I) and ipfencarbazone, compound of formula (I)+isoproturon, compound of formula (I)+isouron, compound of formula (I)+isoxaben, compound of formula (I)+isoxachlortole, compound of formula (I)+isoxaflutole, formula (I)+isoxapyrifop, compound of formula (I)+karbutilate, compound of formula (I)+lactofen, compound of formula (I)+lenacil, compound of formula (I)+linuron, compound of formula (I)+MAA, compound of formula (I)+MAMA, compound of formula (I)+MCPA, compound of formula (I)+MCPA-thioethyl, compound of formula (I)+MCPB, compound of formula (I)+mecoprop, compound of formula (I)+mecoprop-P, compound of formula (I)+mefenacet, compound of formula (I)+mefluidide, compound of formula (I)+mesosulfuron, compound of formula (I)+mesosulfuron-methyl, compound of formula (I)+mesotrione, compound of formula (I)+metam, compound of formula (I)+metamifop, compound of formula (I)+metamitron, compound of formula (I)+metazachlor, compound of formula (I) and metazosulfuron, compound of formula (I)+methabenzthiazuron, formula (I)+methazole, a compound of formula (I) and methiozolin, compound of formula (I)+methylarsonic acid, compound of formula (I)+methyldymron, compound of formula (I)+methyl isothiocyanate, compound of formula (I)+metobenzuron, formula (I)+metobromuron, compound of formula (I)+metolachlor, compound of formula (I)+S-metolachlor, compound of formula (I)+metosulam, compound of formula (I)+metoxuron, compound of formula (I)+metribuzin, compound of formula (I)+metsulfuron, compound of formula (I)+metsulfuron-methyl, compound of formula (I)+MK-616, compound of formula (I)+molinate, compound of formula (I)+monolinuron, a compound of formula (I) and monosulfuron, a compound of formula (I) and monosulfuron-ester compound of formula (I)+MSMA, compound of formula (I)+naproanilide, compound of formula (I)+napropamide, compound of formula (I)+naptalam, formula (I)+NDA-402989, compound of formula (I)+neburon, compound of formula (I)+nicosulfuron, formula (I)+nipyraclofen, formula (I)+n-methyl glyphosate, compound of formula (I)+nonanoic acid, compound of formula (I)+norflurazon, compound of formula (I)+oleic acid (fatty acids), compound of formula (I)+orbencarb, compound of formula (I)+orthosulfamuron, compound of formula (I)+oryzalin, compound of formula (I)+oxadiargyl, compound of formula (I)+oxadiazon, compound of formula (I)+oxasulfuron, compound of formula (I)+oxaziclomefone, compound of formula (I)+oxyfluorfen, compound of formula (I)+paraquat, compound of formula (I)+paraquat dichloride, compound of formula (I)+pebulate, compound of formula (I)+pendimethalin, compound of formula (I)+penoxsulam, compound of formula (I)+pentachlorophenol, compound of formula (I)+pentanochlor, compound of formula (I)+pentoxazone, compound of formula (I)+pethoxamid, compound of formula (I)+petrolium oils, compound of formula (I)+phenmedipham, compound of formula (I)+phenmedipham-ethyl, compound of formula (I)+picloram, compound of formula (I)+picolinafen, compound of formula (I)+pinoxaden, compound of formula (I)+piperophos, compound of formula (I)+potassium arsenite, compound of formula (I)+potassium azide, compound of formula (I)+pretilachlor, compound of formula (I)+primisulfuron, compound of formula (I)+primisulfuron-methyl, compound of formula (I)+prodiamine, compound of formula (I)+profluazol, compound of formula (I)+profoxydim, formula (I)+prohexadione-calcium, compound of formula (I)+prometon, compound of formula (I)+prometryn, compound of formula (I)+propachlor, compound of formula (I)+propanil, compound of formula (I)+propaquizafop, compound of formula (I)+propazine, compound of formula (I)+propham, compound of formula (I)+propisochlor, compound of formula (I)+propoxycarbazone, compound of formula (I)+propoxycarbazone-sodium, compound of formula (I)+propyzamide, compound of formula (I)+prosulfocarb, compound of formula (I)+prosulfuron, compound of formula (I)+pyraclonil, compound of formula (I)+pyraflufen, compound of formula (I)+pyraflufen-ethyl, formula (I)+pyrasulfotole, compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyributicarb, compound of formula (I)+pyridafol, compound of formula (I)+pyridate, compound of formula (I)+pyriftalid, compound of formula (I)+pyriminobac, compound of formula (I)+pyriminobac-methyl, compound of formula (I)+pyrimisulfan, compound of formula (I)+pyrithiobac, compound of formula (I)+pyrithiobac-sodium, formula (I)+pyroxasulfone, formula (I)+pyroxulam, compound of formula (I)+quinclorac, compound of formula (I)+quinmerac, compound of formula (I)+quinoclamine, compound of formula (I)+quizalofop, compound of formula (I)+quizalofop-P, compound of formula (I)+quizalofop-ethyl, compound of formula (I)+quizalofop-P-ethyl, compound of formula (I)+rimsulfuron, compound of formula (I)+saflufenacil, compound of formula (I)+sethoxydim, compound of formula (I)+siduron, compound of formula (I)+simazine, compound of formula (I)+simetryn, compound of formula (I)+SMA, compound of formula (I)+sodium arsenite, compound of formula (I)+sodium azide, compound of formula (I)+sodium chlorate, compound of formula (I)+sulcotrione, compound of formula (I)+sulfentrazone, compound of formula (I)+sulfometuron, compound of formula (I)+sulfometuron-methyl, compound of formula (I)+sulfosate, compound of formula (I)+sulfosulfuron, compound of formula (I)+sulfuric acid, compound of formula (I)+tar oils, compound of formula (I)+2,3,6-TBA, compound of formula (I)+TCA, compound of formula (I)+TCA-sodium, formula (I)+tebutam, compound of formula (I)+tebuthiuron, formula (I)+tefuryltrione, compound of formula 1+tembotrione, compound of formula (I)+tepraloxydim, compound of formula (I)+terbacil, compound of formula (I)+terbumeton, compound of formula (I)+terbuthylazine, compound of formula (I)+terbutryn, compound of formula (I)+thenylchlor, compound of formula (I)+thiazafluron, compound of formula (I)+thiazopyr, compound of formula (I)+thifensulfuron, compound of formula (I)+thiencarbazone, compound of formula (I)+thifensulfuron-methyl, compound of formula (I)+thiobencarb, compound of formula (I)+tiocarbazil, compound of formula (I)+topramezone, compound of formula (I)+tralkoxydim, a compound of formula (I) and triafamone compound of formula (I)+tri-allate, compound of formula (I)+triasulfuron, compound of formula (I)+triaziflam, compound of formula (I)+tribenuron, compound of formula (I)+tribenuron-methyl, compound of formula (I)+tricamba, compound of formula (I)+triclopyr, compound of formula (I)+trietazine, compound of formula (I)+trifloxysulfuron, compound of formula (I)+trifloxysulfuron-sodium, compound of formula (I)+trifluralin, compound of formula (I)+triflusulfuron, compound of formula (I)+triflusulfuron-methyl, compound of formula (I)+trifop, compound of formula (I)+trifop-methyl, compound of formula (I)+trihydroxytriazine, compound of formula (I)+trinexapac-ethyl, compound of formula (I)+tritosulfuron, compound of formula (I)+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula (I) and 2-[[8-chloro-3,4-dihydro-4-(4-methoxyphenyl)-3-oxo-2-quinoxalinyl]carbonyl-1,3-cyclohexanedione and the compound of formula (I)+VX-573.

In particular, the following mixtures are important:

mixtures of a compound of formula (I) with an acetanilide (e.g. compound of formula (I)+acetochlor, compound of formula (I)+dimethenamid, compound of formula (I)+metolachlor, compound of formula (I)+S-metolachlor, or compound of formula (I)+pretilachlor) or with other inhibitors of VLCFAE (e.g. compound of formala (I)+pyroxasulfone);

mixtures of a compound of formula (I) with an HPPD inhibitor (e.g. compound of formula (I)+isoxaflutole, compound of formula (I)+mesotrione, compound of formula (I)+pyrasulfotole, compound of formula (I)+sulcotrione, compound of formula (I)+tembotrione, compound of formula (I)+topramezone, compound of formula (I) bicyclopyrone;

mixtures of a compound of formula (I) with a PSII inhibitor (e.g. compound of formula (I)+atrazine, or compound of formula (I)+terbuthylazine, compound of formula (I)+ametrin, compound of formula (I)+bromoxinyl);

mixtures of a compound of formula (I) with glyphosate;

mixtures of a compound of formula (I) with glufosinate-ammonium;

mixtures of a compound of formula (I) with a PPO inhibitor (e.g. compound of formula (I)+acifluorfen-sodium, compound of formula (I)+butafenacil, compound of formula (I)+carfentrazone-ethyl, compound of formula (I)+cinidon-ethyl, compound of formula (I)+flumioxazin, compound of formula (I)+fomesafen, compound of formula (I)+lactofen, or compound of formula (I)+SYN 523 ([3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester) (CAS RN 353292-31-6)).

Whilst two-way mixtures of a compound of formula (I) and another herbicide are explicitly disclosed above, the skilled man will appreciate that the invention extends to three-way, and further multiple combinations comprising the above two-way mixtures. In particular, the invention extends to:

mixtures of a compound of formula (I) with a PSII inhibitor and an HPPD inhibitor (e.g. compound of formula (I)+PSII inhibitor+isoxaflutole, compound of formula (I)+PSII inhibitor+mesotrione, compound of formula (I)+PSII inhibitor+pyrasulfotole, compound of formula (I)+PSII inhibitor+sulcotrione, compound of formula (I)+PSII inhibitor+tembotrione, compound of formula (I)+PSII inhibitor+topramezone, compound of formula (I)+PSII inhibitor+bicyclopyrone;

mixtures of a compound of formula (I) with glyphosate and an HPPD inhibitor (e.g. compound of formula (I)+glyphosate+isoxaflutole, compound of formula (I)+glyphosate+mesotrione, compound of formula (I)+glyphosate+pyrasulfotole, compound of formula (I)+glyphosate+sulcotrione, compound of formula (I)+glyphosate+tembotrione, compound of formula (I)+glyphosate+topramezone, compound of formula (I)+glyphosate+bicyclopyrone;

mixtures of a compound of formula (I) with glufosinate-ammonium and an HPPD inhibitor (e.g. compound of formula (I)+glufosinate-ammonium+isoxaflutole, compound of formula (I)+glufosinate-ammonium+mesotrione, compound of formula (I)+glufosinate-ammonium+pyrasulfotole, compound of formula (I)+glufosinate-ammonium+sulcotrione, compound of formula (I)+glufosinate-ammonium+tembotrione, compound of formula (I)+glufosinate-ammonium+topramezone, compound of formula (I)+glufosinate-ammonium+bicyclopyrone;

mixtures of a compound of formula (I) with a VLCFAE inhibitor and an HPPD inhibitor (e.g. compound of formula (I)+S-metolachlor+isoxaflutole, compound of formula (I)+S-metolachlor+mesotrione, compound of formula (I)+S-metolachlor+pyrasulfotole, compound of formula (I)+S-metolachlor+sulcotrione, compound of formula (I)+S-metolachlor+tembotrione, compound of formula (I)+S-metolachlor+topramezone, compound of formula (I)+S-metolachlor+bicyclopyrone, compound of formula (I)+acetochlor+isoxaflutole, compound of formula (I)+acetochlor+mesotrione, compound of formula (I)+acetochlor+pyrasulfotole, compound of formula (I)+acetochlor+sulcotrione, compound of formula (I)+acetochlor+tembotrione, compound of formula (I)+acetochlor+topramezone, compound of formula (I)+acetochlor+bicyclopyrone, compound of formula (I)+pyroxasulfone+isoxaflutole, compound of formula (I)+pyroxasulfone+mesotrione, compound of formula (I)+pyroxasulfone+pyrasulfotole, compound of formula (I)+pyroxasulfone+sulcotrione, compound of formula (I)+pyroxasulfone+tembotrione, compound of formula (I)+pyroxasulfone+topramezone, compound of formula (I)+pyroxasulfone+bicyclopyrone, Particularly preferred are mixtures of the compound of formula (I) with mesotrione, bicyclopyrone, isoxaflutole, tembotrione, topramezone, sulcotrione, pyrasulfotole, metolachlor, S-metolachlor, acetochlor, pretilachlor, pyroxasulfone, P-dimethenamid, dimethenamid, flufenacet, pethoxamid, atrazine, terbuthylazine, bromoxynil, metribuzin, amicarbazone, bentazone, ametryn, hexazinone, diuron, tebuthiuron, glyphosate, paraquat, diquat, glufosinate, acifluorfen-sodium, butafenacil, carfentrazone-ethyl, cinidon-ethyl, flumioxazin, fomesafen, lactofen, [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester.

The mixing partners of the compound of formula (I) may also be in the form of esters or salts, as mentioned e.g. in The Pesticide Manual, 14th Edition (BCPC), 2006. The reference to acifluorfen-sodium also applies to acifluorfen, the reference to dimethenamid also applies to dimethenamid-P, the reference to glufosinate-ammonium also applies to glufosinate, the reference to bensulfuron-methyl also applies to bensulfuron, the reference to cloransulam-methyl also applies to cloransulam, the reference to flamprop-M also applies to flamprop, and the reference to pyrithiobac-sodium also applies to pyrithiobac, etc.

The mixing ratio of the compound of formula (I) to the mixing partner is preferably from 1:100 to 1000:1.

The mixtures can advantageously be used in the above-mentioned formulations (in which case "active ingredient" relates to the respective mixture of compound of formula (I) with the mixing partner).

The compounds of formula (I) according to the invention can also be used in combination with one or more safeners. Likewise, mixtures of a compound of formula (I) according to the invention with one or more further active ingredients, in particular with one or more further herbicides, can also be used in combination with one or more safeners. The term "safener" as used herein means a chemical that when used in combination with a herbicide reduces the undesirable effects of the herbicide on non-target organisms, for example, a safener protects crops from injury by herbicides but does not prevent the herbicide from killing the weeds. Where a compound of formula (I) is combined with a safener, the following combinations of the compound of formula (I) and the safener are particularly preferred. Compound of formula (I)+AD 67 (MON 4660), compound of formula (I)+benoxacor, compound of formula (I)+cloquintocet-mexyl, compound of formula (I)+cyometrinil and a compound of formula (I)+the corresponding (Z) isomer of cyometrinil, compound of formula (I)+cyprosulfamide (CAS RN 221667-31-8), compound of formula (I)+dichlormid, compound of formula (I) and dicyclonon, compound of formula (I) and dietholate, compound of formula (I)+fenchlorazole-ethyl, compound of formula (I)+fenclorim, compound of formula (I)+flurazole, compound of formula (I)+fluxofenim, compound of formula (I)+furilazole and a compound of formula (I)+the corresponding R isomer or furilazome, compound of formula (I)+isoxadifen-ethyl, compound of formula (I)+mefenpyr-diethyl, compound of formula (I) and mephenate, compound of formula (I)+oxabetrinil, compound of formula (I)+naphthalic anhydride (CAS RN 81-84-5), compound of formula (I) and TI-35, compound of formula (I)+N-isopropyl-4-(2-methoxy-benzoylsulfamoyl)-benzamide (CAS RN 221668-34-4) and a compound of formula (I)+N-(2-methoxybenzoyl)-4-[(methylaminocarbonyl)amino]benzenesulfonamide. Particularly preferred are mixtures of a compound of formula (I) with benoxacor, a compound of formula (I) with cloquintocet-mexyl, a compound of formula (I)+cyprosulfamide and a compound of formula (I) with N-(2-methoxybenzoyl)-4-[(methylaminocarbonyl)amino]benzenesulfonamide.

The safeners of the compound of formula (I) may also be in the form of esters or salts, as mentioned e.g. in The Pesticide Manual, 14th Edition (BCPC), 2006. The reference to cloquintocet-mexyl also applies to cloquintocet and to a lithium, sodium, potassium, calcium, magnesium, aluminium, iron, ammonium, quaternary ammonium, sulfonium or phosphonium salt thereof as disclosed in WO02/34048 and the reference to fenchlorazole-ethyl also applies to fenchlorazole, etc.

Preferably the mixing ratio of compound of formula (I) to safener is from 100:1 to 1:10, especially from 20:1 to 1:1.

The mixtures can advantageously be used in the abovementioned formulations (in which case "active ingredient" relates to the respective mixture of compound of formula (I) and any further active ingredient, in particular a further herbicide, with the safener).

It is possible that the safener and a compound of formula (I) and one or more additional herbicide(s), if any, are applied simultaneously. For example, the safener, a compound of formula (I) and one or more additional herbicide(s), if any, might be applied to the locus pre-emergence or might be applied to the crop post-emergence. It is also possible that the safener and a compound of formula (I) and one or more additional herbicide(s), if any, are applied sequentially. For example, the safener might be applied before sowing the seeds as a seed treatment and a compound of formula (I) and one or more additional herbicides, if any, might be applied to the locus pre-emergence or might be applied to the crop post-emergence.

Preferred mixtures of a compound of formula (I) with further herbicides and safeners include:

Mixtures of a compound of formula (I) with S-metolachlor and a safener, particularly benoxacor.

Mixtures of a compound of formula (I) with isoxaflutole and a safener.

Mixtures of a compound of formula (I) with mesotrione and a safener.

Mixtures of a compound of formula (I) with sulcotrione and a safener.

Mixtures of a compound of formula (I) with tembotrione and a safener.

Mixtures of a compound of formula (I) with topramezone and a safener.

Mixtures of a compound of formula (I) with bicyclopyrone and a safener.

Mixtures of a compound of formula (I) with a PSII inhibitor and a safener.

Mixtures of a compound of formula (I) with a PSII inhibitor and isoxaflutole and a safener.

Mixtures of a compound of formula (I) with a PSII inhibitor and mesotrione and a safener.

Mixtures of a compound of formula (I) with a PSII inhibitor and sulcotrione and a safener.

Mixtures of a compound of formula (I) with a PSII inhibitor and tembotrione and a safener.

Mixtures of a compound of formula (I) with a PSII inhibitor and topramezone and a safener.

Mixtures of a compound of formula (I) with a PSII inhibitor and bicyclopyrone and a safener.

Mixtures of a compound of formula (I) with glyphosate and a safener.

Mixtures of a compound of formula (I) with glyphosate and isoxaflutole and a safener.

Mixtures of a compound of formula (I) with glyphosate and mesotrione and a safener.

Mixtures of a compound of formula (I) with glyphosate and sulcotrione and a safener.

Mixtures of a compound of formula (I) with glyphosate and tembotrione and a safener.

Mixtures of a compound of formula (I) with glyphosate and topramezone and a safener.

Mixtures of a compound of formula (I) with glyphosate and bicyclopyrone and a safener.

Mixtures of a compound of formula (I) with glufosinate-ammonium and a safener.

Mixtures of a compound of formula (I) with glufosinate-ammonium and isoxaflutole and a safener.

Mixtures of a compound of formula (I) with glufosinate-ammonium and mesotrione and a safener.

Mixtures of a compound of formula (I) with glufosinate-ammonium and sulcotrione and a safener.

Mixtures of a compound of formula (I) with glufosinate-ammonium and tembotrione and a safener.

Mixtures of a compound of formula (I) with glufosinate-ammonium and topramezone and a safener.

Mixtures of a compound of formula (I) with glufosinate-ammonium and bicyclopyrone and a safener.

Mixtures of a compound of formula (I) with S-metolachlor and a safener.

Mixtures of a compound of formula (I) with S-metolachlor and isoxaflutole and a safener.

Mixtures of a compound of formula (I) with S-metolachlor and mesotrione and a safener.

Mixtures of a compound of formula (I) with S-metolachlor and sulcotrione and a safener.

Mixtures of a compound of formula (I) with S-metolachlor and tembotrione and a safener.

Mixtures of a compound of formula (I) with S-metolachlor and topramezone and a safener.

Mixtures of a compound of formula (I) with S-metolachlor and bicyclopyrone and a safener.

Mixtures of a compound of formula (I) with pyroxasulfone and a safener.

Mixtures of a compound of formula (I) with pyroxasulfone and isoxaflutole and a safener.

Mixtures of a compound of formula (I) with pyroxasulfone and mesotrione and a safener.

Mixtures of a compound of formula (I) with pyroxasulfone and sulcotrione and a safener.

Mixtures of a compound of formula (I) with pyroxasulfone and tembotrione and a safener.

Mixtures of a compound of formula (I) with pyroxasulfone and topramezone and a safener.

Mixtures of a compound of formula (I) with pyroxasulfone and bicyclopyrone and a safener.

Mixtures of a compound of formula (I) with acetochlor and a safener.

Mixtures of a compound of formula (I) with acetochlor and isoxaflutole and a safener.

Mixtures of a compound of formula (I) with acetochlor and mesotrione and a safener.

Mixtures of a compound of formula (I) with acetochlor and sulcotrione and a safener.

Mixtures of a compound of formula (I) with acetochlor and tembotrione and a safener.

Mixtures of a compound of formula (I) with acetochlor and topramezone and a safener.

Mixtures of a compound of formula (I) with acetochlor and bicyclopyrone and a safener.

Various aspects and embodiments of the present invention will now be illustrated in more detail by way of example. It will be appreciated that modification of detail may be made without departing from the scope of the invention.

For the avoidance of doubt, where a literary reference, patent application, or patent, is cited within the text of this application, the entire text of said citation is herein incorporated by reference.

EXAMPLES

Preparation Examples

The following abbreviations were used in this section: s=singlet; bs=broad singlet; d=doublet; dd=double doublet; dt=double triplet; t=triplet; tt=triple triplet, q=quartet, sept=septet; m=multiplet; RT=retention time, MH$^+$=molecular mass of the molecular cation.

$^1$H NMR spectra were recorded at 400 MHz on a Varian Unity Inova instrument. LC-MS data was obtained using the following two methods:

Method A:

the compounds were analyzed using a Waters 2777 injector, 2996 photodiode array, 2420 ELSD and Micromass ZQ2000 equipped with a Waters Atlantis dC18 column (column length 20 mm, internal diameter of column 3 mm, particle size 3 micron). Solvent A: 0.05% trifluoroacetic acid in water (v/v); Solvent B: 0.05% trifluoroacetic acid in acetonitrile (v/v). The analysis was conducted using a three minute run time, according to the following gradient table:

| Time (min) | Solvent A (%) | Solvent B (%) | Flow (ml/min) |
|---|---|---|---|
| 0.00 | 95.0 | 5.0 | 1.300 |
| 2.50 | 0.0 | 100 | 1.300 |
| 2.80 | 0.00 | 100 | 1.300 |
| 2.90 | 95.0 | 5.0 | 1.300 |
| 3.00 | 95.0 | 5.0 | 1.300 |

Method B:

the compounds were analyzed using a Waters 2795 HPLC equipped with a Waters Atlantis dC18 column (column length 20 mm, internal diameter of column 3 mm, particle size 3 micron, temperature 40° C.), Waters photodiode array ESI Corona CAD detector and Micromass ZQ2000 MS. Standard MS conditions are ES+/−switching over mass range 130-950. Solvent A: 0.1% formic acid in water (v/v); Solvent B: 0.1% formic acid in acetonitrile (v/v). The analysis was conducted using a three minute run time, according to the following gradient table:

| Time (min) | Solvent A (%) | Solvent B (%) | Flow (ml/min) |
|---|---|---|---|
| 0.00 | 90.0 | 10.0 | 2.00 |
| 0.25 | 90.0 | 10.0 | 2.00 |
| 2.00 | 10.0 | 90.0 | 2.00 |
| 2.50 | 10.0 | 90.0 | 2.00 |
| 2.60 | 90.0 | 10.0 | 2.00 |
| 3.0 | 90.0 | 10.0 | 2.00 |

Example 1: Preparation of 3-chloro-4-ethyl-furan-2,5-dione

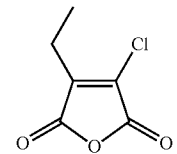

Step 1

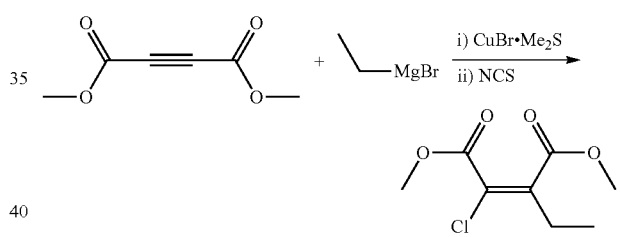

Under nitrogen, copper bromide dimethyl sulphide (1.234 g, 6 mM) was suspended in THF (30 ml) and stirred vigorously then cooled to −45° C. Ethyl magnesium bromide (2M in THF, 3 ml, 6 mM) was added dropwise maintaining the temperature below −45° C. after which the mixture was cooled to −78° C. Dimethyl acetylenedicarboxylate (0.62 ml, 5 mM) dissolved in THF (7.5 ml) was added dropwise maintain the temperature below −67° C. After 20 minutes at −78° C. the N-chloro succinimide (0.668 g, 5 mM) was added and stirring was continued at −78° C. for 90 minutes. The reaction was quenched by addition of saturated ammonium chloride solution and the mixture warmed to room temperature.

The aqueous fraction was separated off and extracted with 3×50 ml ethyl acetate, the combined organic fractions were washed with water (50 ml) and brine (50 ml) then dried over magnesium sulphate, filtered and evaporated down. The crude product was partially purified by chromatography to leave a mixture of the desired product and unreacted dimethyl acetylenedicarboxylate. The yield was assumed to be 100%.

$^1$H NMR (CDCl$_3$): δ 3.83 (3H, s); 3.81 (3H, s); 2.58 (2H, q); 1.12 (3H, t).

Step 2

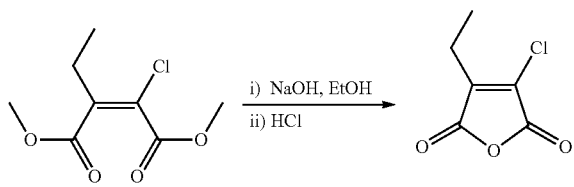

Dimethyl (E)-2-chloro-3-ethyl-but-2-enedioate (example 1, product step 1; assume 100% from previous reaction, 5 mM) was dissolved in ethanol (7.5 ml) and sodium hydroxide (2M soln., 9 ml, 18 mM) then stirred at room temperature for 18 hours. The reaction mixture was acidified with HCl (2M, 10 ml) and extracted with ethyl acetate (3×25 ml), the combined organics were dried over magnesium sulphate and the solvent removed to leave a brown oil. The crude product was carried on directly to the next stage of the synthesis and the yield was assumed to be 100%.

Example 2: Preparation of 3-bromo-2-hydroxy-4-methoxy-1,2-dihydropyrrol-5-one

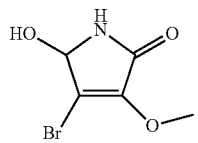

Step 1

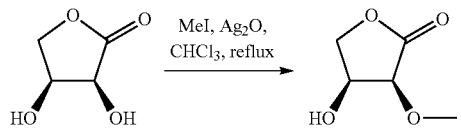

(3R,4R)-3,4-dihydroxytetrahydrofuran-2-one (2.00 g, 16.9 mM) was slurried in chloroform (25 mL). Silver (I) oxide (16.7 g, 71.1 mM) and iodomethane (24.0 g, 169 mM, 10.5 mL) were added and the mixture warmed to reflux with stirring under a nitrogen atmosphere for 45 minutes. The mixture was allowed to cool and was filtered through a bed of celite, washing through with further portions of chloroform. The filtrate was evaporated giving a colourless oil which was chromatographed to give (3R,4R)-4-hydroxy-3-methoxy-tetrahydrofuran-2-one as a colourless liquid which crystallised (0.956 g, 43%)

$^1$H NMR: (CDCl$_3$): δ 4.55 (m, 1H); 4.35 (dd, 1H); 4.30 (dd, 1H); 4.07 (d, 1H); 3.71 (s, 3H); 2.74 (s, 1H)
Step 2

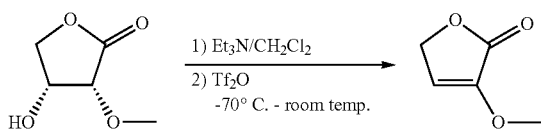

(3R,4R)-4-hydroxy-3-methoxy-tetrahydrofuran-2-one (0.35 g, 2.6 mM) was dissolved in dichloromethane (30 mL). Triethylamine (1.34 g, 13.3 mM, 1.85 mL) was added and the solution cooled to −70° C. Trifluoromethanesulfonic anhydride (1.1 g, 4.0 mM, 0.67 mL) was added drop-wise over a few minutes keeping the reaction temperature below −60° C. The mixture was stirred at −70° C. for 2 hours then allowed to warm to ambient temperature and stand overnight. The solvent was evaporated to produce a purple oil which was chromatographed to give 4-methoxy-2H-furan-5-one as a light brown crystalline solid (259 mg, 86%)

$^1$H NMR: (CDCl$_3$): δ 6.14 (t, 1H); 4.89 (d, 2H); 3.83 (s, 3H)
Step 3

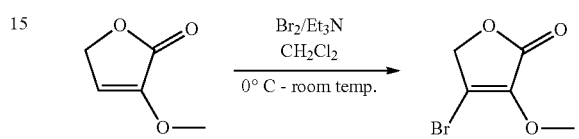

4-methoxy-2H-furan-5-one (0.584 g, 5.12 mM) was dissolved in dichloromethane (40 mL) and the solution cooled to 0-5° C. Bromine (0.818 g, 5.12 mM, 0.262 mL) was added drop-wise over 10 minutes. The mixture was stirred in the cold for 30 minutes, allowed to warm to room temperature and stirred for 1 hour. The mixture was cooled to 5° C. and triethylamine (0.570 g, 5.63 mM, 0.785 mL) was added drop-wise whereupon the reaction mixture de-colourised. The mixture was allowed to warm to room temperature and stirred for 3 hours. The mixture was washed with saturated brine (2×10 mL), dried over magnesium sulfate, filtered and the filtrate evaporated to produce a pale yellow oil which was chromatographed to give 3-bromo-4-methoxy-2H-furan-5-one as a white solid (0.428 g, 43%)

$^1$H NMR: (CDCl$_3$): δ 4.75 (s, 2H); 4.14 (s, 3H)
Step 4

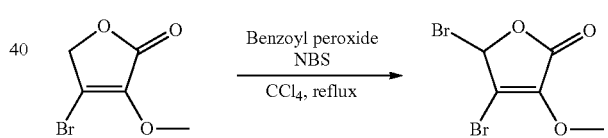

3-bromo-4-methoxy-2H-furan-5-one (0.428 g, 2.22 mmol) was dissolved in carbon tetrachloride (15 mL). N-bromosuccinimide (0.395 g, 2.22 mM) and benzoyl peroxide (0.002 g, 0.008 mM) were added and the mixture heated at reflux with stirring for 45 minutes then allowed to cool. The mixture was filtered and the filtrate evaporated to produce a yellow oil which was chromatographed to give 2,3-dibromo-4-methoxy-2H-furan-5-one as a pale yellow oil (0.44 g, 73%)

$^1$H NMR: (CDCl$_3$): δ 6.72 (s, 1H); 4.22 (s, 3H)
Step 5

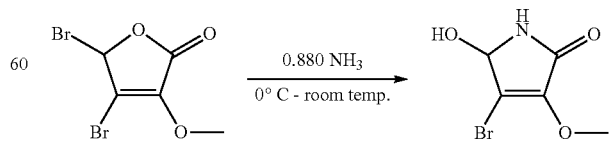

0.880 ammonia solution (8.8 g, 250 mM, 10 mL) was cooled to 5° C. 2,3-dibromo-4-methoxy-2H-furan-5-one (0.440 g, 1.62 mM) was added and the mixture stirred in the cold for 15 minutes. The mixture was allowed to warm to room temperature and stirred for 1 hour. The mixture was evaporated (keeping the flask temperature below 40° C.) producing a sticky yellow gum which was triturated with tetrahydrofuran and filtered. The filtrate was evaporated to give 3-bromo-2-hydroxy-4-methoxy-1,2-dihydropyrrol-5-one as a yellow gum (220 mg, 65%)

$^1$H NMR: (CDCl$_3$): δ 7.00 (s, 1H); 5.34 (d, 1H); 4.17 (s, 3H); 2.70 (s, 1H)

Example 3: Preparation of 3-ethoxy-4-methyl-furan-2,5-dione

Step 1

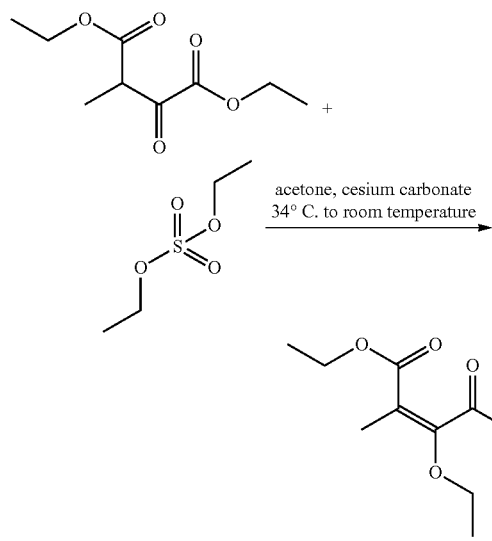

Cesium carbonate (20.43 g, 62.71 mM) was suspended in acetone (50 ml) with stirring at room temperature, then diethyl 2-methyl-3-oxo-butanedioate (12.68 g, 62.71 mM) was added all at once, washing in with acetone (5 ml). The reaction exothermed to 34° C., and there was very mild effervescence and a yellow colour developed. The reaction was stirred for 5 minutes, and reaction was now at 33° C. Diethyl sulfate (9.669 g, 62.71 mM) was added over 1 minute, resulting in no exotherm. The reaction was stirred and allowed to cool slowly to room temperature. The reaction was stirred at room temperature for 27 hours. Most of the acetone was evaporated, then water (100 ml) and dichloromethane (100 ml) were added, shaken, and the layers separated. The aqueous layer was extracted a further 2×50 ml dichloromethane, and the combined dichloromethane extracts were dried with Na$_2$SO$_4$ and filtered to give an amber oil (18.1 g) which was chromatographed to give a colourless oil (12.50 g, 93% pure so 80% yield)

$^1$H NMR (CDCl$_3$) 4.33 (q, 2H), 4.17 (q, 2H), 3.95 (q, 2H), 1.84 (s, 3H), 1.36 (t, 3H), 1.33 (t, 3H), 1.27 (t, 3H)

Step 2

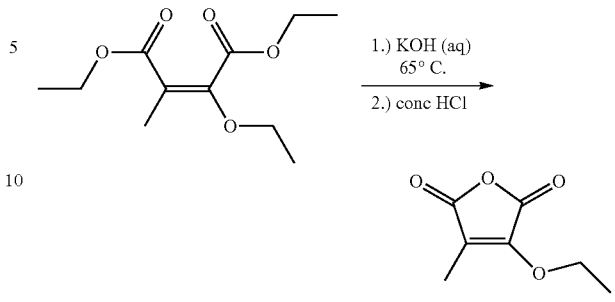

Diethyl (E)-2-ethoxy-3-methyl-but-2-enedioate (7.20 g, 31.3 mM) was dissolved in ethanol (9 ml) then 2N KOH (aq, 39 ml, 78 mM) was added and the reaction was heated at 65° C. with stirring for 2.5 hours. The reaction was cooled to 0° C. then was slowly acidified with concentrated hydrochloric acid (8 ml). The reaction was then extracted with 6 portions of EtOAc, (200 ml, 150 ml, then 4×100 ml) and the combined extracts were dried with Na$_2$SO$_4$, and filtered. The solvent was evaporated and the residue was azeotroped with dichloromethane to give a colourless liquid (3.15 g)

$^1$H NMR (CDCl$_3$) 1.44 (t, 3H), 2.02 s (s, 3H), 4.61 q (q, 2H)

Sample contained 30% ethyl acetate by mass so yield of 3-ethoxy-4-methyl-furan-2,5-dione was 45%

Example 4: Preparation of 2-chloro-4-(1-fluoro-1-methyl-ethyl)pyridine

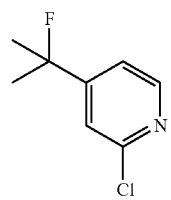

Step 1

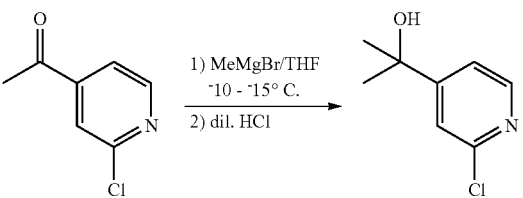

Methyl magnesium bromide solution (10 mL, 30 mM, 3.0M in diethyl ether) was dissolved in tetrahydrofuran (45 mL) with stirring under a nitrogen atmosphere, and the mixture cooled to around −15° C. A solution of 1-(2-chloro-4-pyridyl)ethanone (2.33 g, 15 mM) in tetrahydrofuran (15 mL) was added drop-wise keeping the reaction temperature below −10° C., and the mixture stirred in the cold for 20 minutes. 2N HCl (15 mL, 30 mM) was added slowly, and stirring was continued for an hour after the effervescence had subsided. 40 mL of the solvent was evaporated, and the mixture diluted with water (30 mL) and extracted with ethyl acetate (100, 50, 25 mL). The organic extracts were combined, washed with water, dried over magnesium sulfate, filtered and the filtrate evaporated giving a cloudy pale yellow oil which was chromatographed to give a colourless oil (2.17 g, 84%)

¹H NMR (CDCl₃): δ 8.32 (d, 1H); 7.46 (d, 1H); 7.30 (dd, 1H); 2.12 (s, 1H); 1.57 (s, 6H)

Step 2

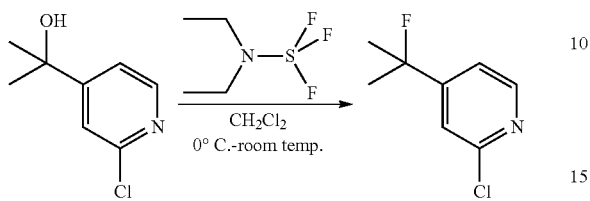

2-(2-chloro-4-pyridyl)propan-2-ol (1.03 g, 6 mM) was dissolved in dichloromethane (40 mL) and the solution chilled to 0-5° C. Diethylamino sulfurtrifluoride (2.42 g, 1.98 ml, 15 mM) was added drop-wise over 15 minutes, keeping the reaction temperature below 5° C. The solution was stirred in the cold for 2 hours, allowed to warm slowly to room temperature and stood overnight. The reaction mixture was gradually added to saturated sodium hydrogen carbonate solution (30 mL) and ice (100 mL), making sure that the pH of the solution was >7 at all times. After 30 minutes the mixture was diluted with dichloromethane (30 mL) and water (20 mL) and the organic phase separated. The aqueous phase was further extracted with dichloromethane (2×20 mL). The organic extracts were combined, washed with water, dried over magnesium sulfate, filtered and the filtrate evaporated giving a yellow-brown liquid which was chromatographed to give 2-chloro-4-(1-fluoro-1-methyl-ethyl)pyridine as a colourless liquid (0.686 g, 66%)

¹H NMR (CDCl₃): δ 8.37 (d, 1H); 7.33 (d, 1H); 7.19 (dd, 1H); 1.69 (s, 3H); 1.64 (s, 3H)

Example 5: Preparation of 2-chloro-4-(1,1-difluoroethyl)pyridine

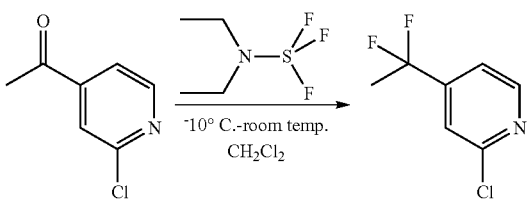

1-(2-chloro-4-pyridyl)ethanone (2.18 g, 14 mM) was dissolved in dichloromethane (40 mL) and the solution chilled to 0--10° C. Diethylamino sulfurtrifluoride (4.51 g, 3.7 mL, 28 mM) was added drop-wise over 10 minutes, keeping the reaction temp below −5° C. during the addition. The solution was stirred in the cold for 2 hours, allowed to warm slowly to room temperature and stood overnight. Further diethylamino sulfurtrifluoride (1.22 g, 1.0 mL, 7.57 mM) was added, and the mixture stirred for 3 hours. The reaction mixture was gradually added to saturated sodium hydrogen carbonate solution (30 mL) and ice (100 mL), making sure that the pH of the solution was >7 at all times. After 30 minutes the mixture was diluted with dichloromethane (30 mL) and water (20 mL) and the organic phase separated. The aqueous phase was further extracted with dichloromethane (2×20 mL). The organic extracts were combined, washed with water, dried over magnesium sulfate, filtered and the filtrate evaporated giving a bright orange liquid which was chromatographed to give 2-chloro-4-(1,1-difluoroethyl) pyridine as a colourless liquid (1.58 g, 64%).

¹H NMR (CDCl₃): δ 8.49 (d, 1H); 7.83 (dd, 1H); 7.45 (d, 1H); 1.91 (t, 3H)

Example 6: Preparation of 2-chloro-4-(1-fluoroethyl)pyridine

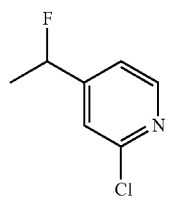

Step 1

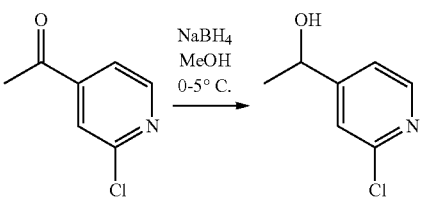

1-(2-chloro-4-pyridyl)ethanone (2.33 g, 15 mM) was dissolved in MeOH (100 mL) with stirring under a nitrogen atmosphere and the solution was cooled to around 0-5° C. Sodium borohydride (567 mg, 15 mM) was added in two portions over 5 minutes. The reaction mixture was stirred in the cold for 2 hours then allowed to warm to 10° C. Water (2 mL) was slowly added, then 80 mL of the solvent was evaporated. The mixture was diluted with ethyl acetate (30 ml) and the organic phase separated. The aqueous was further extracted with ethyl acetate (20 ml) and the organic extracts combined, washed with water (10 ml), dried over magnesium sulfate, filtered and the filtrate evaporated giving 1-(2-chloro-4-pyridyl)ethanol as a pale yellow oil (2.46 g, quantitative yield).

¹H NMR (CDCl₃): δ 8.31 (d, 1H); 7.37 (d, 1H); 7.21 (dd, 1H); 4.91 (dq, 1H); 2.43 (d, 1H); 1.50 (d, 3H)

Step 2

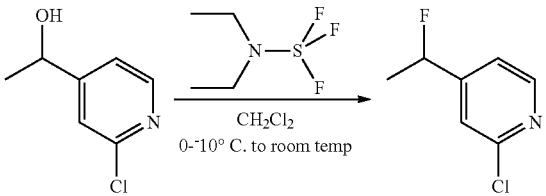

1-(2-chloro-4-pyridyl)ethanol (1.00 g, 6.35 mM) was dissolved in dichloromethane (30 mL) with stirring and the solution chilled to 0 to −10° C. The diethylamino sulfurtrifluoride (2.05 g, 1.68 mL, 12.69 mM) was added drop-wise over 10 minutes, keeping the reaction temp below −5° C. during the addition. The solution was stirred in the cold for 2 hours, allowed to warm slowly to room temperature and stood overnight. The reaction mixture was gradually added to saturated sodium hydrogen carbonate solution (30 mL) and ice (100 mL), making sure that the pH of the solution was >7 at all times. After 30 minutes the mixture was diluted with dichloromethane (30 mL) and water (20 mL) and the organic phase separated. The aqueous phase was further extracted with dichloromethane (2×20 mL). The organic extracts were combined, washed with water, dried over magnesium sulfate, filtered and the filtrate evaporated giving a green liquid which was chromatographed to give 2-chloro-4-(1-fluoroethyl)pyridine as a colourless liquid (720 mg, 71%).

$^1$H NMR (CDCl$_3$): δ 8.39 (d, 1H); 7.30 (d, 1H); 7.17 (dd, 1H); 5.60 (dq, 1H); 1.62 (dd, 3H)

Example 7: Preparation of 2-chloro-4-(difluoromethyl)pyridine

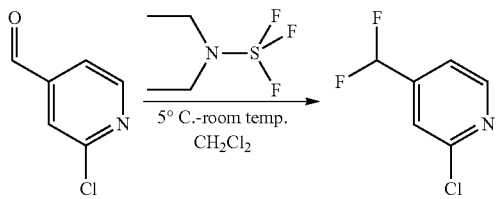

2-Chloropyridine-4-carbaldehyde (990 mg, 7.0 mM) was dissolved in dichloromethane (40 mL) with stirring and the solution cooled to 0-5° C. Diethylamino sulfurtrifluoride (2.82 g, 2.31 ml, 17.5 mM) was added drop-wise over 15 minutes, keeping the reaction temperature below 5° C. The solution was stirred in the cold for 2 hours, allowed to warm slowly to room temperature and stood overnight. The reaction mixture was gradually added to saturated sodium hydrogen carbonate solution (30 mL) and ice (100 mL), making sure that the pH of the solution was >7 at all times. After 30 minutes the mixture was diluted with dichloromethane (30 mL) and water (20 mL) and the organic phase separated. The aqueous phase was further extracted with dichloromethane (2×20 mL). The organic extracts were combined, washed with water, dried over magnesium sulfate, filtered and the filtrate evaporated giving a yellow liquid which was chromatographed to give 2-chloro-4-(difluoromethyl)pyridine as a colourless liquid (813 mg, 71%)

$^1$H NMR (CDCl$_3$): δ 8.54 (d, 1H); 7.81 (dd, 1H); 7.45 (d, 1H); 6.71 (t, 1H)

Example 8: Preparation of isopropyl 6-chloro-4-isopropyl-pyridine-3-carboxylate

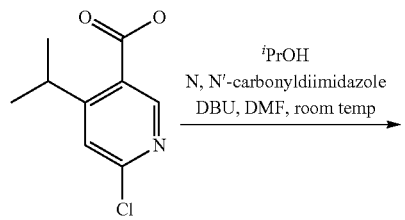

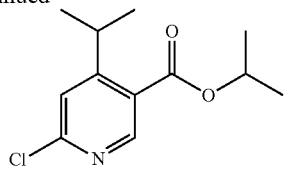

6-chloro-4-isopropyl-pyridine-3-carboxylic acid (1.00 g, 5.01 mM) was suspended in N,N-dimethylformamide (10 mL), and N,N'-carbonyldiimidazole (0.912 g, 5.51 mM) was added. The mixture was stirred at ambient temperature for 30 minutes. Isopropanol (0.452 g, 0.575 mL, 7.51 mM) and 1,8-diazabicyclo[5.4.0]undec-7-ene (1.14 g, 1.12 mL, 7.51 mM) were added. The mixture was stirred for 1 hour then allowed to stand at ambient temperature for 16 hours. The mixture was diluted with water (10 mL) and extracted with diethyl ether (3×20 mL). The organic extracts were combined, washed with water (2×10 mL), dried over magnesium sulfate, filtered and the filtrate evaporated giving a light brown liquid which was chromatographed to give isopropyl 6-chloro-4-isopropyl-pyridine-3-carboxylate as a colourless liquid (0.62 g, 51%)

$^1$H NMR (CDCl$_3$): δ 8.71 (s, 1H); 7.32 (s, 1H); 5.26 (m, 1H); 3.80 (m, 1H); 1.38 (d, 6H); 1.26 (d, 6H)

Example 9: Preparation of 5-(1-ethoxyvinyl)-4-(trifluoromethyl)pyridin-2-amine

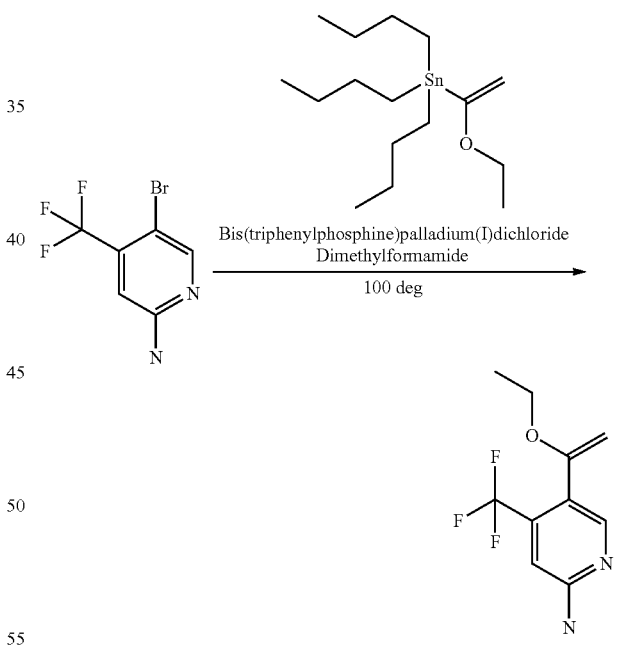

Bis(triphenylphosphine)palladium(II)dichloride (0.74 g, 1.0373 mmol) and 5-bromo-4-(trifluoromethyl)pyridin-2-amine (5 g, 20.75 mmol) were stirred in dimethylformamide (10 mL) under nitrogen and the tributyl(1-ethoxyvinyl) stannane (7.5 g, 20.75 mmol) was added. The mixture was heated to 80° C. for 2 h, then to 100 degrees for a further 2 h). The mixture was poured into saturated brine (250 mL) and was extracted with three portions of dichloromethane. The extracts were dried over anhydrous magnesium sulphate, and the solution was evaporated, giving an orange oil (4.0 g, 83%)

$^1$H NMR (CDCl$_3$) 8.19 (s, 1H); 6.70 (s, 1H); 4.77 (bs, 2H); 4.28 (d, 1H); 4.23 (d, 1H); 3.86 (q, 2H); 1.35 (t, 3H).

Example 10: Preparation of 1-[5-bromo-4-(trifluoromethyl)-2-pyridyl]-3-methoxy-4-methyl-pyrrole-2,5-dione

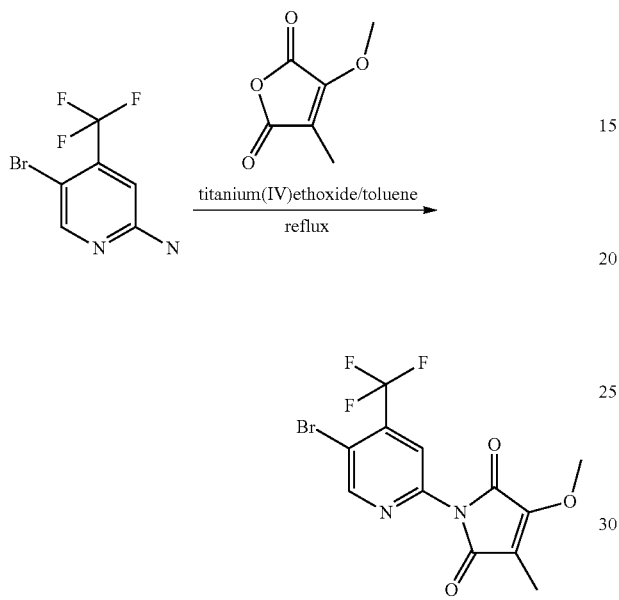

5-bromo-4-(trifluoromethyl)pyridin-2-amine (WO012044727) ((5 g, 20.7 mmol) and 3-methoxy-4-methyl-furan-2,5-dione (2.95 g, 20.7 mmol) were stirred in dry toluene (75 mL), and titanium(IV)ethoxide (2.37 g, 10.4 mmol) was added. The mixture was heated to reflux for 6 hours, then left to cool to ambient temperature for 15 hours. The entire reaction mixture was evaporated onto silica and the product isolated by chromatography, giving an orange solid (3.7 g, 49%)

$^1$H NMR CDCl$_3$ 8.85, (s, 1H); 7.68, (s, 1H); 4.27, (s, 3H) 2.07, (s, 3H).

Example 11: Preparation of 1-[5-bromo-4-(trifluoromethyl)-2-pyridyl]-2-hydroxy-3-methoxy-4-methyl-2H-pyrrol-5-one (AD31)

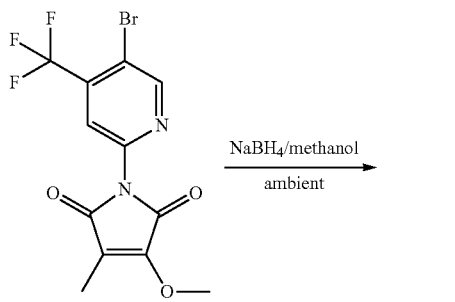

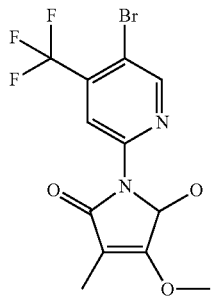

1-[5-bromo-4-(trifluoromethyl)-2-pyridyl]-3-methoxy-4-methyl-pyrrole-2,5-dione (1.0 g, 2.74 mmol) was stirred in methanol (50 mL) at ambient temperature, and sodium borohydride (0.075 g, 1.9 mmol) was added and the mixture was stirred for 1 hour. The solution was diluted with water and adjusted to pH5 with 10% (v/v) aqueous hydrochloric acid, then was extracted with three portions of dichloromethane. The combined extracts were dried over anhydrous magnesium sulphate, then the solvent was evaporated to give a white solid. (0.94 g, 93%).

$^1$H NMR CDCl$_3$ 8.77, (s, 1H); 8.50, (s, 1H); 6.13 (, d, 1H); 4.95, (d, 1H); 4.18, (s, 3H); 1.91, (s, 3H)

Example 12: Preparation of 3-bromo-2-hydroxy-4-methoxy-1-[4-(trifluoromethyl)-2-pyridyl]-2H-pyrrol-5-one (AE1)

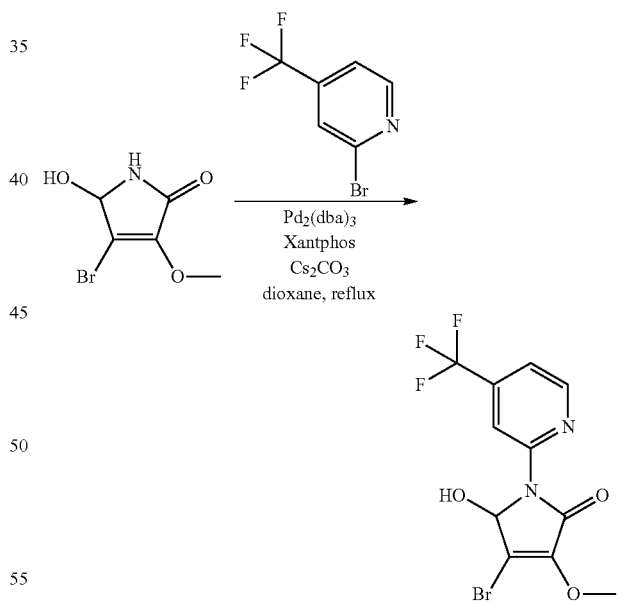

Tris(dibenzylideneacetone)dipalladium(0) (0.014 g, 0.015 mM), xantphos (0.034 g, 0.056 mM) and 2-bromo-4-(trifluoromethyl)pyridine (0.085 g, 0.38 mM) were stirred in 1,4-dioxane (3 mL). The mixture was stirred at room temperature for 10 minutes, then cesium carbonate (0.31 g, 0.94 mM) and 3-bromo-2-hydroxy-4-methoxy-1,2-dihydropyrrol-5-one (0.094 g, 0.45 mM) were added. The mixture was heated at reflux with stirring for 2.5 hours. The mixture was allowed to cool to room temperature and 3 mL solvent evaporated producing a dark brown gum which was chromatographed to give 3-bromo-2-hydroxy-4-methoxy-1-[4-(trifluoromethyl)-2-pyridyl]-2H-pyrrol-5-one (AE1) as an off-white solid (9 mg, 7%)

¹H NMR: (CDCl₃): δ 8.58 (s, 1H); 8.49 (d, 1H); 7.31 (dd, 1H); 6.13 (d, 1H); 5.21 (d, 1H); 4.25 (s, 3H)

Example 13: Preparation of 2-hydroxy-3-methoxy-4-methyl-1-[5-(2-methylprop-1-enyl)-4-(trifluoromethyl)-2-pyridyl]-2H-pyrrol-5-one (AD21)

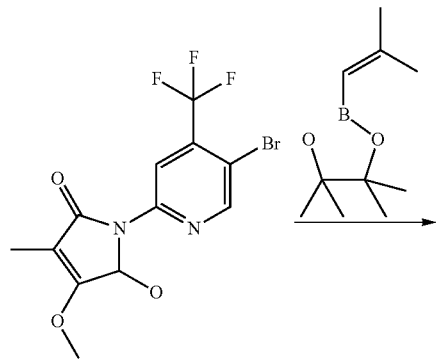

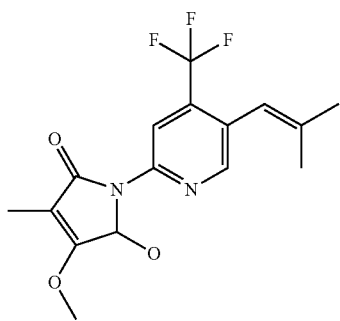

1-[5-bromo-4-(trifluoromethyl)-2-pyridyl]-2-hydroxy-3-methoxy-4-methyl-2H-pyrrol-5-one (200 mg, 0.54478 mmol) 4,4,5,5-tetramethyl-2-(2-methylprop-1-enyl)-1,3,2-dioxaborolane (140 mg, 0.7688 mmol), [1,1'-bis(diphenylphosphino)ferrocene]dichloropalladium(II) (0.05 equiv., 0.027 mmol), caesium fluoride (2 equiv., 1.09 mmol) were charged to a vial and water (1 mL) and dioxane (3 mL) were added. The reaction mixture was deoxygenated with nitrogen for 10 min and then sealed and microwaved at 150° C. for 15 mins. The reaction mixture was evaporated to dryness, redissolved in methanol, evaporated onto silica and the product isolated by chromatography;

130 mg (70%)

¹H NMR (400 MHz, Chloroform) δ ppm 8.63 (s, 1H) 8.16 (s, 1H) 6.23 (br. s., 1H) 6.15 (d, 1H) 5.33 (d, 1H) 4.13-4.19 (m, 3H) 4.16 (s, 3H) 1.92 (d, 6H) 1.72 (s, 3H)

Example 14: Preparation of 2-hydroxy-1-(4-isobutyl-2-pyridyl)-3-methoxy-4-methyl-2H-pyrrol-5-one (AD41)

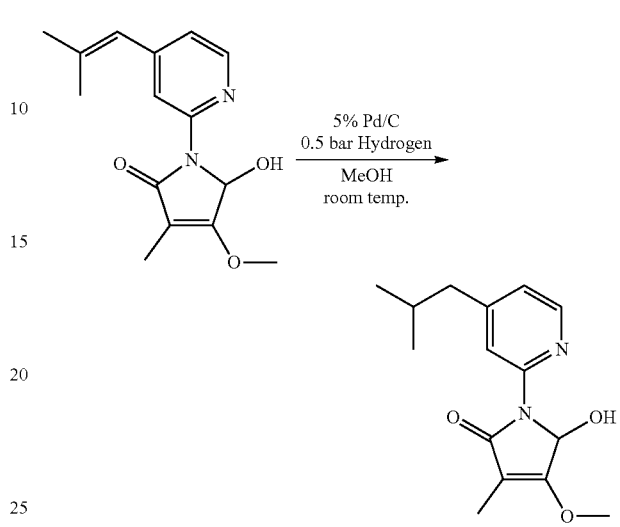

5% Palladium on activated carbon (0.015 g, 0.0070 mM) was charged to a hydrogenation vessel containing a magnetic stirrer bar, and the vessel flushed with nitrogen. 2-hydroxy-3-methoxy-4-methyl-1-[4-(2-methylprop-1-enyl)-2-pyridyl]-2H-pyrrol-5-one (0.0618 g, 0.225 mM) was dissolved in methanol (2 mL) and the solution added to the vessel. The mixture was stirred under hydrogen (0.5 bar pressure) for 3.5 hours, purged with nitrogen and filtered through a pad of celite, washing the filter cake with small portions of methanol. The filtrate was evaporated under reduced pressure to produce a grey oil which was chromatographed (reverse phase) to give 2-hydroxy-1-(4-isobutyl-2-pyridyl)-3-methoxy-4-methyl-2H-pyrrol-5-one (AD41) as a pale yellow gum (48 mg, 77%)

¹H NMR (CDCl₃): δ11.60 (s, 1H); 8.26 (s, 1H); 8.12 (d, 1H); 7.14 (dd, 1H); 6.46 (s, 1H); 4.16 (s, 3H); 2.67 (d, 2H); 2.01 (m, 1H); 1.83 (s, 3H); 0.96 (dd, 6H)

Example 15: Preparation of 6-(2-hydroxy-3-methoxy-4-methyl-5-oxo-2H-pyrrol-1-yl)-4-(trifluoromethyl)pyridine-3-carbonitrile (AD26)

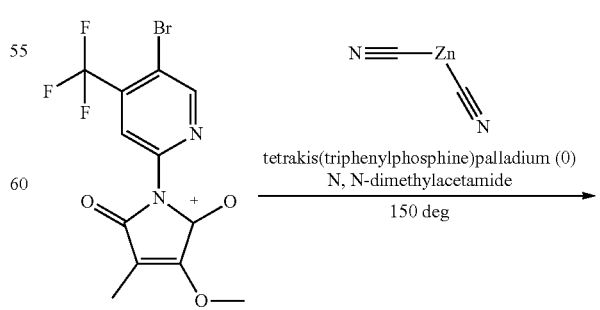

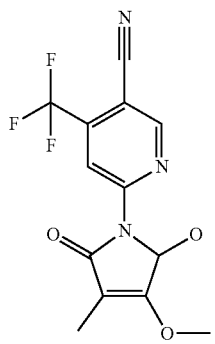

1-[5-bromo-4-(trifluoromethyl)-2-pyridyl]-2-hydroxy-3-methoxy-4-methy-2H-prro-5-one (100 mg, 0.27 mmol, zinc cyanide (0.066 g 0.56 mmol), tetrakis(triphenylphosphine)palladium(0) (0.047 g 0.041 mmol) were weighed into a vial and the dimethylacetamide (2.5 mL) was added. Mixture had nitrogen bubbled through for 15 minutes then was microwaved at 150° C. for 15 mins. The reaction mixture was poured into dilute aqueous sodium hydrogen carbonate solution and was extracted with 2 portions of dichloromethane. The extracts were dried on MgSO4 and evaporated onto silica. The product isolated by chromatography.

35 mg (40%)

$^1$H NMR (400 MHz, Chloroform) δ ppm 8.86 (s, 8H) 8.70 (s, 1H) 6.20 (dd, 1H) 4.79 (d, 1H) 4.19 (s, 3H) 1.91 (s, 3H)

Example 16: Preparation of 2-hydroxy-3-methoxy-4-methyl-1-[4-(trifluoromethyl)-5-(2-trimethylsilyl-ethynyl)-2-pyridyl]-2H-pyrrol-5-one

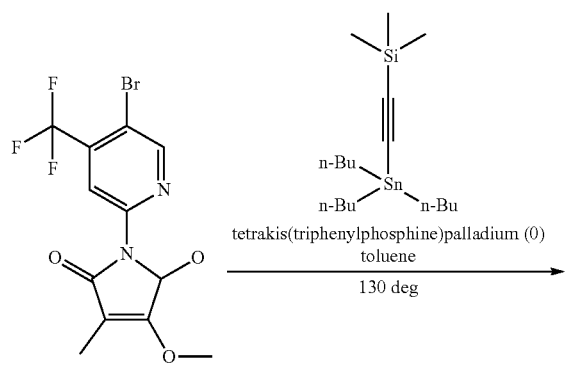

1-[5-bromo-4-(trifluoromethyl)-2-pyridyl]-2-hydroxy-3-methoxy-4-methyl-2H-pyrrol-5-one (0.28 g, 0.76 mmol) was dissolved in toluene (5 mL), tetrakis(triphenylphosphine)palladium(0) (0.023 mmol, 0.0265 g) was added. The reaction mixture was deoxygenated by bubbling nitrogen through for 15 mins, then trimethyl(2-tributylstannylethynyl)silane (0.91523 mmol, 0.3545 g, 0.341 mL) was added.

The reaction mixture was heated in the microwave to 130° C. for 30 mins.

The entire reaction mixture was evaporated onto silica and the product isolated by chromatography to give a pale yellow solid, 195 mg (67%)

pmr (CDCl$_3$) 8.6 (s, 1H); 8.38 (s, 1H); 6.1 (m, 1H); 5.01 (d, 1H); 4.09 (s, 3H); 1.81 (s, 3H); 0.19 (s, 9H)

Example 17: Preparation of 2-hydroxy-3-methoxy-4-methyl-1-[5-methylsulfanyl-4-(trifluoromethyl)-2-pyridyl]-2H-pyrrol-5-one (AD14)

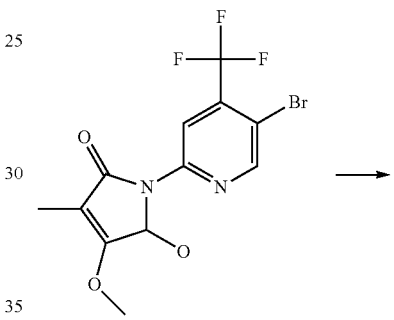

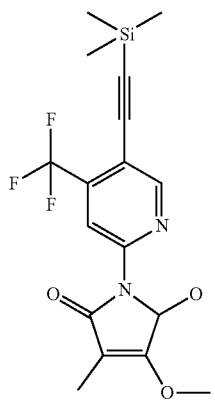

The 1-[5-bromo-4-(trifluoromethyl)-2-pyridyl]-2-hydroxy-3-methoxy-4-methyl-2H-pyrrol-5-one (0.20 g, 0.54 mmol) sodium thiomethoxide (0.045 g, 0.6 mmol) xantphos (0.032 g, 0.054 mmol) cesium carbonate (0.355 g, 1.09 mmol) and bis(3,5,3',5'-dimethoxydibenzylideneacetone)palladium(0) (0.023 g, 0.027 mmol) were weighed into a microwave vial and the dioxane was added. Deoxygenated by bubbling nitrogen through for 15 mins, then sealed and microwaved at 120° C. for 50 mins. The mixture was filtered and the filtrated evaporated onto silica. The product was purified by chromatography.

7 mg (4%)

$^1$H NMR (500 MHz, Chloroform) δ ppm 8.62 (s, 1H) 8.31 (s, 1H) 6.07 (br. s., 1H) 5.05 (d, 1H) 4.09 (s, 3H) 2.44 (s, 3H) 1.83 (s, 3H)

Example 18: Preparation of 2-hydroxy-3-methoxy-1-[5-methoxy-4-(trifluoromethyl)-2-pyridyl]-4-methyl-2H-pyrrol-5-one (AD10)

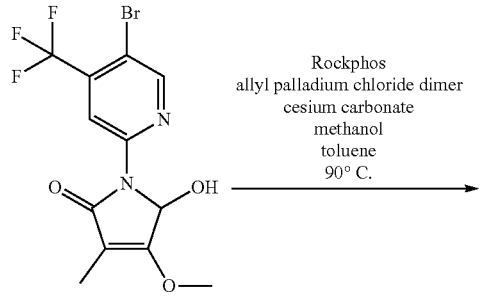

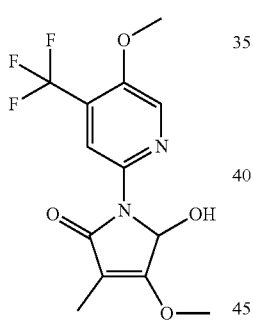

Ditert-butyl-[6-methoxy-3-methyl-2-(2,4,6-triisopropylphenyl)phenyl]phosphane (Rockphos, 8 mg, 0.0165 mM) and 2,4-diallyl-1$l^{3}$,3$l^{3}$-dichlora-2$l^{3}$,4$l^{3}$-dipalladacyclobutane (allyl palladium chloride dimer, 2 mg, 0.0055 mM) and cesium carbonate (269 mg, 0.825 mM) were suspended in toluene (0.8 ml) then degassed by bubbling nitrogen through for 5 minutes. The reaction was heated at 90° C. with stirring for 3 minutes then methanol (0.067 ml, 1.65 mM) and 1-[5-bromo-4-(trifluoromethyl)-2-pyridyl]-2-hydroxy-3-methoxy-4-methyl-2H-pyrrol-5-one (202 mg, 0.550 mM) were added and the reaction was heated at 90° C. with stirring in a sealed tube for 65 minutes. The reaction was cooled to room temperature, diluted with ethyl acetate (10 ml), then filtered through celite and the filtrate was evaporated to give a glassy solid (183 mg) which was chromatographed to give a white solid (90 mg, 51%)

$^1$H NMR (CDCl$_3$) 8.62 (s, 1H), 8.06 (s, 1H), 6.10 (s, 1H), 4.15 (s, 3H), 3.97 (s, 1H), 1.90 (s, 3H) melting point 136-140° C.

Example 19: Preparation of 1-[5-acetyl-4-(trifluoromethyl)-2-pyridyl]-2-hydroxy-3-methoxy-4-methyl-2H-pyrrol-5-one (AD2)

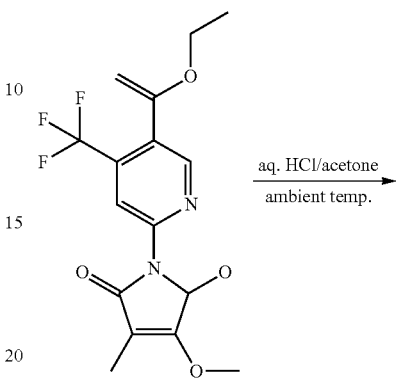

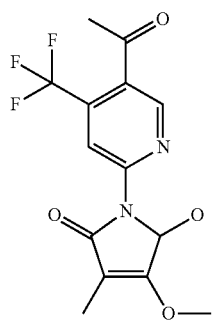

1-[5-(1-ethoxyvinyl)-4-(trifluoromethyl)-2-pyridyl]-2-hydroxy-3-methoxy-4-methyl-2H-pyrrol-5-one (3.2 g, 8.9 mmol, prepared as described in example 9) was dissolved in acetone (45 mL) at ambient temperature, and 10% v/v aq HCl (5 mL) was added. The reaction mixture was stirred for 2 hours. The mixture was then basified with saturated aqueous sodium bicarbonate, then the acetone was evaporated. The residue was extracted with 4 portions of dichloromethane, the extracts dried (MgSO$_4$) and evaporated to give 2.4 g of a pale yellow solid, (82%)

$^1$H NMR (CDCl$_3$): 8.78 (s, 1H); 8.57 (s, 1H); 6.18-6.19 (d, 1H); 5.04-5.05 (d, 1 h); 4.18 (s, 3H); 2.61 (s, 3H); 1.91 (s, 3H).

Example 20: Preparation of (E)-3-[6-(2-hydroxy-3-methoxy-4-methyl-5-oxo-2H-pyrrol-1-yl)-4-(trifluoromethyl)-3-pyridyl]but-2-enenitrile (AD38) and (Z)-3-[6-(2-hydroxy-3-methoxy-4-methyl-5-oxo-2H-pyrrol-1-yl)-4-(trifluoromethyl)-3-pyridyl]but-2-enenitrile (AD58)

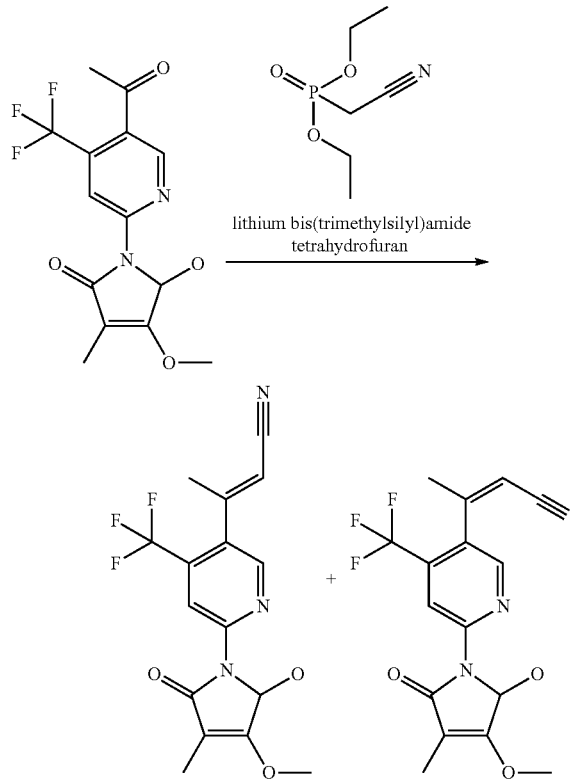

Tetrahydrofuran (10 mL) was stirred on a dry-ice/acetone bath under nitrogen and the lithium bis(trimethylsilyl)amide (1 mol/L) in Hexanes (1.2 mL, 1.2 mmol) was added, followed by the 2-diethoxyphosphorylacetonitrile (0.21 g, 1.2 mmol). Stirring continued in the cold for 1 h The 1-[5-acetyl-4-(trifluoromethyl)-2-pyridyl]-2-hydroxy-3-methoxy-4-methyl-2H-pyrrol-5-one (360 mg, 1.090 mmol, prepared as described in example 19) was dissolved in tetrahydrofuran (10 ml) and was added to the reaction over 5 mins, then cooling removed and the mixture left to warm to ambient temperature overnight. The reaction mixture was poured into saturated brine and extracted with 3 portions of dichloromethane (in the first extraction, organic was upper phase). The combined extracts were washed with brine, dried (MgSO4) and evaporated to give 460 mg of a yellow oil which was purified and isomers separated by chromatography to give 110 mg (28%) of a white solid, E-isomer $^1$H NMR (400 MHz, Chloroform) δ ppm 8.74 (s, 1H) 8.16 (s, 1H) 6.16 (s, 1H) 5.35 (d, J=1.21 Hz, 1H) 5.02 (br. s., 1H) 4.17 (s, 3H) 2.40 (s, 3H) 1.90 (s, 3H)

and 35 mg (9%) of a white solid, Z-isomer $^1$H NMR (400 MHz, Chloroform) δ ppm 8.78 (s, 1H) 8.19 (s, 1H) 6.17 (s, 1H) 5.64 (d, 1H) 5.08 (br. s., 1H) 4.16 (s, 3H) 2.24 (s, 3H) 1.90 (s, 3H)

Example 21: Preparation of 1-(5-tert-butylpyridazin-3-yl)-2-hydroxy-3-methoxy-4-methyl-2H-pyrrol-5-one (BD1)

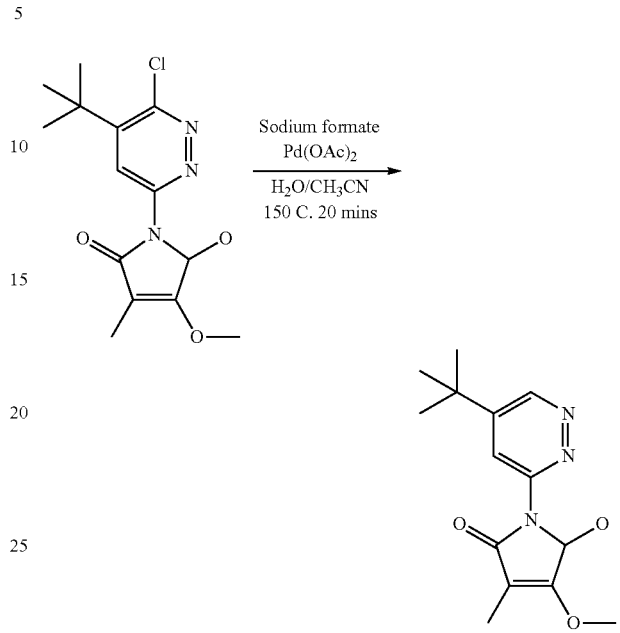

1-(5-tert-butyl-6-chloro-pyridazin-3-yl)-2-hydroxy-3-methoxy-4-methyl-2H-pyrrol-5-one (0.21 g, 0.67 mmol) can be prepared as described in example 12 from 4-tert-butyl-3,6-dichloro-pyridazine (which in turn is described in U.S. Pat. No. 4,791,110 1988). It is then mixed with sodium formate (93 mg, 1.35 mmol) and palladium acetate (0.30 mg, 0.0013 mmol) in acetonitrile (3 mL) and water (0.5 mL). The mixture was heated with stirring in a microwave at 150° C. for 20 minutes and then extracted with ethyl acetate×3, combined and washed with water and dried over magnesium sulphate. The solvent was evaporated to give a yellow gum which was chromatographed to give a pale yellow solid (60 mg, 30%)

Example 22: Preparation of 2-hydroxy-4-methoxy-3-methyl-1-[4-(trifluoromethyl)-2-pyridyl]-2H-pyrrol-5-one (AD42)

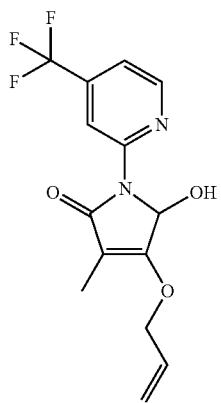

Step 1

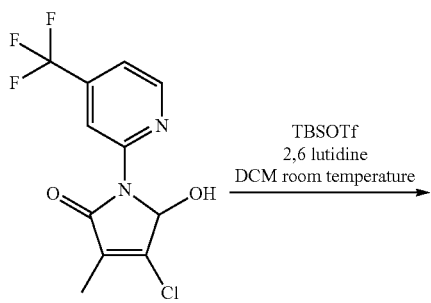

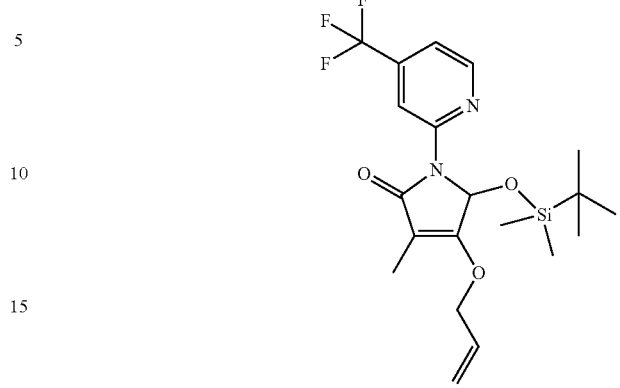

3-chloro-2-hydroxy-4-methyl-1-[4-(trifluoromethyl)-2-pyridyl]-2H-pyrrol-5-one (1 g, 3.42 mM) was suspended in dichloromethane (20 ml) and cooled to 0° C. with stirring. 2,6 lutidine (0.438 ml, 3.76 mM) was added, followed by dropwise addition of TBSOTf (0.824 ml, 3.59 mM), and the reaction was allowed to warm to room temperature. After 75 minutes a further 2,6 lutidine (0.120 ml, 1.025 mM) and TBSOTf (0.236 ml, 1.025 mM) was added and the reaction was stirred at room temperature for 18 hours. Water (15 ml) was added and shaken, then the DCM layer was removed and the water layer was extracted with a further 2×20 ml dichloromethane. The combined dichloromethane extracts were dried with $Na_2SO_4$, filtered and the filtrate was evaporated to give a beige solid (1.34 g) which was chromatographed to give a white solid (1.22 g, 83%)

$^1$H NMR (CDCl$_3$) 8.52 (d, 1H), 8.39 (d, 1H), 7.27 (dd, 1H), 6.42 (m, 1H), 1.96 (s, 3H), 0.81 (s, 9H), 0.25 (s, 3H), 0.01 (s, 3H)

Step 2

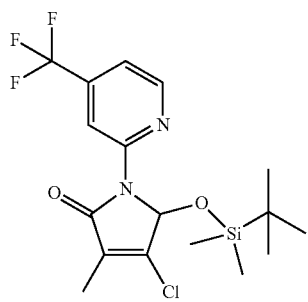

Allyl alcohol (0.241 ml, 3.539 mM) and 2-[tert-butyl(dimethyl)silyl]oxy-3-chloro-4-methyl-1-[4-(trifluoromethyl)-2-pyridyl]-2H-pyrrol-5-one (600 mg, 1.475 mM) were dissolved in DMSO (2 ml) and THF (2 ml) and stirred at room temperature, then potassium tert-butoxide (KOtBu, 1M in THF, 1.475 ml, 1.475 mM) was added slowly via a syringe pump at room temperature over 92 minutes. The reaction was stirred at room temp for a further 10 minutes. The reaction was poured into diethyl ether (30 ml) and brine (15 ml) and shaken. The layers were separated and the aqueous layer was extracted a further 2×15 ml diethyl ether. The combined ether layers were dried with $Na_2SO_4$, filtered and the filtrate was evaporated to give a brown gum (710 mg) which was chromatographed to give a white solid (150 mg, 24%)

$^1$H NMR (CDCl$_3$) 8.48 (d, 1H), 8.46 (d, 1H), 7.18 (dd, 1H), 6.36 (s, 1H), 6.02 (m, 1H), 5.38 m (m, 2H), 4.89 (m, 2H), 1.94 (s, 3H), 0.81 (s, 9H), 0.10 (s, 3H), 0.04 (s, 3H)

Melting point 63-67° C.

Step 3

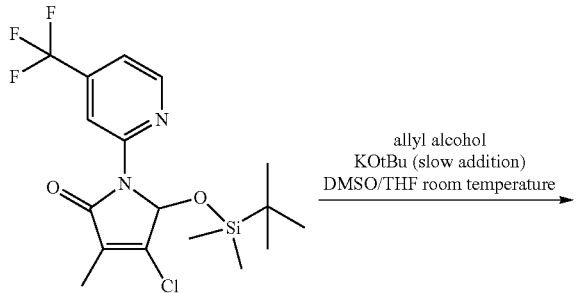

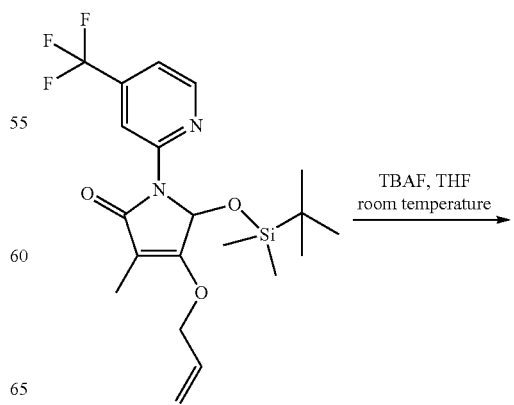

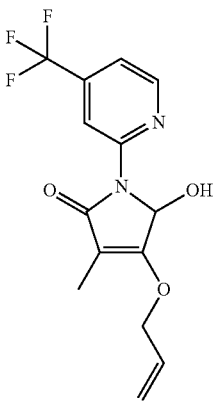 [SMILES: C=CCOC1=C(C)C(=O)N(c2cc(C(F)(F)F)ccn2)C1O]

3-allyloxy-2-[tert-butyl(dimethyl)silyl]oxy-4-methyl-1-[4-(trifluoromethyl)-2-pyridyl]-2H-pyrrol-5-one (85 mg, 0.198 mM) was dissolved in dry THF (0.70 ml) then tetrabutylammonium fluoride (TBAF, 1M in THF, 0.198 ml, 0.198 mM) was added and the reaction was stirred at room temperature. After 10 minutes, dichloromethane (10 ml) and water (5 ml) were added, shaken vigorously and the layers were separated. The aqueous layer was extracted a further 2×5 ml dichloromethane, and the combined extracts were dried with $Na_2SO_4$ and filtered. The filtrate was evaporated and the residue was chromatographed to give a white solid (60 mg, 96%).

$^1$H NMR ($CDCl_3$) 8.66 (d, 1H), 8.40 (d, 1H), 7.20 (dd, 1H), 6.18 (m, 1H), 6.04 (m, 1H), 5.38 (m, 2H), 5.32 m (m, 1H), 4.93 (m, 2H), 1.88 (s, 3H)

Melting point 97-102° C.

Example 23: Preparation of 2-hydroxy-4-methyl-3-(2,2,2-trifluoroethoxy)-1-[4-(trifluoromethyl)-2-pyridyl]-2H-pyrrol-5-one (AD44)

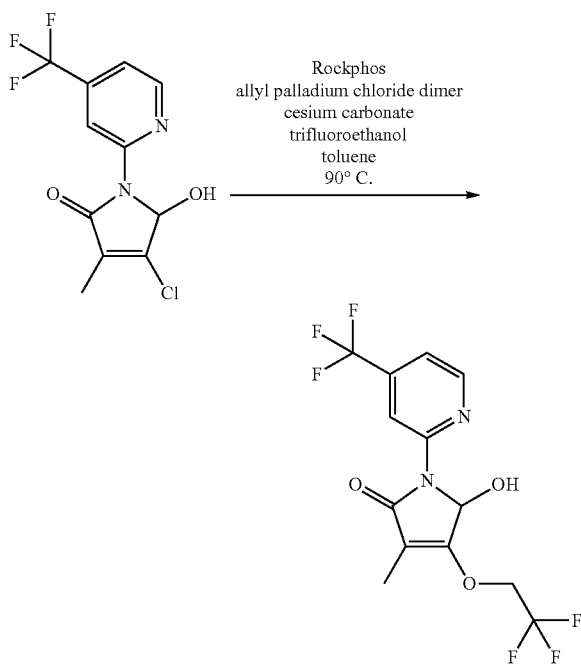

Ditert-butyl-[6-methoxy-3-methyl-2-(2,4,6-triisopropylphenyl)phenyl]phosphane (Rockphos, 8 mg, 0.0165 mM) and bis(allyl)di-p-chloro-dipalladium(II) (allyl palladium chloride dimer, 2 mg, 0.0055 mM) and cesium carbonate (269 mg, 0.825 mM) were suspended in toluene (0.8 ml) then degassed by bubbling nitrogen through for 5 minutes. The reaction was heated at 90° C. with stirring for 3 minutes then 2,2,2-trifluoroethanol (0.080 ml, 1.10 mM) and 3-chloro-2-hydroxy-4-methyl-1-[4-(trifluoromethyl)-2-pyridyl]-2H-pyrrol-5-one (161 mg, 0.550 mM) were added and the reaction was heated at 9000 with stirring in a sealed tube for 1 hour 50 minutes. The reaction was cooled to room temperature, diluted with ethyl acetate (20 ml), then filtered through celite and the filtrate was evaporated to give a glassy solid (202 mg) which was chromatographed to give a pale pink brown solid (12 mg, 6%)

$^1$H NMR ($CDCl_3$) 8.64 (d, 1H), 8.42 (d, 1H), 7.23 (dd, 1H), 6.25 (s, 1H), 4.76 (q, 2H), 1.86 (s, 3H)

Melting point 133-138° C.

Example 24: Preparation of 2-hydroxy-3-methoxy-4-methyl-1-[6-(1-piperidyl)pyrimidin-4-yl]-2H-pyrrol-5-one (CD1)

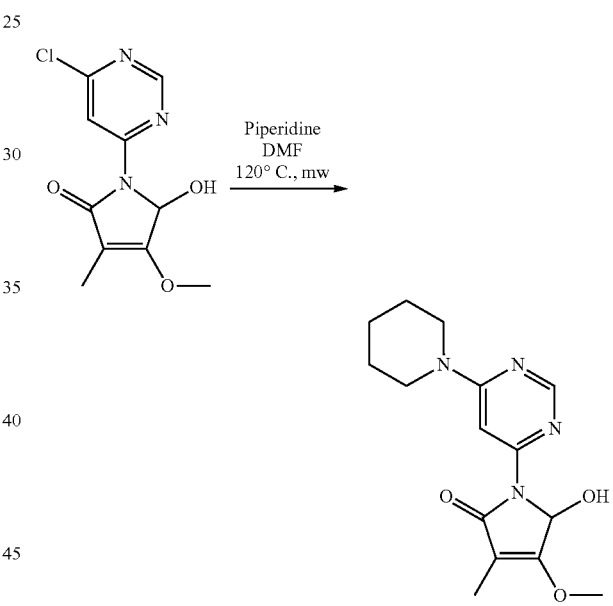

1-(6-chloropyrimidin-4-yl)-2-hydroxy-3-methoxy-4-methyl-2H-pyrrol-5-one (0.074 g, 0.29 mM) and piperidine (0.25 g, 2.9 mM, 0.29 mL) were dissolved in N,N-dimethylformamide (3 mL). The solution was heated with stirring in a microwave at 120° C. for 15 minutes. The mixture was diluted with water (10 mL) and extracted with diethyl ether (3×10 mL). The organic extracts were combined, washed with water (2×2 mL), dried over magnesium sulfate, filtered and the filtrate evaporated producing a yellow gum which was chromatographed to give a pale yellow gum. Diethyl ether (1 mL) was added, and the solution allowed to stand at ambient temperature. After 30 minutes the mixture was triturated with iso-hexane (1 mL) and the solid filtered off, washed with iso-hexane and dried under suction to give 2-hydroxy-3-methoxy-4-methyl-1-[6-(1-piperidyl)pyrimidin-4-yl]-2H-pyrrol-5-one as a white powder (40 mg, 44%)

$^1$H NMR ($CDCl_3$): δ8.28 (s, 1H); 7.51 (s, 1H); 6.08 (s, 1H); 5.75 (s, 1H); 4.13 (s, 3H); 3.63 (t, 4H); 1.85 (s, 3H); 1.68 (m, 2H); 1.61 (m, 4H)

Example 25: Preparation of 3-chloro-4-ethyl-1-[4-(trifluoromethyl)-2-pyridyl]pyrrole-2,5-dione

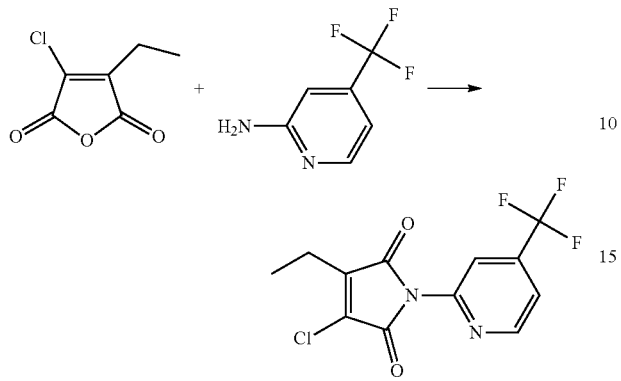

3-chloro-4-ethyl-furan-2,5-dione (assume 100% from previous reaction, 2.5 mM) and 4-Trifluoromethyl pyridine-2-ylamine (0.405 g, 2.5 mM) were stirred in toluene (10 ml) then p-Toluene sulphonic acid monohydrate (0.01 g, cat.) was added and the mixture heated to 95° C. After 1 hour analysis by UPLC indicated the presence of the desired product so the solvent was removed and the crude material purified by chromatography. The desired product was observed as a white solid (0.158 g, 21% over 3 steps).

$^1$H NMR (CDCl$_3$): δ 8.81 (1H, d); 7.63 (1H, s); 7.55 (1H, d); 2.64 (2H, q); 1.28 (3H, t).

Example 26: Preparation of 3-ethoxy-2-hydroxy-4-methyl-1-[4-(trifluoromethyl)-2-pyridyl]-2H-pyrrol-5-one (AD45)

AD45

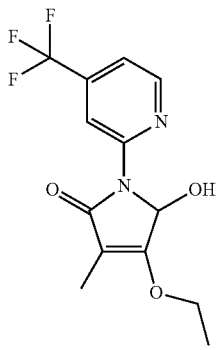

Step 1

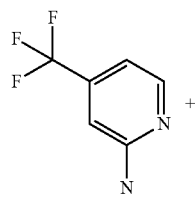

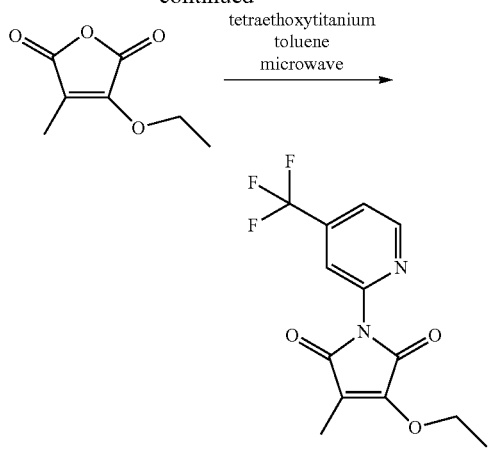

3-ethoxy-4-methyl-furan-2,5-dione (400 mg, 70% pure by mass so 1.792 mM, prepared as described in example 3) and 4-(trifluoromethyl)pyridin-2-amine (457 mg, 2.82 mM) were dissolved in toluene (3.5 ml) then tetraethoxytitanium (292 mg, 1.28 mM) was added and the reaction was heated with stirring in a microwave at 130° C. for 30 minutes. A further 3-ethoxy-4-methyl-furan-2,5-dione (160 mg, 70% pure by mass so 0.717 mM) was added and the reaction was heated with stirring in a microwave at 130° C. for 30 minutes. The reaction was filtered through celite and washed through with EtOAc, and the filtrate was evaporated to give a waxy solid (792 mg). This was chromatographed to give a white solid (503 mg, 65%)

$^1$H NMR (CDCl$_3$) 8.78 (d, 1H), 8.42 (d, 1H), 7.50 (dd, 1H), 4.53 (q, 1H), 2.05 (s, 3H), 1.46 (t, 3H)

Step 2

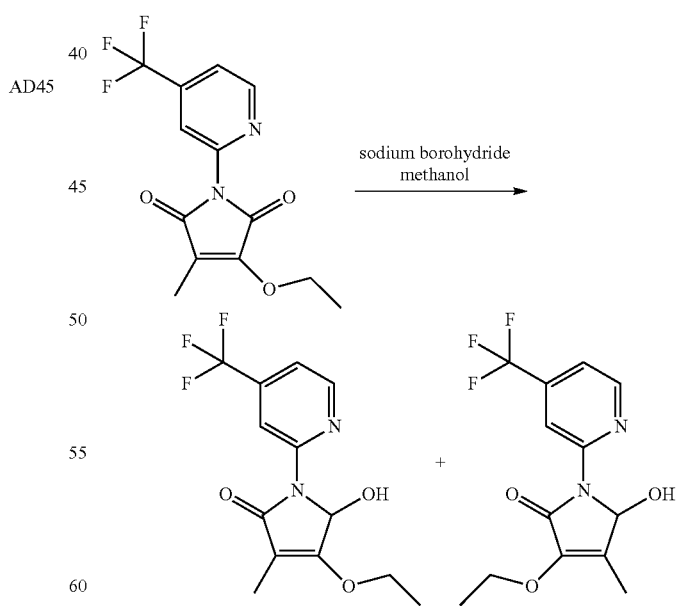

3-ethoxy-4-methyl-1-[4-(trifluoromethyl)-2-pyridyl]pyrrole-2,5-dione (363 mg, 1.209 mM) was dissolved in methanol (3 ml) then sodium borohydride (35 mg, 0.9069 mM) was added all at once, resulting in effervescence. The reaction was stirred at room temperature for 30 mins, then ethyl acetate (10 ml) and dilute brine (aq, 5 ml) were added and the reaction was shaken. The layers were separated, and the aqueous layer was extracted a further 2×5 ml ethyl acetate. The combined ethyl acetate extracts were dried with Na$_2$SO$_4$ and filtered. The filtrate was evaporated to give a white solid (360 mg) which was chromatographed to give 2 products:—

1$^{st}$ product:—4-ethoxy-2-hydroxy-3-methyl-1-[4-(trifluoromethyl)-2-pyridyl]-2H-pyrrol-5-one, white solid (7 mg, 1.9%)

$^1$H NMR (CDCl$_3$): 8.65 (d, 1H), 8.46 (d, 1H), 7.25 (dd, 1H), 6.01 (s, 1H), 4.36 (m, 2H), 2.05 (s, 3H), 1.37 (t, 3H)

2$^{nd}$ product:—white solid 3-ethoxy-2-hydroxy-4-methyl-1-[4-(trifluoromethyl)-2-pyridyl]-2H-pyrrol-5-one, white solid (140 mg, 38%)

$^1$H NMR (CDCl$_3$): 8.67 (d, 1H), 8.40 (d, 1H), 7.18 (dd, 1H), 6.14 (s, 1H), 5.27 (s, 1H), 4.57 (m, 1H), 4.38 (m, 1H), 1.89 (s, 3H), 1.45 (t, 3H)

Example 27: Preparation of 5-bromo-4-(trifluoromethyl)pyridin-2-amine

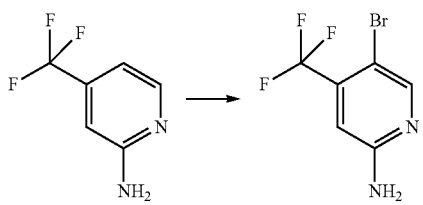 [SMILES: Nc1cc(C(F)(F)F)ccn1 ; Nc1cc(C(F)(F)F)c(Br)cn1]

To a stirred solution of 4-(trifluoromethyl)pyridin-2-amine (5.00 g, 30.8 mmol) in dichloromethane (80 mL) added N-bromosuccinimide (5.55 g, 30.8 mmol). The solution stirred at ambient temperature for 2 hours.

1M aqueous sodium hydroxide and dichloromethane were added and the layers separated. The aqueous layer was extracted three times with dichloromethane. The combined organics washed with water, dried over MgSO$_4$ and concentrated in vacuo to orange oil. Chromatography on silica gel gave an orange solid (5.682 g, 76%)

$^1$H NMR CDCl$_3$ δ 8.29 (s, 1H), 6.78 (s, 1H), 4.74 (br. s, 2H)

Example 28: Preparation of 1-[5-bromo-4-(trifluoromethyl)-2-pyridyl]-3-chloro-4-methyl-pyrrole-2,5-dione

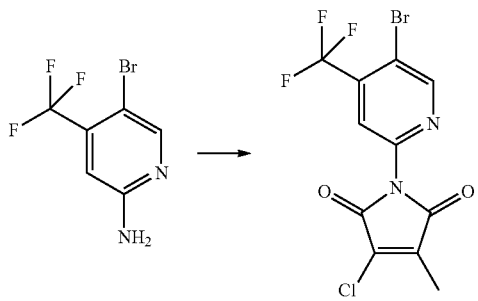 [SMILES: Nc1cc(C(F)(F)F)c(Br)cn1 ; CC1=C(Cl)C(=O)N(c2cc(C(F)(F)F)c(Br)cn2)C1=O]

3-chloro-4-methyl-furan-2,5-dione (1.00 g, 6.82 mmol) and 5-bromo-4-(trifluoromethyl)pyridin-2-amine (1.81 g, 7.51 mmol, prepared as described in example 1) combined in glacial acetic acid (15 mL). The solution was heated with stirring at 160 C for 30 minutes under microwave irradiation. The solution concentrated in vacuo. Saturated aqueous sodium bicarbonate and dichloromethane were added and the layers separated. The aqueous layer was extracted three times with dichloromethane. The combined organics washed with water, dried over MgSO$_4$ and concentrated in vacuo to brown oil. Chromatography on silica gel gave a white solid (1.409 g, 56%)

$^1$H NMR CDCl$_3$ δ 8.88 (s, 1H), 7.69 (s, 1H), 2.20 (s, 3H)

Example 29: Preparation of 1-[5-bromo-4-(trifluoromethyl)-2-pyridyl]-3-chloro-2-hydroxy-4-methyl-2H-pyrrol-5-one (AA25)

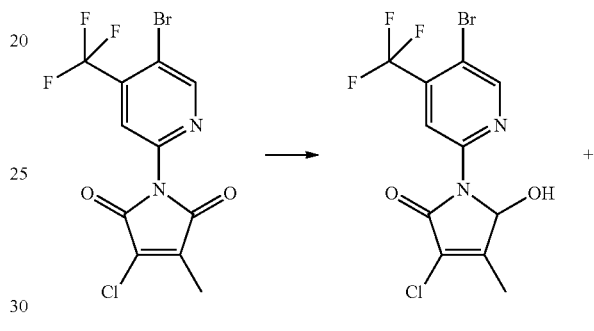

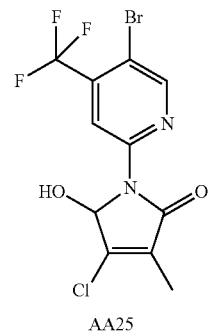

AA25

To 1-[5-bromo-4-(trifluoromethyl)-2-pyridyl]-3-chloro-4-methyl-pyrrole-2,5-dione (1.661 g, 4.49 mmol, prepared as described in example 2) in methanol (30 mL) and tetrahydrofuran (20 mL), at −10 C, added sodium borohydride (0.191 g, 4.95 mmol). The solution was stirred for one hour. Water and ethyl acetate were added and the layers separated. The aqueous layer was extracted three times with ethyl acetate. The combined organics washed with water, dried over MgSO$_4$ and concentrated in vacuo to a white solid. Chromatography on silica gel gave 1-[5-bromo-4-(trifluoromethyl)-2-pyridyl]-4-chloro-2-hydroxy-3-methyl-2H-pyrrol-5-one (0.366 g, 22%) and 1-[5-bromo-4-(trifluoromethyl)-2-pyridyl]-3-chloro-2-hydroxy-4-methyl-2H-pyrrol-5-one (1.053 g, 63%)

Example 30: Preparation of 2-chloro-4-[chloro(difluoro)methyl]pyridine

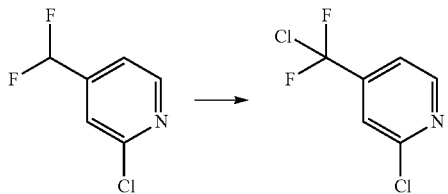 [SMILES: FC(F)c1ccnc(Cl)c1 ; FC(F)(Cl)c1ccnc(Cl)c1]

2-chloro-4-(difluoromethyl)pyridine (prepared as outlined in example 18) (0.95 g, 5.81 mM) was suspended in CCl4 (3.3 ml), then trichloro isocyanuric acid (TCICA, 675 mg, 2.9 mM) and bis benzoylperoxide (BBPO, 70 mg, 0.29 mM) were added and the mixture was heated to 160° C. in the microwave for 30 mins. More BBPO (70 mg, 0.29 mM) was added and the mixture was heated to 180° C. in the microwave for 20 mins. More BBPO (70 mg, 0.29 mM) was added and the mixture was heated to 180° C. in the microwave for 20 mins. The mixture was cooled, filtered through celite, the residue was washed with dichloromethane. 2.3 g celite were added to filtrate and it was concentrated to dryness, then purified by column chromatography on silica (eluent: 0-7% ethyl acetate in isohexane) to give 700 mg colourless oil (61% yield)

1H NMR (CDCl$_3$) 8.58 (1H, dd), 7.57 (d, 1H), 7.45 (dd, 1H)

Table 1 lists compounds of the general formula wherein $R^1$, $R^2$, $R^3$ and A are as defined in the table.

These compounds were made by the general methods of Examples 1 to 29.

TABLE 1

Compounds of the Invention

A = substituted pyrid-2-yl

| Compound Number | $R^1$ | $R^2$ | $R^3$ | A | LC-MS (MH+, RT in minutes)$^a$/ melting point$^c$ ° C. | 1H NMR (measured in CDCl$_3$ unless otherwise indicated) δ |
|---|---|---|---|---|---|---|
| AA1 | Me | Cl | OH | 5-(2-ethoxyvinyl)-4-(trifluoromethyl)pyridin-2-yl | | 9.16 (s, 1H), 8.57 (s 1H), 6.40 (d, 1H), 6.13 (d, 1H), 5.43-5.39 (m, 1H), 5.38 (d, 1H), 4.07 (q, 2H), 1.99 (s, 3H), 1.40 (t, 3H) |
| AA2 | Me | Cl | OH | 5-(2-methylprop-1-en-1-yl)-4-(trifluoromethyl)pyridin-2-yl | | 8.62 (s, 1H), 8.09 (s, 1H), 6.16-6.11 (m, 1H), 5.31 (d, 0.5H), 5.25 (d, 0.5H), 2.00 (s, 3H), 1.91 (s, 3H), 1.85 (s, 3H), 1.41 (app. d, 3H) |
| AA4 | Me | Cl | OH | 3-Fluoro-4-trifluoromethyl Pyridin-2-yl | /101 to 106 | 8.38 (d, 1H): 7.46 (t, 1H); 6.20 (d, 1H); 4.21 (d, 1H); 1.98 (d, 3H) |

TABLE 1-continued

Compounds of the Invention

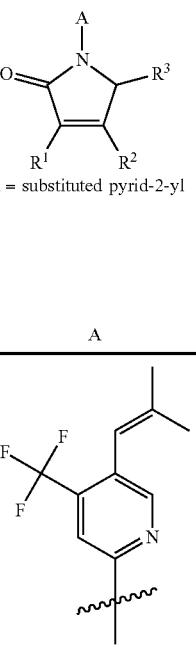

A = substituted pyrid-2-yl

| Compound Number | R¹ | R² | R³ | A | LC-MS (MH⁺, RT in minutes)[a]/ melting point[c] °C. | 1H NMR (measured in CDCl₃ unless otherwise indicated) δ |
|---|---|---|---|---|---|---|
| AA7 | Me | Cl | OH | 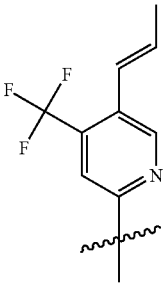 [SMILES: *c1cc(C(F)(F)F)c(/C=C/C)cn1] | /156 to 159 | 8.61 (s, 1H), 8.23 (s, 1H), 6.25 (m, 1H), 6.14 (m, 1H), 5.27 (d, 1H), 2.00 (s, 3H), 1.96 (s, 3H), 1.74 (s, 3H) |
| AA8 | Me | Cl | OH | | /180 to 182 | 8.58 (s, 1H), 8.52 (s, 1H), 6.66-6.58 (m, 1H), 6.30-6.19 (m, 1H), 6.13 (d, 1H), 5.23 (d, 1H), 1.99 (s, 3H), 1.96 (dd, 3H) |
| AA9 | Me | Cl | OH | 4-isopropyl-5-isopropoxycarbonyl Pyridin-2-yl | /92.5-96.7 | 8.72 (s, 1H); 8.40 (s, 1H); 6.12 (s, 1H); [OH not seen]; 5.26 (m, 1H); 3.89 (m, 1H); 1.98 (s, 3H); 1.38 (d, 6H); 1.29 (d, 3H); 1.28 (d, 3H) |
| AA10 | Me | Cl | OH | 4-methyl-5-bromo Pyridin-2-yl | /186.7-189.7 | 8.32 (s, 1H); 8.26 (s, 1H); 6.07 (q, 1H); 5.35 (d, 1H); 2.43 (s, 3H); 1.97 (d, 3H) |
| AA13 | Me | Cl | OH | 4-methyl Pyridin-2-yl | | 8.15 (d, 1H); 8.13 (d, 1H); 6.88 (dd, 1H); 6.08 (s, 1H); 5.81 (s, 1H); 2.38 (s, 3H); 1.97 (s, 3H) |
| AA14 | Me | Cl | OH | 4-Methoxy Pyridin-2-yl | | 8.08 (d, 1H); 7.91 (d, 1H); 6.61 (dd, 1H); 6.09 (s, 1H); 5.89 (s, 1H); 3.89 (s, 3H); 1.98 (s, 3H) |
| AA16 | Me | Cl | OH | 4,5-Dichloropyridin-2-yl | | 8.52 (s, 1H); 8.30 (s, 1H); 6.09 (d, 1H); 5.06 (d, 1H); 1.99 (s, 3H) |
| AA20 | Me | Cl | OH | 4-Cyanopyridin-2-yl | | 8.65 (d, 1H); 8.47 (d, 1H); 7.28 (dd, 1H); 6.12 (d, 1H); 5.05 (d, 1H); 2.00 (s, 3H) |

TABLE 1-continued

Compounds of the Invention

A = substituted pyrid-2-yl

| Compound Number | R¹ | R² | R³ | A | LC-MS (MH+, RT in minutes)$^a$/ melting point$^c$ ° C. | 1H NMR (measured in CDCl₃ unless otherwise indicated) δ |
|---|---|---|---|---|---|---|
| AA25 | Me | Cl | OH | 5-Bromo-4-Trifluoromethyl Pyridin-2-yl | LCMS 1.67 mins ES+ 371/373 MH+/ 206 to 207 | 8.74 (s, 1H), 8.57 (s, 1H), 6.13 (d, 1H), 4.90 (d, 1H), 2.00 (s, 3H) |
| AA26 | Me | Cl | OH | 5-Chloro-4-Trifluoromethyl Pyridin-2-yl | LCMS 1.63 mins ES+ 327/329 MH+/ 197.5 to 198 | 8.73 (s, 1H), 8.44 (s, 1H), 6.13 (d, 1H), 4.88 (d, 1H), 2.00 (s, 3H) |
| AA27 | Me | Cl | OH | 5-(4-Methoxyphenyl) Pyridin-2-yl | | 8.47 (m, 1H), 8.45 (d, 1H), 7.92 (m, 1H), 7.50 (d, 2H), 7.00 (d, 2H), 6.15 (m, 1H), 5.67 (m, 1H), 3.87 (s, 3H), 2.00 (s, 3H) |
| AA31 | Me | Cl | OH | 4-Bromo Pyridin-2-yl | | 8.58 (d, 1H); 8.11 (d, 1H); 7.22 (dd, 1H); 6.09 (d, 1H); 5.40 (d, 1H); 1.98 (s, 3H) |
| AA32 | Me | Cl | OH | 5-Chloro Pyridin-2-yl | | 8.30 (d, 1H); 8.26 (d, 1H); 7.72 (dd, 1H); 6.10 (d, 1H); 5.23 (d, 1H); 1.98 (s, 3H) |
| AA33 | Me | Cl | OH | 4-Chloro Pyridin-2-yl | | 8.40 (d, 1H); 8.19 (d, 1H); 7.08 (dd, 1H); 6.09 (d, 1H); 5.40 (d, 1H); 1.99 (s, 3H) |
| AA35 | Me | Cl | OH | 4-Trifluoromethyl Pyridin-2-yl | /176.3 to 177.5 | 8.63 (s, 1H); 8.47 (d, 1H); 7.29 (d, 1H); 6.14 (d, 1H); 5.22 (d, 1H); 2.00 (s, 3H) |
| AA36 | Me | Cl | OH | 5-Methyl Pyridin-2-yl | | 8.20 (dd, 1H); 8.10 (d, 1H); 7.55 (dd, 1H); 6.10 (s, 1H); 5.75 (br s, 1H); 2.30 (s, 3H); 1.98 (s, 3H) |
| AA38 | Me | Cl | OH | 5-Trifluoromethoxy Pyridin-2-yl | /123.5 to 128 | 8.30 (d, 1 H) 8.25 (d, 1 H) 6.83-6.97 (m, 1 H) 6.11 (d, 1 H) 5.38 (d, 1 H) 1.98 (s, 3 H) |

TABLE 1-continued

Compounds of the Invention

A = substituted pyrid-2-yl

| Compound Number | R¹ | R² | R³ | A | LC-MS (MH⁺, RT in minutes)$^a$/ melting point$^c$ °C. | 1H NMR (measured in CDCl₃ unless otherwise indicated) δ |
|---|---|---|---|---|---|---|
| AA39 | Me | Cl | OH | (structure: 4-trifluoromethyl-5-(3,3-dimethylbut-1-enyl)pyridin-2-yl) | /154 to 157 | 8.58 (s, 1H), 8.52 (s, 1H), 6.56-6.48 (m, 1H), 6.22 (d, 1H), 6.14 (m, 1H), 5.28 (m, 1H), 1.99 (s, 3H), 1.15 (s, 9H) |
| AA40 | nPr | Cl | OH | 4-Trifluoromethyl Pyridin-2-yl | | 8.64 (1H, s); 8.46 (1H, m); 7.29 (1H, m); 6.15 (1H, d); 5.27 (1H, d); 2.42 (2H, m); 1.65 (2H, m); 1.0 (3H, m). |
| AA41 | tBu | Cl | OH | 4-Trifluoromethyl Pyridin-2-yl | | 8.65 (1H, m); 8.46 (1H, m); 7.3 (1H, m); 6.0 (1H, m); 5.26 (1H, m); 1.47 (9H, s); 1.46 (9H, s). |
| AA42 | iPr | Cl | OH | 4-Trifluoromethyl Pyridin-2-yl | | 8.62 (1H, s); 8.45 (1H, d); 7.28 (1H, m); 6.1 (1H, m); 5.25 (1H, m); 3.02 (1H, m); 1.33 (6H, m); |
| AA43 | Et | Cl | OH | 4-Trifluoromethyl Pyridin-2-yl | | 8.63 (1H, s); 8.45 (1H, d); 7.28 (1H, d); 6.13 (1H, d); 5.25 (1H, d); 2.46 (2H, m); 1.2 (3H, m). |
| AA44 | Me | Cl | OH | 4-tert-butyl Pyridin-2-yl | | 8.37 (d, 1 H) 8.18 (d, 1 H) 7.07 (dd, 1 H) 6.09 (d, 1 H) 5.83 (br. s., 1 H) 1.97 (s, 3 H) 1.33 (s, 9 H) |
| AA45 | Me | Cl | OH | 4-trifluoromethyl-5-tert-butyloxy carbonyl Pyridin-2-yl | /182-186 | 8.80 (s, 1 H) 8.72 (s, 1 H) 6.17 (d, 1 H) 5.06 (s, 1 H) 2.00 (d, 3 H) 1.60 (s, 9 H) |
| AA46 | Me | Cl | OH | 4-trifluoromethyl-5-tert-butylamino carbonyl Pyridin-2-yl | | 8.61 (s, 1 H) 8.48 (s, 1 H) 6.10-6.18 (m, 1 H) 5.68-5.84 (m, 1 H) 5.10 (d, 1 H) 1.99 (d, 3H) 1.46 (s, 9 H) |

TABLE 1-continued

Compounds of the Invention

A = substituted pyrid-2-yl

| Compound Number | R¹ | R² | R³ | A | LC-MS (MH+, RT in minutes)$^a$/ melting point$^c$ ° C. | 1H NMR (measured in CDCl$_3$ unless otherwise indicated) δ |
|---|---|---|---|---|---|---|
| AA47 | Me | Cl | OH | 4-chloro-5-ethoxycarbonyl Pyridin-2-yl | | 8.82 (s, 1 H) 8.49 (s, 1 H) 6.13 (dd, 1 H) 5.21 (d, 1 H) 4.42 (q, 2 H) 1.98 (d, 3 H) 1.42 (t, 3 H) |
| AA48 | Me | Cl | OH | (4-methyl-5-(thiophen-3-yl)pyridin-2-yl) | | 8.22 (s, 1H); 8.18 (s, 1H); 7.43 (m, 1H); 7.26 (m, 1H); 7.14 (d, 1H); 6.11 (s, 1H); 5.72 (bs 1H); 2.39 (s, 3H); 1.99 (s, 3H) |
| AA49 | Me | Cl | OH | (4-isopropyl-5-(N-tert-butylcarbamoyl)pyridin-2-yl) | | 8.22 (s, 1 H) 8.08 (s, 1 H) 6.02 (s, 1 H) 5.72 (br. s, 1 H) 5.54 (s, 1 H) 3.34 (spt, 1 H) 1.89 (d, 3 H) 1.39 (s, 9 H) 1.19 (dd, 6 H) |
| AA50 | Me | Cl | OH | 4-ethyl-5-bromo-Pyridin-2-yl | | 8.32 (s, 1 H) 8.27 (s, 1 H) 6.04-6.10 (m, 1 H) 5.35 (d, 1 H) 2.77 (q, 2 H) 1.97 (d, 3 H) 1.27 (t, 3 H) |
| AB1 | Me | Br | OH | 4-Trifluoromethyl Pyridin-2-yl | | 8.62 (s, 1H), 8.47 (d, 1H), 7.29 (dd, 1H), 6.17-6.19 (m, 1H), 5.26 (d, 1H), 1.99 (s, 3H) |
| AD2 | Me | OMe | OH | 4-Trifluoromethyl-5-methylcarbonyl Pyridin-2-yl | /172 to 175 | 8.78 (s, 1H); 8.57 (s, 1H); 6.18-6.19 (d, 1H); 5.04-5.05 (d, 1h); 4.18 (s, 3H); 2.61 (s, 3H); 1.91 (s, 3H). |

TABLE 1-continued

Compounds of the Invention

A = substituted pyrid-2-yl

| Compound Number | R¹ | R² | R³ | A | LC-MS (MH⁺, RT in minutes)[a]/ melting point[c] °C. | 1H NMR (measured in CDCl₃ unless otherwise indicated) δ |
|---|---|---|---|---|---|---|
| AD3 | Me | OMe | OH | 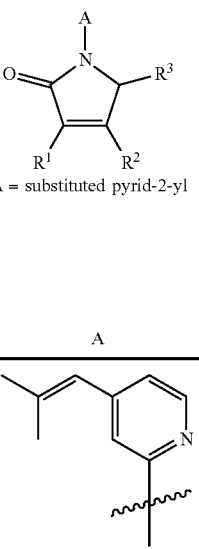 | /104.4-119.1 | 8.24 (s, 1H); 8.13 (d, 1H); 6.81 (dd, 1H); 6.19 (s, 1H); 6.13 (d, 1H); 5.87 (s, 1H); 4.14 (s, 3H); 1.96 (d, 3H); 1.94 (d, 3H); 1.88 (d, 3H) |
| AD4 | Me | OMe | OH | 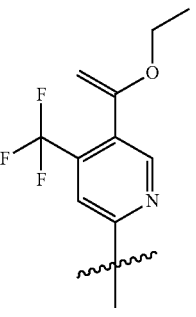 [SMILES: *c1cc(C(F)(F)F)c(C(=C)OCC)cn1] | /97-102 | 8.68 (s, 1H); 8.37 (s, 1H); 6.16 (d, 1H); 5.23 (d, 1H); 4.37 (d, 1H); 4.28 (d, 1H); 4.16 (s, 3H); 3.90 (q, 2H); 1.90 (s, 3H); 1.36 (t, 3H). |
| AD5 | Me | OMe | OH | 3-Cyano-4-trifluoromethyl Pyridin-2-yl | /145-153 | 8.76 (d, 1H): 7.52 (d, 1H); 6.41 (d, 1H); 4.18 (s, 3H); 3.89 (d, 1H); 1.95 (s, 3H). |
| AD7 | Me | OMe | OH | 3-Fluoro-4-trifluoromethyl Pyridin-2-yl | /137-142 | 8.26 (d, 1H), 7.31 (t, 1H), 6.13 (s, 1H), 4.15 (bs, 1H), 4.07 (s, 3H), 1.84 (s, 3H) |
| AD9 | Me | OMe | OH | 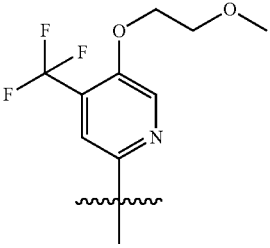 [SMILES: *c1cc(C(F)(F)F)c(OCCOC)cn1] | /103-113 | 8.61 (s, 1H), 8.11 (s, 1H), 6.10 (s, 1H), 5.17 (br s, 1H), 4.26 (dd, 2H), 3.79 (dd, 2H), 3.46 (s, 3H), 1.90 (s, 3H) |
| AD10 | Me | OMe | OH | 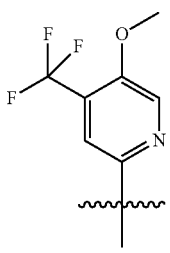 [SMILES: *c1cc(C(F)(F)F)c(OC)cn1] | /136-140 | 8.62 (s, 1H), 8.06 (s, 1H), 6.10 (s, 1H), 4.15 (s, 3H), 3.97 (s, 1H), 1.90 (s, 3H) |

TABLE 1-continued

Compounds of the Invention

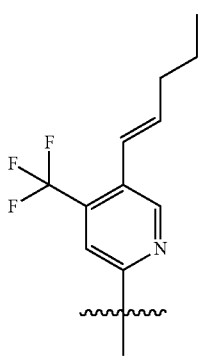 [SMILES: *c1cc(C(F)(F)F)c(/C=C/CCC)cn1]

A = substituted pyrid-2-yl

| Compound Number | R¹ | R² | R³ | A | LC-MS (MH⁺, RT in minutes)$^a$/ melting point$^c$ ° C. | 1H NMR (measured in CDCl₃ unless otherwise indicated) δ |
|---|---|---|---|---|---|---|
| AD11 | Me | OMe | OH | 4-difluoromethyl Pyridin-2-yl | /141.3-145.6 | d8.46 (d, 1H); 8.39 (d, 1H); 7.84 (dd, 1H); 6.66 (t, 1H); 6.16 (d, 1H); 5.40 (d, 1H); 4.16 (s, 3H); 1.89 (s, 3H) |
| AD12 | Me | OMe | OH | 4-Fluoro Pyridin-2-yl | /126.1-142.3 | d8.19 (dd, 1H); 8.12 (dd, 1H); 6.74 (ddd, 1H); 6.13 (s, 1H); 5.53 (s, 1H); 4.15 (s, 3H); 1.88 (s, 3H) |
| AD13 | Me | OMe | OH | 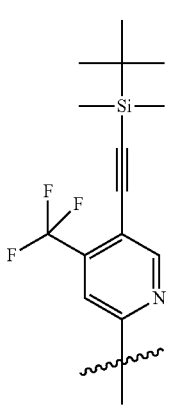 [SMILES: *c1cc(C(F)(F)F)c(C#C[Si](C)(C)C(C)(C)C)cn1] | | 8.53 (s, 1H), 8.39 (s 1H), 6.55-6.47 (m 2H), 5.23 (bs, 1H) 4.09 (s, 3H), 2.17 (m, 2H), 1.45 (h, 2H), 0.89 (t, 3H) |
| AD14 | Me | OMe | OH | 5-Methylsulfanyl-4-trifluoromethyl Pyridin-2-yl | | 8.62 (s, 1 H) 8.31 (s, 1 H) 6.07 (br. s., 1 H) 5.05 (d, 1 H) 4.09 (s, 3 H) 2.44 (s, 3 H) 1.83 (s, 3 H) |
| AD15 | Me | OMe | OH | | /138 to 145 | 8.6 (s, 1H); 8.38 (s, 1H); 6.1 (m, 1H); 5.01 (d, 1H); 4.09 (s, 3H); 1.81 (s, 3H); 0.19 (s, 9H) |

TABLE 1-continued

Compounds of the Invention

A = substituted pyrid-2-yl

| Compound Number | R¹ | R² | R³ | A | LC-MS (MH⁺, RT in minutes)$^a$/ melting point$^c$ °C. | 1H NMR (measured in CDCl₃ unless otherwise indicated) δ |
|---|---|---|---|---|---|---|
| AD16 | Me | OMe | OH | [structure: 4-trifluoromethyl-5-(1-methylethenyl) pyridin-2-yl] | /143 to 149 | 8.64 (s, 1H); 8.18 (s, 1H); 6.16 (m, 1H); 5.32 (m, 1H); 5.28 (d, 1H); 4.96 (s, 1H); 4.16 (s, 3H); 2.07 (s, 3H) |
| AD18 | Me | OMe | OH | [structure: 4-(1-fluoroethyl) pyridin-2-yl] | | 8.28 (s, 1H); 8.24 (d, 1H); 7.03 (m, 1H); 6.14 (s, 1H); 5.65 (s, 1H); 5.61 (m, 1H); 4.15 (s, 3H); 1.89 (d, 3H); 1.64 (ddd, 3H) |
| AD19 | Me | OMe | OH | [structure: 4-(1-fluoro-1-methylethyl) pyridin-2-yl] | /106.0-111.2 | 8.50 (d, 1H); 8.31 (d, 1H); 7.11 (dd, 1H); 6.15 (s, 1H); 5.48 (s, 1H); 4.15 (s, 3H); 1.92 (t, 3H) 1.89 (d, 3H) |
| AD20 | Me | OMe | OH | 4-Trifluoromethyl-5-ethynyl Pyridin-2-yl | | 8.71 (s, 1 H) 8.51 (s, 1 H) 6.16 (s, 1 H) 4.97-5.12 (m, 1 H) 4.17 (s, 3 H) 3.41 (s, 1 H) 1.89 (s, 3 H) |
| AD21 | Me | OMe | OH | [structure: 4-trifluoromethyl-5-(2-methylprop-1-enyl) pyridin-2-yl] | | 8.63 (s, 1 H) 8.16 (s, 1 H) 6.23 (br. s., 1 H) 6.15 (d, 1 H) 5.33 (d, 1 H) 4.13-4.19 (m, 3 H) 4.16 (s, 3 H) 1.94 (s, 3H) 1.90 (s, 3H) 1.72 (s, 3 H) |

TABLE 1-continued

Compounds of the Invention

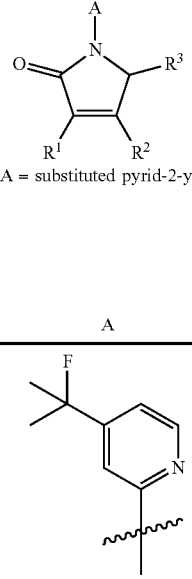

A = substituted pyrid-2-yl

| Compound Number | R¹ | R² | R³ | A | LC-MS (MH⁺, RT in minutes)$^a$/ melting point$^c$ °C. | 1H NMR (measured in CDCl₃ unless otherwise indicated) δ |
|---|---|---|---|---|---|---|
| AD23 | Me | OMe | OH |  | /103.4-136.5 | 8.31 (d, 1H); 8.22 (d, 1H); 7.07 (dd, 1H); 6.14 (s, 1H); 5.67 (s, 1H); 4.15 (s, 3H); 1.89 (s, 3H); 1.71 (s, 3H); 1.65 (s, 3H) |
| AD24 | Me | OMe | OH | 4-Bromo Pyridin-2-yl | /134.2-139.0 | 8.60 (d, 1H); 8.05 (d, 1H); 7.14 (dd, 1H); 6.10 (d, 1H); 5.43 (d, 1H); 4.15 (s, 3H); 1.88 (s, 3H) |
| AD25 | Me | OMe | OH | 3-Bromo-4-trifluoromethyl Pyridin-2-yl |  | 8.54 (d, 1 H) 7.52 (d, 1 H) 6.15 (d, 1 H) 4.13 (s, 3 H) 3.64 (br. s., 1 H) 1.91 (s, 3 H) |
| AD26 | Me | OMe | OH | 4-Trifluoromethyl-5-cyano Pyridin-2-yl |  | 8.86 (s, 8 H) 8.70 (s, 1 H) 6.20 (dd, 1 H) 4.79 (d, 1 H) 4.19 (s, 3 H) 1.91 (s, 3 H) |
| AD27 | Me | OMe | OH | 4-Trifluoromethyl-5-vinyl Pyridin-2-yl |  | 8.64 (s, 1 H) 8.53 (s, 1 H) 6.85-7.00 (m, 1 H) 6.16 (s, 1 H) 5.73 (d, 1 H) 5.44 (d, 1 H) 5.26 (br. s., 1 H) 4.16 (s, 3 H) 1.89 (s, 3 H) |
| AD28 | Me | OMe | OH | 4-Trifluoromethyl-5-methyl Pyridin-2-yl |  | 8.55 (s, 1 H) 8.12 (s, 1 H) 6.04-6.07 (m, 1 H) 5.23 (d, 1 H) 4.08 (s, 3 H) 2.33 (d, 3 H) 1.82 (s, 3 H) |
| AD29 | Me | OMe | OH | 4-Trifluoromethyl-3,5-dibromo Pyridin-2-yl |  | 8.59 (s, 1 H) 6.05 (d, 1 H) 4.07 (s, 3 H) 2.87-3.28 (m, 1 H) 1.84 (s, 3 H) |
| AD30 | Me | OMe | OH | 4-Trifluoromethyl-5-chloro Pyridin-2-yl |  | 8.76 (s, 1 H) 8.37 (s, 1 H) 6.14 (dd, 1 H) 4.93 (d, 1 H) 4.16 (s, 3 H) 1.90 (s, 3 H) |
| AD31 | Me | OMe | OH | 4-Trifluoromethyl-5-bromo Pyridin-2-yl |  | 8.77, (s, 1H) 8.50, (s, 1H) 6.13, (d, 1H) 4.95, (d, 1H) 4.18, (s, 3H) 1.91, (s, 3H) |
| AD33 | Me | OMe | OH | 5-Vinyl Pyridin-2-yl |  | 8.24 (d, 1H); 8.15 (d, 1H); 7.73 (dd, 1H); 6.58 (dd, 1H); 6.07 (s, 1H); 5.66 (d, 1H); 5.60 (s, |

TABLE 1-continued

Compounds of the Invention

A = substituted pyrid-2-yl

| Compound Number | R¹ | R² | R³ | A | LC-MS (MH⁺, RT in minutes)ᵃ/ melting pointᶜ °C. | 1H NMR (measured in CDCl₃ unless otherwise indicated) δ |
|---|---|---|---|---|---|---|
| | | | | | | 1H); 5.22 (d, 1H); 4.08 (s, 3H); 1.82 (s, 3H) |
| AD34 | Me | OMe | OH | 4-Trifluoromethyl Pyridin-2-yl | | 8.66 (s, 1H), 8.41 (d, 1H), 7.19 (d, 1H), 6.16 (s, 1H), 5.28 (s, 1H), 4.17 (s, 3H), 1.90 (s, 3H) |
| AD35 | Me | OMe | OH | 5-Trifluoromethyl Pyridin-2-yl | | 8.52 (bs, 1H), 8.49 (d, 1H), 7.92 (dd, 1H), 6.17 (bs, 1H), 5.29 (fine d, 1H), 4.18 (s, 3H), 1.89 (s, 3H) |
| AD37 | Me | OMe | OH | 4-Trifluoromethyl-5-methoxycarbonyl Pyridin-2-yl | | 8.83 (s, 1H); 8.80 (s, 1H); 6.21 (d, 1H); 5.10 (d 1H); 4.18 (s, 3H), 3.95 (s, 3H); 1.90 (s, 3H) |
| AD38 | Me | OMe | OH | (structure shown) | | 8.74 (s, 1H); 8.16 (s, 1H); 6.16 (bs, 1H); 5.35 (d, 1H); 5.02 (bs, 1H); 4.17 (s, 3H);, 2.40 (s, 3H); 1.90 (s, 3H). |
| AD39 | Me | OMe | OH | 4-Trifluoromethoxy Pyridin-2-yl | | 1.89 (s, 3 H) 4.15 (s, 3 H) 5.42 (s, 1 H) 6.13 (d, 1 H) 6.84 (d, 1 H) 8.12-8.35 (m, 2H) |
| AD40 | Me | OMe | OH | 4-Tert-butyl Pyridin-2-yl | | 8.39 (d, 1 H) 8.12 (s, 1 H) 6.91-7.10 (m, 1 H) 6.11 (s, 1 H) 4.12 (s, 3 H) 1.87 (d, 3 H) 1.31 (s, 9 H) |
| AD41 | Me | OMe | OH | 4-(2-methyl-prop-1-yl) Pyridin-2-yl | | 11.60 (s, 1H); 8.26 (s, 1H); 8.12 (d, 1H); 7.14 (dd, 1H); 6.46 (s, 1H); 4.16 (s, 3H); 2.67 (d, 2H); 2.01 (m, 1H); 1.83 (s, 3H); 0.96 (dd, 6H) |
| AD42 | Me | Oallyl | OH | 4-Trifluoromethyl Pyridin-2-yl | /97-102 | 8.66 (d, 1H), 8.40 (d, 1H), 7.20 (dd, 1H), 6.18 (m, 1H), 6.04 (m, 1H), 5.38 (m, 2H), 5.32 m (m |

TABLE 1-continued

Compounds of the Invention

A = substituted pyrid-2-yl

| Compound Number | R¹ | R² | R³ | A | LC-MS (MH⁺, RT in minutes)$^a$/ melting point$^c$ °C. | 1H NMR (measured in CDCl₃ unless otherwise indicated) δ |
|---|---|---|---|---|---|---|
| AD44 | Me | OCH2CF3 | OH | 4-Trifluoromethyl Pyridin-2-yl | /133-138 | 1H), 4.93 (m, 2H), 1.88 (s, 3H) 8.64 (d, 1H), 8.42 (d, 1H), 7.23 (dd, 1H), 6.25 (s, 1H), 4.76 (q, 2H), 1.86 (s, 3H) |
| AD45 | Me | OEt | OH | 4-Trifluoromethyl Pyridin-2-yl | /131-135 | 8.67 (d, 1H), 8.40 (d, 1H), 7.18 (dd, 1H), 6.14 (s, 1H), 5.27 (s, 1H), 4.57 (m, 1H), 4.38 (m, 1H), 1.89 (s, 3H), 1.45 (t, 3H) |
| AD47 | Me | OMe | OH | 5-trifluoromethoxy Pyridin-2-yl | /103-107 | 8.41 (s, 1 H) 8.19 (s, 1 H) 7.57-7.68 (m, 1 H) 6.08-6.21 (m, 1 H) 5.27 (s, 1 H) 4.15 (s, 3H) 1.89 (s, 3 H) |
| AD48 | Me | OMe | OH | (tert-butyl 4-(trifluoromethyl)pyridine-3-carboxylate, 6-yl attachment) | /132-136 | 8.80 (s, 2 H) 6.16-6.31 (m, 1 H) 5.17 (s, 1 H) 4.21 (s, 3 H) 1.94 (s, 3 H) 1.63 (s, 9 H) |
| AD49 | Me | OMe | OH | (5-(thiophen-3-yl)-4-(trifluoromethyl)pyridin-2-yl) | /135-139 | 8.76 (s, 1H), 8.32 (s, 1H), 7.41 (m, 1H), 7.33 (m, 1H), 7.15 (m, 1H), 6.20 (d, 1H), 5.25 (d, 1H), 4.17 (s, 3H), 1.91 (s, 3H) |

TABLE 1-continued

Compounds of the Invention

A = substituted pyrid-2-yl

| Compound Number | R¹ | R² | R³ | A | LC-MS (MH⁺, RT in minutes)ᵃ/ melting pointᶜ °C. | 1H NMR (measured in CDCl₃ unless otherwise indicated) δ |
|---|---|---|---|---|---|---|
| AD50 | Me | OMe | OH | 5-(4-fluorophenyl)-4-trifluoromethyl pyridin-2-yl (structure shown) | /121-127 | 8.77 (s, 1H), 8.24 (s, 1H), 7.29 (m, 2H), 7.14 (m, 2H), 6.20 (d, 1H), 5.23 (d, 1H), 4.18 (s, 3H), 1.93 (s, 3H) |
| AD51 | Me | OMe | OH | 5-iodo-4-trifluoromethyl pyridin-2-yl (structure shown) | | 8.76 (s, 1H), 8.72 (s, 1H), 6.03, (m, 1H), 4.96 (d, 1H), 4.16 (s, 3H), 1.90 (s, 3H) |
| AD52 | Me | OMe | OH | 4-(2-chloro-1,1-dimethylethyl) pyridin-2-yl (structure shown) | | 8.65 (d, 1H), 8.16 (d, 1H), 7.31 (dd, 1H), 6.52, (s, 1H), 4.18 (s, 3H), 3.72 (s, 2H), 1.86 (s, 3H), 1.51 (s, 6H) |
| AD53 | Me | OMe | OH | 4-trifluoromethyl-5-isopropylamino carbonyl Pyridin-2-yl | /181-186 | 8.67 (s, 1 H) 8.46 (s, 1 H) 6.12-6.20 (m, 1 H) 5.66-5.82 (m, 1 H) 5.08 (d, J = 3.36 Hz, 1 H) 4.21-4.33 (m, 1 H) 4.16 (s, 3 H) 1.89 (s, 3 H) 1.26 (d, J=6.58 Hz, 6 H) |
| AD54 | Me | OMe | OH | 4-trifluoromethyl-5-tertbutylamino carbonyl Pyridin-2-yl | /173-177 | 8.62 (s, 1 H) 8.41 (s, 1 H) 6.04-6.24 (m, 1 H) 5.66-5.92 (m, 1 H) 5.13 (d, J = 3.49 Hz, 1 H) 4.16 (s, 3 H) 1.88 (s, 3 H) 1.46 (s, 9 H) |
| AD55 | Me | OMe | OH | 4-trifluoromethyl-5-ethoxy Pyridin-2-yl | | 8.59 (s, 1H), 8.04 (s, 1H), 6.10 (s, 1H), |

TABLE 1-continued

Compounds of the Invention

A = substituted pyrid-2-yl

| Compound Number | R¹ | R² | R³ | A | LC-MS (MH$^+$, RT in minutes)$^a$/ melting point$^c$ °C. | 1H NMR (measured in CDCl$_3$ unless otherwise indicated) δ |
|---|---|---|---|---|---|---|
| AD56 | Me | OMe | OH | 4-trifluoromethyl-5-(1-methyl-prop-1-yloxy) Pyridin-2-yl | | 4.44 (br s, 1H), 4.18 (q, 2H), 4.14 (s, 3H), 1.88 (s, 3H), 1.47 (t, 3H) 8.62 (s, 1H), 8.01 (s, 1H), 6.12 (s, 1H, 4.87 (br s, 1H), 4.15 (s, 3H), 3.87 (d, 2H), 2.16 (septet, 1H), 1.89 (s, 3H), 1.06 (d, 6H) |
| AD57 | Me | OMe | OH | (structure shown) | | 8.60 (s, 1H), 8.09 (s, 1H), 6.11 (s, 1H), 5.19 (br s, 1H), 4.31 (m, 1H), 4.15 (s, 3H), 4.13 (m, 2H), 3.93 (m, 1H), 3.84 (m, 1H), 2.15 to 1.90 (m, 4H), 1.90 (s, 3H) |
| AD58 | Me | OMe | OH | (structure shown) | | 8.78 (s, 1 H) 8.19 (s, 1 H) 6.17 (s, 1 H) 5.64 (d, 1 H) 5.08 (br. s., 1 H) 4.16 (s, 3 H) 2.24 (s, 3 H) 1.90 (s, 3 H) |
| AD59 | Me | OMe | OH | (structure shown) | 0.69 Min 383 MH$^+$ | |

TABLE 1-continued
Compounds of the Invention
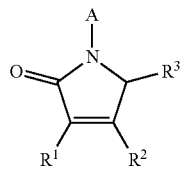
A = substituted pyrid-2-yl
| Compound Number | R¹ | R² | R³ | A | LC-MS (MH+, RT in minutes)ᵃ/ melting pointᶜ °C. | 1H NMR (measured in CDCl₃ unless otherwise indicated) δ |
|---|---|---|---|---|---|---|
| AD60 | Me | OMe | OH | 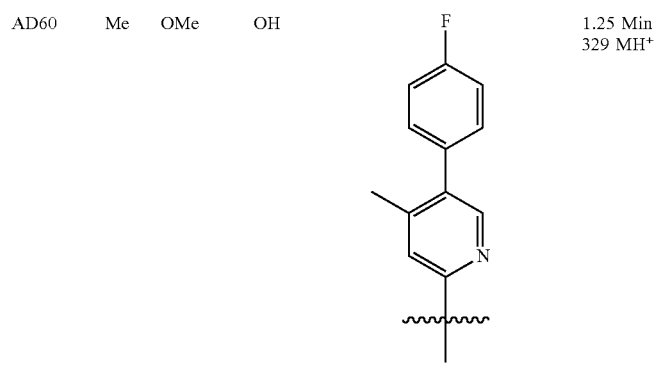 | 1.25 Min 329 MH+ | |
| AD61 | Me | OMe | OH | 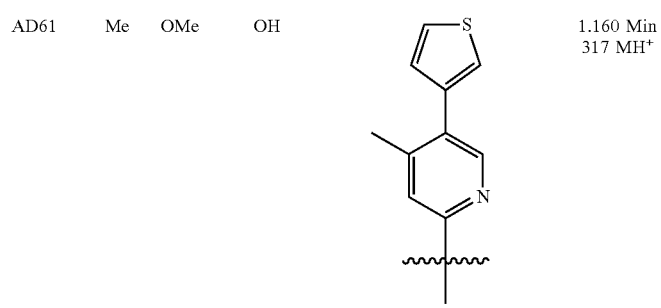 | 1.160 Min 317 MH+ | |
| AD62 | Me | OMe | OH | 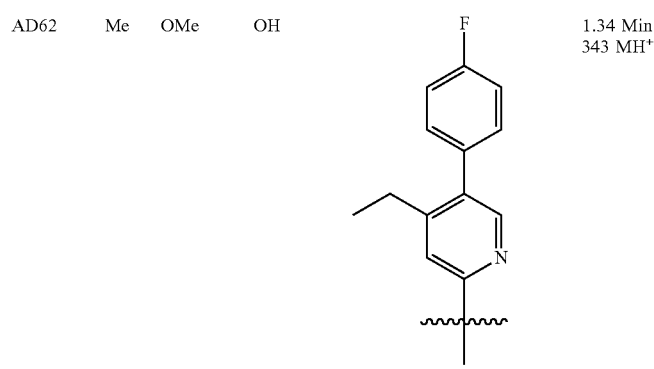 | 1.34 Min 343 MH+ | |

TABLE 1-continued

Compounds of the Invention

A = substituted pyrid-2-yl

| Compound Number | R¹ | R² | R³ | A | LC-MS (MH⁺, RT in minutes)$^a$/ melting point$^c$ °C. | 1H NMR (measured in CDCl₃ unless otherwise indicated) δ |
|---|---|---|---|---|---|---|
| AD63 | Me | OMe | OH | 4-methyl-5-phenyl-pyrid-2-yl | | 7.83-8.28 (m, 2H) 7.01-7.48 (m, 5H) 6.09 (d, 1 H) 5.74 (br. s., 1 H) 4.07 (s, 3 H) 2.23 (s, 3H) 1.82 (s, 3H) |
| AD64 | Me | OMe | OH | 5,6,7,8-tetrahydroisoquinolin-3-yl | | 8.02 (s, 1H), 7.93 (s, 1H), 6.08 (s, 1H), 5.90 (s, 1H), 4.13 (s, 3H), 2.77 (m, 2H), 2.70 (m, 2H), 1.87 (s, 3H), 1.79 (m, 4H) |
| AD65 | Me | OMe | OH | 5-(4-fluoro-2-methylphenyl)-4-methyl-pyrid-2-yl | | 8.26 (d, 1 H) 7.91 (s, 1 H) 6.86-7.11 (m, 4 H) 6.16 (d, 1 H) 5.64-5.92 (m, 1 H) 4.14 |
| AD66 | Me | OMe | OH | 5-(2-methylphenyl)-4-methyl-pyrid-2-yl | | 8.31 (d, 1 H) 8.00 (d, 1 H) 7.24-7.40 (m, 4 H) 7.07-7.17 (m, 1 H) 6.18-6.26 (m, 1 H) 5.92 (br. s 1 H) 4.20 (s, 3H) 2.14 (s, 3 H) 2.12 (d, 3H) 1.95 (s, 3 H) |

TABLE 1-continued

Compounds of the Invention

A = substituted pyrid-2-yl

| Compound Number | R¹ | R² | R³ | A | LC-MS (MH⁺, RT in minutes)$^a$/ melting point$^c$ ° C. | 1H NMR (measured in CDCl₃ unless otherwise indicated) δ |
|---|---|---|---|---|---|---|
| AD67 | Me | OMe | OH | 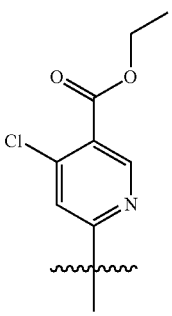 [SMILES: *c1cc(Cl)c(C(=O)OCC)cn1] | | 8.66 (d, 1H), 8.38 (d, 1H), 7.20 (dd, 1H), 6.16 (m, 1H), 5.31 (d, 1H), 4.16 (s, 3H), 1.91 (s, 3H) |
| AD68 | Me | OMe | OH | 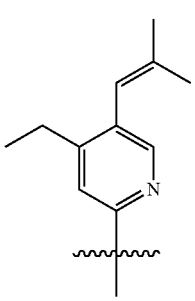 [SMILES: *c1cc(CC)c(C=C(C)C)cn1] | | 8.70 (s, 1 H) 8.42 (s, 1 H) 6.08 (d, 1 H) 5.17 (d, 1 H) 4.33 (q, 2 H) 4.09 (s, 3 H) 1.80 (d, 3 H) 1.33 (t, 3 H) |
| AD69 | Me | OMe | OH | 4-chloro-5-bromo Pyridin-2-yl | | 8.57 (s, 1 H) 8.37 (s, 1 H) 6.10 (s, 1 H) 5.10 (d, 1 H) 4.15 (s, 3 H) 1.88 (d, 3 H) |
| AD70 | Me | OMe | OH | 4-chloro-5-phenyl Pyridin-2-yl | | 8.54 (s, 1 H) 8.19 (s, 1 H) 7.34-7.64 (m, 5 H) 6.16 (s, 1 H) 5.43 (d, 1 H) 4.16 (s, 3 H) 1.91 (s, 3 H) |
| AD71 | Me | OMe | OH |  | | 8.18 (s, 1 H) 7.92 (s, 1 H) 6.07-6.17 (m, 2 H) 5.80-5.92 (m, 1 H) 4.14 (s, 3 H) 4.08-4.18 (m, 3 H) 2.58 (q, 2 H) 1.92 (s, 3 H) 1.88 (s, 3 H) 1.70 (s, 3 H) 1.18 (t, 3 H) |

TABLE 1-continued
Compounds of the Invention
A = substituted pyrid-2-yl
| Compound Number | R¹ | R² | R³ | A | LC-MS (MH⁺, RT in minutes)ᵃ/ melting pointᶜ °C. | 1H NMR (measured in CDCl₃ unless otherwise indicated) δ |
|---|---|---|---|---|---|---|
| AD72 | Me | OMe | OH | 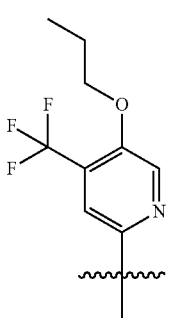 [SMILES: *c1cc(C(F)(F)F)c(OCCC)cn1] | 1.78 Min 347 MH⁺ | |
| AD73 | Me | OMe | OH | 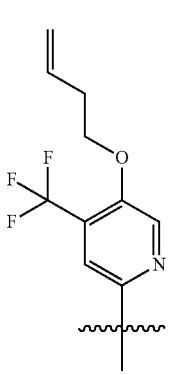 | 1.80 Min 359 MH⁺ | |
| AD74 | Me | OMe | OH | 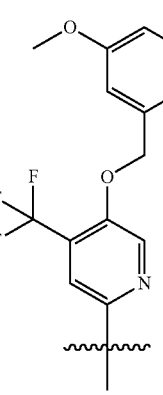 | 1.85 Min 425 MH⁺ | |

TABLE 1-continued
Compounds of the Invention
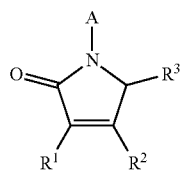
A = substituted pyrid-2-yl
| Compound Number | R¹ | R² | R³ | A | LC-MS (MH⁺, RT in minutes)$^a$/ melting point$^c$ ° C. | 1H NMR (measured in CDCl₃ unless otherwise indicated) δ |
|---|---|---|---|---|---|---|
| AD75 | Me | OMe | OH | 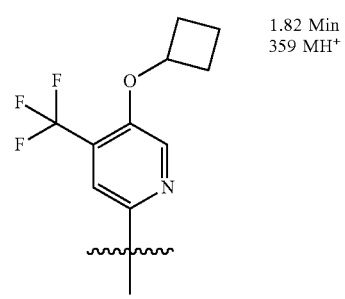 | 1.82 Min 359 MH⁺ | |
| AD76 | Me | OMe | OH | 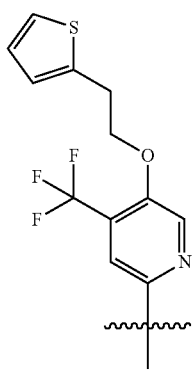 [SMILES: *c1cc(C(F)(F)F)c(OCCc2cccs2)cn1] | 1.90 Min 415 MH⁺ | |
| AD77 | Me | OMe | OH | 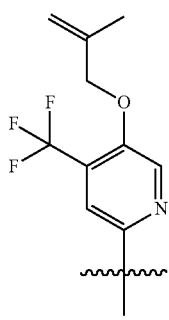 [SMILES: *c1cc(C(F)(F)F)c(OCC(=C)C)cn1] | 1.42 Min 359 MH⁺ | |

TABLE 1-continued
Compounds of the Invention
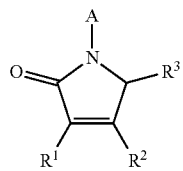
A = substituted pyrid-2-yl
| Compound Number | R¹ | R² | R³ | A | LC-MS (MH⁺, RT in minutes)$^a$/ melting point$^c$ °C. | 1H NMR (measured in CDCl₃ unless otherwise indicated) δ |
|---|---|---|---|---|---|---|
| AD78 | Me | OMe | OH | | 1.97 Min 361 MH⁺ | |
| AD79 | Me | OMe | OH | | 1.67 Min 365 MH⁺ | |
| AD80 | Me | OMe | OH | | 1.82 Min 405 MH⁺ | |

TABLE 1-continued
Compounds of the Invention
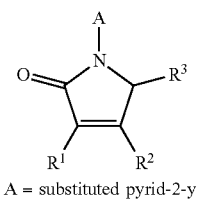
A = substituted pyrid-2-yl
| Compound Number | R¹ | R² | R³ | A | LC-MS (MH$^+$, RT in minutes)$^a$/ melting point$^c$ °C. | 1H NMR (measured in CDCl$_3$ unless otherwise indicated) δ |
|---|---|---|---|---|---|---|
| AD81 | Me | OMe | OH | (benzyloxyethoxy-CF$_3$-pyridyl) | 1.88 Min 439 MH$^+$ | |
| AD82 | Me | OMe | OH | (benzyloxy-CF$_3$-pyridyl) | 1.87 Min 395 MH$^+$ | |
| AD83 | Me | OMe | OH | (methoxypropoxy-CF$_3$-pyridyl) | 1.62 Min 377 MH$^+$ | |

TABLE 1-continued
Compounds of the Invention
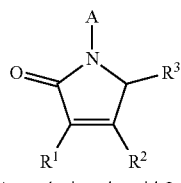
A = substituted pyrid-2-yl
| Compound Number | R¹ | R² | R³ | A | LC-MS (MH⁺, RT in minutes)$^a$/ melting point$^c$ °C. | 1H NMR (measured in CDCl₃ unless otherwise indicated) δ |
|---|---|---|---|---|---|---|
| AD84 | Me | OMe | OH | 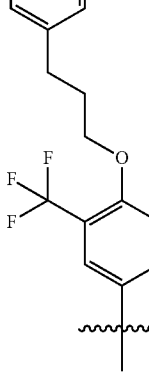 | 2.05 Min 423 MH⁺ | |
| AD85 | Me | OMe | OH | 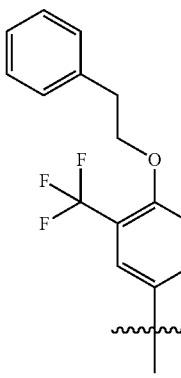 | 1.93 Min 409 MH⁺ | |
| AD86 | Me | OMe | OH | 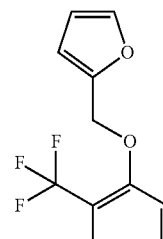 | 1.70 Min 385 MH⁺ | |

TABLE 1-continued
Compounds of the Invention
A = substituted pyrid-2-yl
| Compound Number | R¹ | R² | R³ | A | LC-MS (MH⁺, RT in minutes)$^a$/ melting point$^c$ °C. | 1H NMR (measured in CDCl₃ unless otherwise indicated) δ |
|---|---|---|---|---|---|---|
| AD87 | Me | OMe | OH | 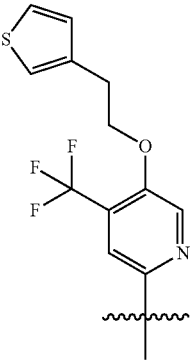 [SMILES: *c1cc(C(F)(F)F)c(OCCc2ccsc2)cn1] | 1.90 Min 415 MH⁺ | |
| AD88 | Me | OMe | OH | 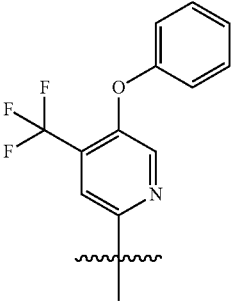 [SMILES: *c1cc(C(F)(F)F)c(Oc2ccccc2)cn1] | 1.87 Min 381 MH⁺ | |
| AD89 | Me | OMe | OH | 4-isopropyl-5-tert-butylamino carbonyl Pyridin-2-yl | | 8.26 (s, 1 H) 8.04 (s, 1 H) 6.04 (s, 1 H) 5.63-5.74 (m, 1 H) 5.53 (s, 1 H) 4.07 (s, 3 H) 3.32 (spt, 1 H) 1.80 (s, 3 H) 1.39 (s, 9 H) 1.19 (dd, 6 H) |
| AD90 | Me | OMe | OH | 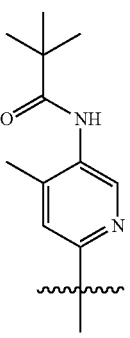 | | (DMSO-d6) 9.01 (s 1 H) 8.04 (s, 1 H) 7.90 (s, 1 H) 6.65-6.81 (m, 1 H) 6.37 (s, 1 H) 4.06 (s, 3 H) 3.31 (s, 4 H) 2.16 (s, 3 H) 1.70 (s, 3 H) 1.24 (s, 9 H) |

TABLE 1-continued

Compounds of the Invention

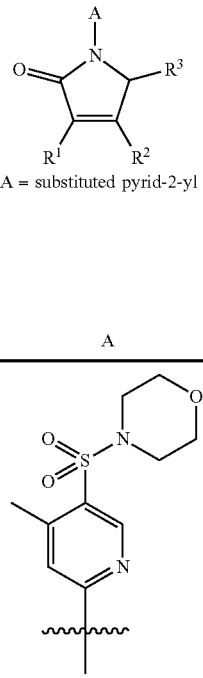

A = substituted pyrid-2-yl

| Compound Number | R¹ | R² | R³ | A | LC-MS (MH⁺, RT in minutes)$^a$/ melting point$^c$ °C. | 1H NMR (measured in CDCl₃ unless otherwise indicated) δ |
|---|---|---|---|---|---|---|
| AD91 | Me | OMe | OH | 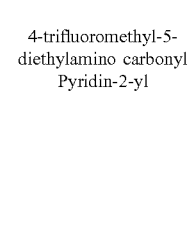 | | 8.68 (1 H, s), 8.35 (s, 1H), 6.18 (dd, 1 H), 5.29 (d, 1 H), 4.17 (s, 3 H), 3.70-3.78 (m, 4 H), 3.10-3.25 (m, 4 H), 2.63 (s, 3H), 1.85-1.92 (m, 3H) |
| AD92 | Me | OMe | OH | 4-trifluoromethyl-5-diethylamino carbonyl Pyridin-2-yl | | 8.72 (s, 1 H) 8.26 (s, 1 H) 6.17 (br. s., 1 H) 4.87-5.24 (m, 1 H) 4.17 (s, 3 H) 3.85 (br. s, 1 H) 3.29 (br. s, 1 H) 3.15 (d, 2 H) 1.90 (d, 3 H) 1.24 (t, 3 H) 1.09 (t, 3 H) |
| AD93 | Me | OMe | OH | 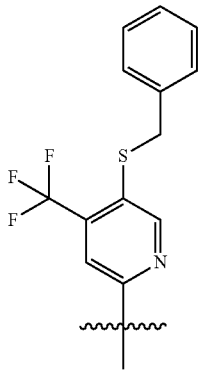 [SMILES: *c1cc(C(F)(F)F)c(SCc2ccccc2)cn1] | | 8.70 (s, 1H), 8.04 (s, 1H), 7.23-7.28 (m, 3 H), 7.14-7.18 (m, 2 H), 6.09 (dd, 1H), 5.02 (d, 1 H), 4.14 (s, 3H), 4.01 (s 2 H), 1.88 (d, 3 H) |
| AD94 | Me | OMe | OH | 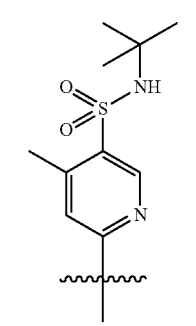 [SMILES: *c1cc(C)c(S(=O)(=O)NC(C)C)cn1] | | 8.78 (s, 1H), 8.19 (s 1H), 6.44 (d, 1H), 4.15 (s, 3H), 2.65 (s 3H), 1.80 (s, 3H), 1.21 (s, 9H). |

TABLE 1-continued

Compounds of the Invention

A = substituted pyrid-2-yl

| Compound Number | R[1] | R[2] | R[3] | A | LC-MS (MH+, RT in minutes)[a]/ melting point[c] °C. | 1H NMR (measured in CDCl$_3$ unless otherwise indicated) δ |
|---|---|---|---|---|---|---|
| AD95 | Me | OMe | OH | | | 8.77 (s, 1H), 8.34 (s, 1H), 6.18 (dd, 1H), 5.35 (d, 1H), 4.40 (d, 1H), 4.16 (s, 3H), 3.47 (dq, 1H), 2.64 (s, 3 H), 1.86-1.92 (m, 3H), 1.14 (d, 3H), 1.11 (d, 3H) |
| AD96 | Me | OMe | OH | | | 8.73 (s, 1H), 8.33 (s, 1H), 6.19 (dd, 1H), 5.37 (d, 1H), 4.74 (t, 1H), 4.16 (s, 3H), 2.96 (qd, 2H), 2.64 (s, 3H), 1.88 (s, 3H), 1.39-1.56 (m, 2H), 1.22-1.38 (m, 2H), 0.86 (t, 3H) |
| AD97 | Me | OMe | OH | | | 8.69 (s, 1H), 8.32 (s 1H), 6.17 (s, 1H), 5.35 (br. s., 1H), 4.16 (s, 3H), 3.17 (t 4H), 2.62 (s, 3H), 1.84-1.94 (m, 3H), 1.63 (dt, 4H), 1.49-1.58 (m, 2H) |

TABLE 1-continued
Compounds of the Invention
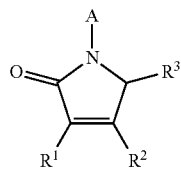
A = substituted pyrid-2-yl
| Compound Number | R¹ | R² | R³ | A | LC-MS (MH⁺, RT in minutes)$^a$/ melting point$^c$ °C. | 1H NMR (measured in CDCl₃ unless otherwise indicated) δ |
|---|---|---|---|---|---|---|
| AD98 | Me | OMe | OH | | | 8.63 (s, 1 H) 8.42 (s, 1 H) 7.27-7.39 (m, 5 H) 6.39-6.54 (m, 1 H) 6.13 (d, 1 H) 5.09 (d, 1 H) 4.59 (d, 2 H) 4.14 (s, 3 H) 1.85 (s, 3 H) |
| AD99 | Me | OMe | OH | | 1.34 Min 350 MH⁺ | |
| AD100 | Me | OMe | OH | | 1.24 Min 355 MH⁺ | |

TABLE 1-continued

Compounds of the Invention

A = substituted pyrid-2-yl

| Compound Number | R¹ | R² | R³ | A | LC-MS (MH⁺, RT in minutes)$^a$/ melting point$^c$ °C. | 1H NMR (measured in CDCl₃ unless otherwise indicated) δ |
|---|---|---|---|---|---|---|
| AD101 | Me | OMe | OH | 4-cyanophenyl on 4-ethylpyridin-2-yl | 1.35 Min 340 MH⁺ | |
| AD102 | Me | OMe | OH | furan-3-yl on 4-ethylpyridin-2-yl | 1.18 Min 315 MH⁺ | |
| AD103 | Me | OMe | OH | 4-methyl-3-nitrophenyl on 4-ethylpyridin-2-yl | 1.49 Min 384 MH⁺ | |

TABLE 1-continued
Compounds of the Invention
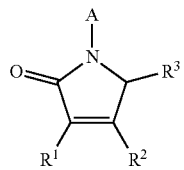
A = substituted pyrid-2-yl
| Compound Number | R¹ | R² | R³ | A | LC-MS (MH$^+$, RT in minutes)$^a$/ melting point$^c$ °C. | 1H NMR (measured in CDCl$_3$ unless otherwise indicated) δ |
|---|---|---|---|---|---|---|
| AD104 | Me | OMe | OH | 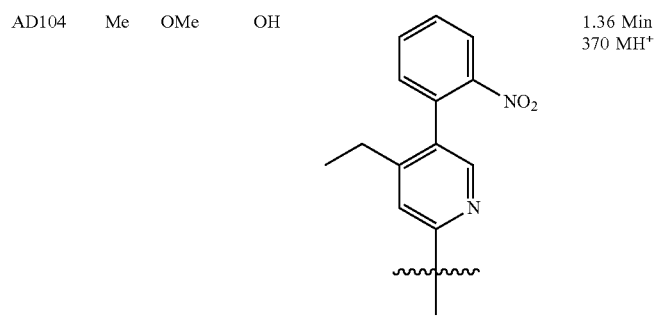 | 1.36 Min 370 MH$^+$ | |
| AD105 | Me | OMe | OH | 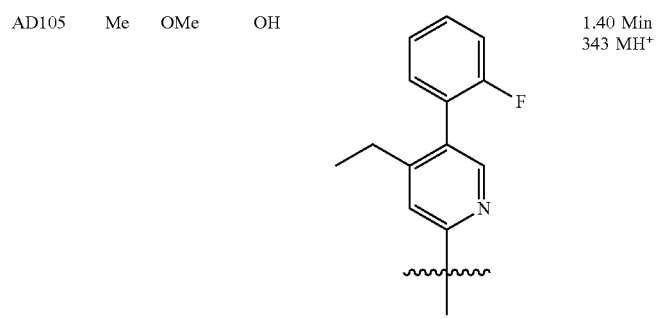 | 1.40 Min 343 MH$^+$ | |
| AD106 | Me | OMe | OH | 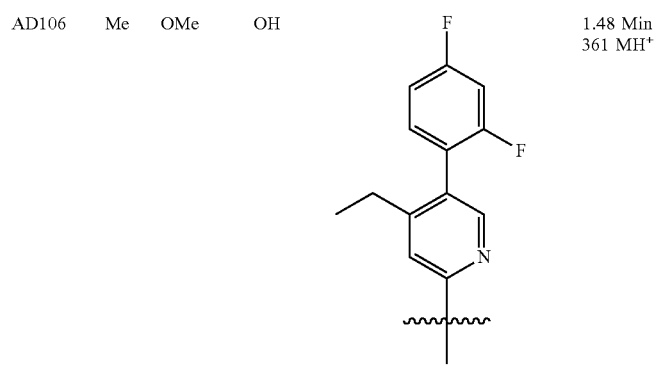 | 1.48 Min 361 MH$^+$ | |

TABLE 1-continued
Compounds of the Invention
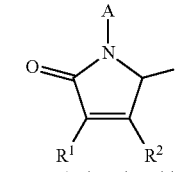
A = substituted pyrid-2-yl
| Compound Number | R¹ | R² | R³ | A | LC-MS (MH⁺, RT in minutes)$^a$/ melting point$^c$ °C. | 1H NMR (measured in CDCl₃ unless otherwise indicated) δ |
|---|---|---|---|---|---|---|
| AD107 | Me | OMe | OH | 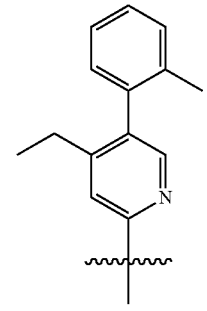 [SMILES: *c1cc(CC)c(-c2ccccc2C)cn1] | 1.68 Min 339 MH⁺ | |
| AD108 | Me | OMe | OH | 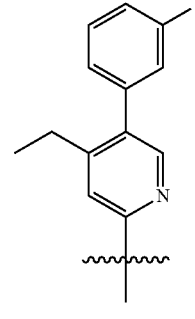 | 1.40 Min 343 MH⁺ | |
| AD109 | Me | OMe | OH | 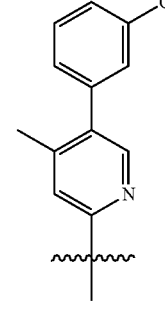 | 1.24 Min 336 MH⁺ | |
| AD110 | Me | OMe | OH | 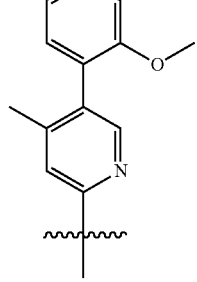 | 1.16 Min 341 MH⁺ | |

TABLE 1-continued
Compounds of the Invention
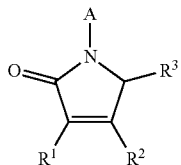
A = substituted pyrid-2-yl
| Compound Number | R[1] | R[2] | R[3] | A | LC-MS (MH+, RT in minutes)[a]/ melting point[c] °C. | 1H NMR (measured in CDCl3 unless otherwise indicated) δ |
|---|---|---|---|---|---|---|
| AD111 | Me | OMe | OH | 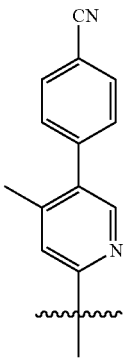 | 1.26 Min 336 MH+ | |
| AD112 | Me | OMe | OH | 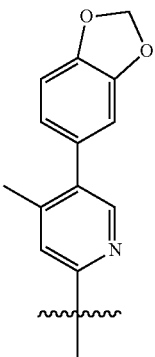 [SMILES: *c1cc(C)c(-c2ccc3c(c2)OCO3)cn1] | 1.18 Min 355 MH+ | |
| AD113 | Me | OMe | OH | 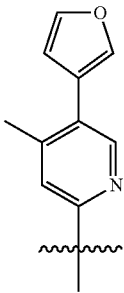 [SMILES: *c1cc(C)c(-c2ccoc2)cn1] | 1.08 Min 301 MH+ | |

TABLE 1-continued
Compounds of the Invention
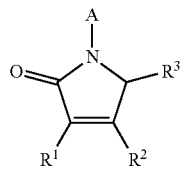
A = substituted pyrid-2-yl
| Compound Number | R¹ | R² | R³ | A | LC-MS (MH⁺, RT in minutes)$^a$/ melting point$^c$ °C. | 1H NMR (measured in CDCl₃ unless otherwise indicated) δ |
|---|---|---|---|---|---|---|
| AD114 | Me | OMe | OH | 3,4,5-trifluorophenyl-4-methylpyrid-2-yl | 1.69 Min 365 MH⁺ | |
| AD115 | Me | OMe | OH | 4-methoxyphenyl-4-methylpyrid-2-yl | 1.18 Min 341 MH⁺ | |
| AD116 | Me | OMe | OH | 4-nitrophenyl-4-methylpyrid-2-yl | 1.36 Min 356 MH⁺ | |

TABLE 1-continued
Compounds of the Invention
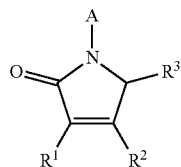
A = substituted pyrid-2-yl
| Compound Number | R¹ | R² | R³ | A | LC-MS (MH⁺, RT in minutes)$^a$/ melting point$^c$ °C. | 1H NMR (measured in CDCl$_3$ unless otherwise indicated) δ |
|---|---|---|---|---|---|---|
| AD117 | Me | OMe | OH | 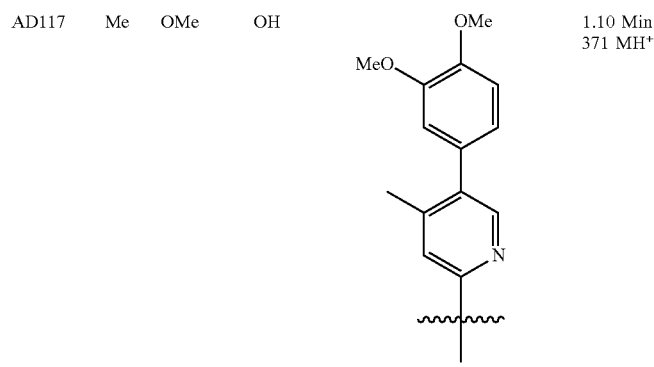 | 1.10 Min 371 MH⁺ | |
| AD118 | Me | OMe | OH | 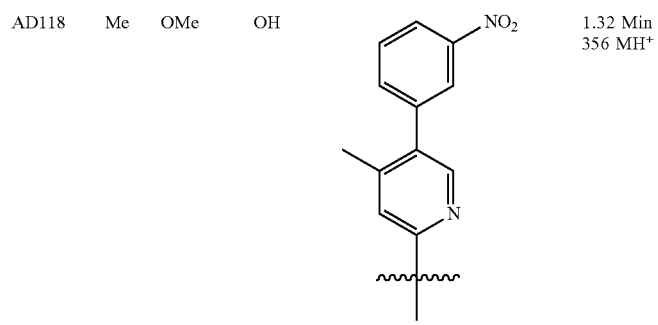 | 1.32 Min 356 MH⁺ | |
| AD119 | Me | OMe | OH | 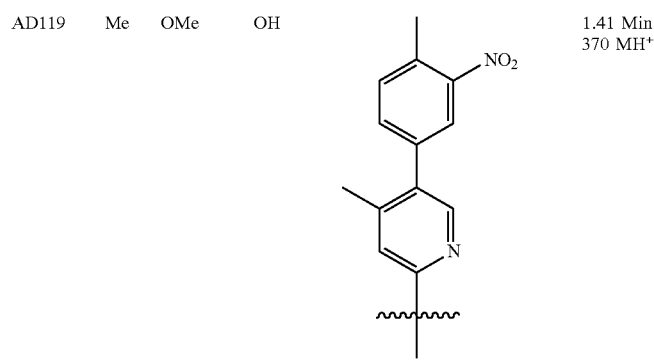 | 1.41 Min 370 MH⁺ | |

TABLE 1-continued
Compounds of the Invention
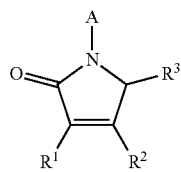
A = substituted pyrid-2-yl
| Compound Number | R¹ | R² | R³ | A | LC-MS (MH⁺, RT in minutes)ᵃ/ melting pointᶜ °C. | 1H NMR (measured in CDCl₃ unless otherwise indicated) δ |
|---|---|---|---|---|---|---|
| AD120 | Me | OMe | OH | 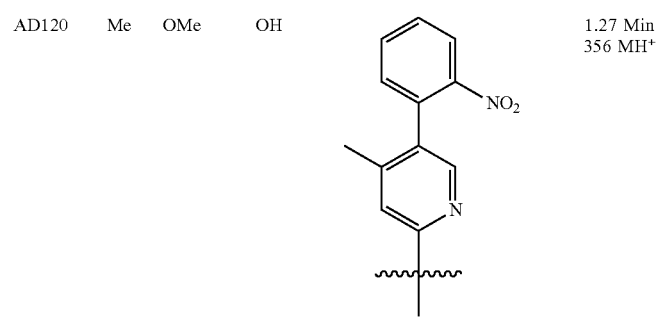 | 1.27 Min 356 MH⁺ | |
| AD121 | Me | OMe | OH | 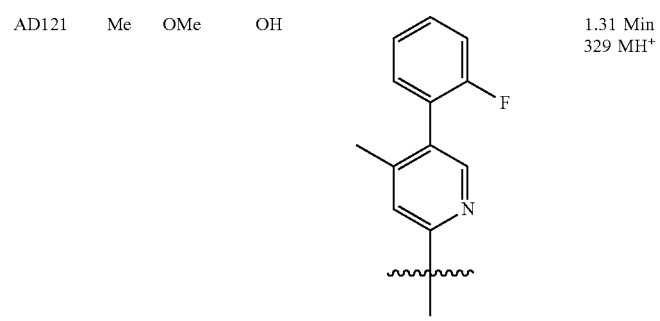 | 1.31 Min 329 MH⁺ | |
| AD122 | Me | OMe | OH | 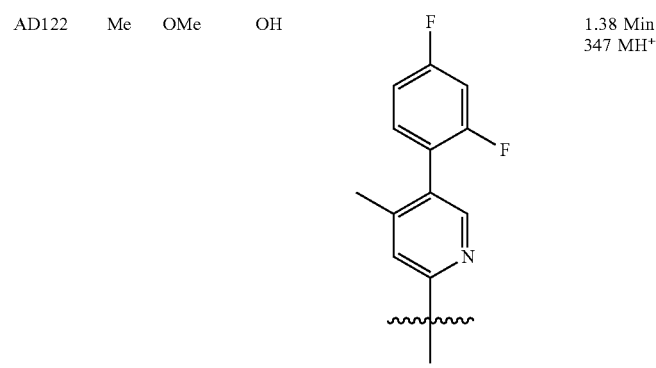 | 1.38 Min 347 MH⁺ | |

TABLE 1-continued
Compounds of the Invention
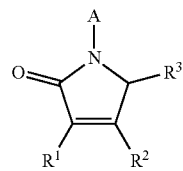
A = substituted pyrid-2-yl
| Compound Number | R¹ | R² | R³ | A | LC-MS (MH⁺, RT in minutes)ᵃ/ melting pointᶜ °C. | 1H NMR (measured in CDCl₃ unless otherwise indicated) δ |
|---|---|---|---|---|---|---|
| AD123 | Me | OMe | OH | 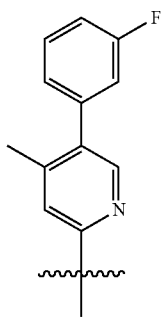 [SMILES: *c1cc(C)c(-c2cccc(F)c2)cn1] | 1.30 Min 313 MH⁺ | |
| AD124 | Me | OMe | OH | 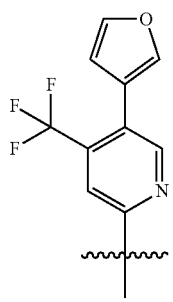 [SMILES: *c1cc(C(F)(F)F)c(-c2ccoc2)cn1] | 1.74 Min 355 MH⁺ | |
| AD125 | Me | OMe | OH | 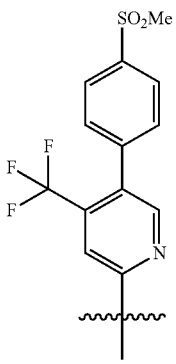 [SMILES: *c1cc(C(F)(F)F)c(-c2ccc(S(C)(=O)=O)cc2)cn1] | 1.45 Min 443 MH⁺ | |

TABLE 1-continued
Compounds of the Invention
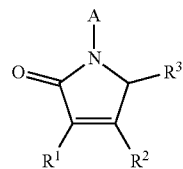
A = substituted pyrid-2-yl
| Compound Number | R¹ | R² | R³ | A | LC-MS (MH$^+$, RT in minutes)$^a$/ melting point$^c$ °C. | 1H NMR (measured in CDCl$_3$ unless otherwise indicated) δ |
|---|---|---|---|---|---|---|
| AD126 | Me | OMe | OH | 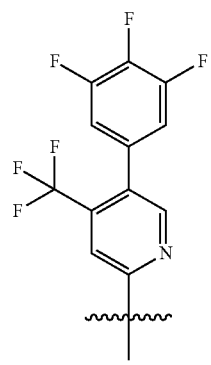 [SMILES: *c1cc(C(F)(F)F)c(-c2cc(F)c(F)c(F)c2)cn1] | 1.98 Min 419 MH$^+$ | |
| AD127 | Me | OMe | OH | 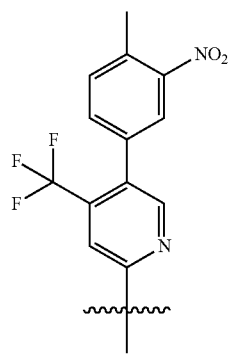 [SMILES: *c1cc(C(F)(F)F)c(-c2ccc(C)c([N+](=O)[O-])c2)cn1] | 1.77 Min 424 MH$^+$ | |
| AD128 | Me | OMe | OH | 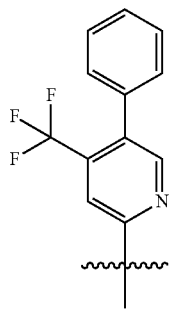 [SMILES: *c1cc(C(F)(F)F)c(-c2ccccc2)cn1] | 1.86 Min 365 MH$^+$ | |

TABLE 1-continued
Compounds of the Invention
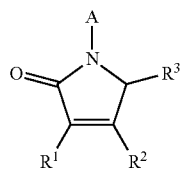
A = substituted pyrid-2-yl
| Compound Number | R¹ | R² | R³ | A | LC-MS (MH+, RT in minutes)$^a$/ melting point$^c$ °C. | 1H NMR (measured in CDCl$_3$ unless otherwise indicated) δ |
|---|---|---|---|---|---|---|
| AD129 | Me | OMe | OH | (2-NO$_2$-phenyl, 4-CF$_3$-pyridyl) | 1.63 Min 410 MH+ | |
| AD130 | Me | OMe | OH | (2-F-phenyl, 4-CF$_3$-pyridyl) | 0.69 Min 383 MH+ | |
| AD131 | Me | OMe | OH | (2,4-diF-phenyl, 4-CF$_3$-pyridyl) | 1.85 Min 401 MH+ | |

TABLE 1-continued

Compounds of the Invention

A = substituted pyrid-2-yl

| Compound Number | R¹ | R² | R³ | A | LC-MS (MH⁺, RT in minutes)$^a$/ melting point$^c$ °C. | 1H NMR (measured in CDCl₃ unless otherwise indicated) δ |
|---|---|---|---|---|---|---|
| AD132 | Me | OMe | OH | 5-(2-methylphenyl)-4-trifluoromethyl-pyridin-2-yl | 1.92 Min 378 MH⁺ | |
| AD133 | Me | OMe | OH | 5-(3-fluorophenyl)-4-trifluoromethyl-pyridin-2-yl | 1.88 Min 383 MH⁺ | |
| AD134 | Me | OMe | OH | 4-chloro-5-(thiophen-3-yl)-pyridin-2-yl | | 8.53 (s, 1 H) 8.27 (s, 1 H) 7.47 (dd, 1 H) 7.42 (dd, 1 H) 7.30 (dd, 1 H) 6.15 (d, 1 H) 5.40 (d, 1 H) 4.16 (s, 3 H) 1.90 (d, 3 H) |
| AE1 | OMe | Br | OH | 4-Trifluoromethyl Pyridin-2-yl | /143.8 | 8.58 (s, 1H); 8.49 (d, 1H); 7.31 (dd, 1H); 6.13 (d, 1H); 5.21 (d, 1H); 4.25 (s, 3H) |
| AE2 | OMe | Br | OH | 4-Tert-butyl Pyridin-2-yl | | 8.32 (d, 1H); 8.19 (d, 1H); 7.08 (dd, 1H); 6.07 (s, 1H); 5.80 (s, 1H); 4.23 (s, 3H); 1.33 (s, 9H) |
| AF1 | OMe | Cl | OH | 4-Tert-butyl Pyridin-2-yl | | 8.32 (dd, 1H); 8.19 (dd, 1H); 7.08 (dd, 1H); 6.05 (s, 1H); 5.77 (s, 1H); 4.22 (s, 3H); 1.33 (s, 9H) |

TABLE 1-continued

Compounds of the Invention

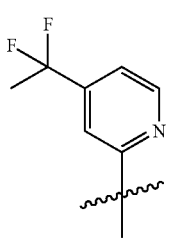 [SMILES: *c1cc(C(C)(F)F)ccn1]

A = substituted pyrid-2-yl

| Compound Number | R¹ | R² | R³ | A | LC-MS (MH+, RT in minutes)[a]/ melting point[c] ° C. | 1H NMR (measured in CDCl₃ unless otherwise indicated) δ |
|---|---|---|---|---|---|---|
| AF2 | OMe | Cl | OH | 4-Trifluoromethyl Pyridin-2-yl | | 8.58 (d, 1H); 8.48 (d, 1H); 7.30 (dd, 1H); 6.10 (d, 1H); 5.17 (d, 1H); 4.24 (s, 3H) |
| AF3 | OMe | Cl | OH | (structure shown) | | 8.42 (d, 1H); 8.38 (d, 1H); 7.21 (dd, 1H); 6.08 (d, 1H); 5.37 (d, 1H); 4.23 (s, 3H); 1.93 (t, 3H) |

TABLE 2

Compounds of the Invention

A = substituted pyridazin-3-yl

| Compound Number | R¹ | R² | R³ | A | LC-MS (MH+, RT in minutes)[a]/ melting point[c] ° C. | 1H NMR (measured in CDCl₃ unless otherwise indicated) δ |
|---|---|---|---|---|---|---|
| BA1 | Me | Cl | OH | 5-Methyl-6-methoxy Pyridazin-3-yl | 0.61 mins 270, 272 MH+ | 8.40 (s, 1H), 6.20 (s, 1H), 5.33 (d, br, 1H), 4.11 (s, 3H), 2.28 (s, 3H), 1.97 (s, 3H) |
| BB1 | Me | Br | OH | 5-Methyl-6-methoxy Pyridazin-3-yl | 0.59 mins 314, 316 MH+ | 8.39 (s, 1H), 6.22 (s, br, 1H), 5.35 (d, 1H), 4.12 (s, 3H), 2.28 (s, 3H), 1.97 (s, 3H) |
| BD1 | Me | OMe | OH | 5-Tert-butyl Pyridazin-3-yl | /160-2 | 8.92 (d, 1H); 8.64 (d, 1H); 6.34 (d, 1H); 5.50 (d, 1H); 4.17 (s, 3H); 1.89 (s, 3H); 1.37 (s, 9H) |
| BD2 | Me | OMe | OH | 5-Tert-butyl-6-chloro Pyridazin-3-yl | | 8.79 (s, 1H); 6.30-6.31 (d, 1H); 5.20-5.21 (d, 1H); 4.17 (s, 3H); 1.89 (s, 3H); 1.50 (s, 9H) |
| BD3 | Me | OMe | OH | 6-Chloropyridazin-3-yl | LCMS 0.46 mins ES+ 238/240 [M − H2O + H+], 256/257 MH+, 279/281 [M + Na+]/180 to 189 dec | 8.68 (d, 1H), 7.50 (d, 1H), 6.32 (d, 1H), 5.15 (d, 1H), 4.17 (s, 3H), 1.88 (s, 3H) |

TABLE 2-continued

Compounds of the Invention

A = substituted pyridazin-3-yl

| Compound Number | R¹ | R² | R³ | A | LC-MS (MH⁺, RT in minutes)$^a$/ melting point$^c$ ° C. | 1H NMR (measured in CDCl₃ unless otherwise indicated) δ |
|---|---|---|---|---|---|---|
| BD4 | Me | OMe | OH | (4-(2-chloro-1,1-dimethylethyl)-6-chloropyridazin-3-yl) | /124-5 | 8.82 (s, 1H); 6.31-6.32 (s, 1H); 5.13-5.14 (d, 1H); 4.17 (s, 3H); 3.99-4.12 (q, 2H); 1.89 (s, 3H); 1.55 (s, 6H) |
| BD5 | Me | OMe | OH | (4-isopropyl-6-methoxypyridazin-3-yl) | | 8.49 (s, 1H), 6.25 (m, 1H), 5.38 (m, 1H), 4.15 (s, 3H), 4.10 (s, 3H), 3.14 (septet, 1H), 1.89 (s, 3H), 1.26 (dm, 6H) |
| BD6 | Me | OMe | OH | (6-allyloxy-4-isopropylpyridazin-3-yl) | | 8.34 (s, 1H), 5.97 (m, 1H), 5.97 (m, 1H), 5.28 (m, 1H), 5.26 (m, 1H), 4.88 (m, 1H), 4.54 (m, 1H), 4.52 (m, 1H), 4.14 (s, 3H) 3.25 (septet, 1H), 1.88 (s, 3H), 1.24 (dm, 6H) |
| BD7 | Me | OMe | OH | (6-ethoxy-4-isopropylpyridazin-3-yl) | 2.48 min MH⁺ 308 | |

TABLE 2-continued

Compounds of the Invention

A = substituted pyridazin-3-yl

| Compound Number | R$^1$ | R$^2$ | R$^3$ | A | LC-MS (MH$^+$, RT in minutes)$^a$/ melting point$^c$ °C. | 1H NMR (measured in CDCl$_3$ unless otherwise indicated) δ |
|---|---|---|---|---|---|---|
| BD8 | Me | OMe | OH | 6-chloro-5-tert-butyl-4-fluoro-pyridazin-3-yl | | 8.83 (s, 1H) 6.26 (d, 1H) 5.18 (d, 1H) 4.10 (s, 3 H) 1.82 (s, 3H) 1.73-1.81 (m, 6H) |
| BD9 | Me | OMe | OH | 5-tert-butyl-6-(4-fluorophenyl)pyridazin-3-yl | | 8.84 (s, 1H), 7.37-7.32(m, 2H), 7.17-7.13 (m, 2H), 6.36 (d, 1H), 5.48 (d, 1H), 4.18 (s, 3H), 1.92 (s, 3H), 1.23 (s, 9H) |
| BD10 | Me | OMe | OH | 5-tert-butyl-6-methoxy-pyridazin-3-yl | | 8.58 (s, 1H), 6.26 (, 1H), 5.33 (br. s, 1H), 4.15 (s, 3H), 4.12 (s, 3H), 1.89 (s, 3H), 1.39 (s, 9H) |
| BD11 | Me | OMe | OH | 5-Methyl-6-chloro Pyridazin-3-yl | | 8.59 (s, 1H), 6.30 (m, 1H), 5.20 (d, 1H), 4.17 (s, 3H), 2.43 (s, 3H), 1.89 (s, 3H) |
| BD12 | Me | OMe | OH | 5-tert-butyl-6-(3,3-difluoroazetidin-1-yl)pyridazin-3-yl | | 8.63 (s, 1H), 6.10 (m, 1H), 5.14 (d, 1H), 4.49-4.40 (m, 4H), 4.05 (s, 3H), 2.10 (s, 3H), 1.45 (s, 9H) |

TABLE 2-continued

Compounds of the Invention

A = substituted pyridazin-3-yl

| Compound Number | R¹ | R² | R³ | A | LC-MS (MH⁺, RT in minutes)$^a$/ melting point$^c$ ° C. | 1H NMR (measured in CDCl₃ unless otherwise indicated) δ |
|---|---|---|---|---|---|---|
| BD13 | Me | OMe | OH | *N-tert-butyl pyridazine-3-carboxamide* | | 8.72 (d, 1H), 8.24 (d, 1H), 7.78 (br. s, 1H), 6.36 (d, 1H), 5.22 (d, 1H), 4.16 (s, 3H), 1.87 (s, 3H), 1.48 (s, 9H) |
| BD14 | Me | OMe | OH | *4-tert-butyl-3-(3-cyanophenyl)pyridazinyl* | | 8.88 (s, 1H), 7.79-7.74 (m, 1H), 7.68 (m, 1H), 7.64-7.56 (m, 2H), 6.36 (d, 1H), 5.36 (d, 1H), 4.18 (s, 3H), 1.92 (s, 3H), 1.22 (s, 9H) |

TABLE 3

Compounds of the Invention

A = substituted pyrimidin-4-yl

| Compound Number | R¹ | R² | R³ | A | LC-MS (MH⁺, RT in minutes)$^a$/melting point$^c$ ° C. | 1H NMR (measured in CDCl₃ unless otherwise indicated) δ |
|---|---|---|---|---|---|---|
| CA1 | Me | Cl | OH | 6-Tert-butyl Pyrimidin-4-yl | | 8.84 (s, 1H); 8.30 (s, 1H); 6.12-6.13 (d, 1H); 5.31-5.32 (d, 1H); 1.98 (s, 3H); 1.36 (s, 9H) |
| CA2 | Me | Cl | OH | 6-Trifluoromethyl Pyrimidin-4-yl | LCMS 0.75 mins ES+ 294/296 MH+/142 to 145 | 9.04 (s, 1H), 8.64 (s, 1H) 6.19 (d, 1H), 4.90 (d, 1H), 2.01 (s, 3H) |

TABLE 3-continued

Compounds of the Invention

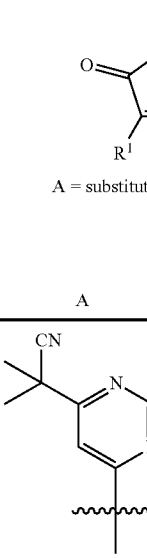

A = substituted pyrimidin-4-yl

| Compound Number | R¹ | R² | R³ | A | LC-MS (MH⁺, RT in minutes)$^a$/melting point$^c$ ° C. | 1H NMR (measured in CDCl$_3$ unless otherwise indicated) δ |
|---|---|---|---|---|---|---|
| CA3 | Et | Cl | OH | 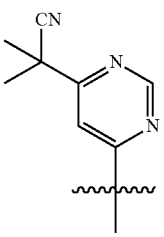 [SMILES: *c1cc(C(C)(C)C#N)ncn1] | | 8.89 (s, 1H), 8.52 (s, 1H), 6.13 (s, 1H), 5.1 (br s, 1H), 2.44 (m, 2H), 1.77 (s, 6H), 1.18 (t, 3H) |
| CA4 | Pr | Cl | OH | 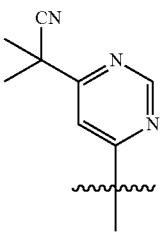 [SMILES: *c1cc(C(C)(C)C#N)ncn1] | | 8.94 (s, 1H), 8.57 (s, 1H), 6.19 (s, 1H), 2.44 (t, 2H), 1.80 (s, 6H), 1.66 (m, 2H), 1.04 (t, 3H) |
| CB1 | Me | Br | OH | 6-Trifluoromethyl Pyrimidin-4-yl | LCMS 0.76 mins ES+ 338/340 MH+/166 to 168 | 9.03 (s, 1H), 8.63 (s, 1H), 6.22 (d, 1H), 4.91 (d, 1H), 2.00 (s, 3H) |
| CB2 | Et | Br | OH | CN (same as above structure) | | 8.90 (s, 1H), 8.52 (s, 1H), 6.16 (s, 1H), 2.44 (m, 2H), 1.77 (s, 6H), 1.17 (t, 3H) |
| CD1 | Me | OMe | OH | 6-(Piperidin-1-yl) Pyrimidin-4-yl | /122.9-132.5 | 8.28 (s, 1H); 7.51 (s, 1H); 6.08 (s, 1H); 5.75 (s, 1H); 4.13 (s, 3H), 3.63 (t, 4H); 1.85 (s, 3H) 1.68 (m, 2H); 1.61 (m, 4H) |
| CD2 | Me | OMe | OH | 6-Chloro Pyrimidin-4-yl | /176.0-178.9 | 8.63 (d, 1H); 8.35 (d, 1H); 6.14 (dt, 1H); 4.99 (d, 1H); 4.17 (s, 3H); 1.88 (d, 3H) |
| CD3 | Me | OMe | OH | 6-Tert-butyl Pyrimidin-4-yl | | 8.78 (s, 1H); 8.33 (s, 1H); 6.15-6.16 (d, 1H); 5.34-5.35 (d, 1H); 4.16 (s, 3H); 1.88 (s, 3H); 1.35 (s, 9H) |
| CD4 | Me | OMe | OH | 6-Trifluoromethyl Pyrimidin-4-yl | LCMS 0.66 mins ES+ 290 MH+/135 to 137 | 8.96 (s, 1H), 8.67 (s, 1H), 6.21 (d, 1H), 4.98 (d, 1H), 4.20 (s, 3H), 1.91 (s, 3H) |
| CD5 | Me | OMe | OH | 6-Bromo Pyrimidin-4-yl | /168-173 | 8.58 (d, 1H); 8.53 (d, 1H); 6.13 (dd, 1H); 4.97 (d, 1H); 4.17 (s, 3H); 1.88 (d, 3H) |
| CD6 | Me | OMe | OH | 6-(N-methyl-N-ethyl-amino) Pyrimidin-4-yl | /108-112 | 8.29 (s, 1H), 7.39 (s, 1H); 6.09 (s, 1H); 5.78 (s, 1H); 4.13 (s, 3H); 3.58 (br s, 2H); 3.06 (br s, 3H); 1.86 (s, 3H) 1.18 (t, 3H) |
| CD7 | Me | OMe | OH | 6-(N,N-dimethyl-amino) Pyrimidin-4-yl | /149-152 | 8.30 (d, 1H); 7.40 (d, 1H); 6.09 (s, 1H); 5.76 (s, 1H); 4.13 (s, |

TABLE 3-continued

Compounds of the Invention

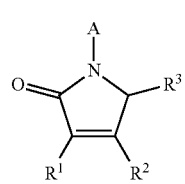

A = substituted pyrimidin-4-yl

| Compound Number | R¹ | R² | R³ | A | LC-MS (MH⁺, RT in minutes)$^a$/melting point$^c$ ° C. | 1H NMR (measured in CDCl₃ unless otherwise indicated) δ |
|---|---|---|---|---|---|---|
| | | | | | | 3H); 3.12 (br s, 6H); 1.86 (s, 3H) |
| CD8 | Me | OMe | OH | (structure with CN and pyrimidine) | | 8.83 (s, 1H), 8.51 (s, 1H), 6.17 (d, 1H), 5.11 (d, 1H), 4.17 (s, 3H), 1.88 (s, 3H), 1.75 (s, 6H) |
| CE1 | Br | OMe | OH | 6-Tert-butyl Pyrimidin-4-yl | | 8.85 (d, 1H); 8.24 (d, 1H); 6.10 (d, 1H); 5.28 (d, 1H); 4.23 (s, 3H); 1.6 (s, 9H) |
| CF1 | Cl | OMe | OH | 6-Tert-butyl Pyrimidin-4-yl | | 8.85 (d, 1H); 8.25 (d, 1H); 6.08 (d, 1H); 5.28 (d, 1H); 4.22 (s, 3H); 1.36 (s, 9H) |

TABLE 4

Compounds of the Invention

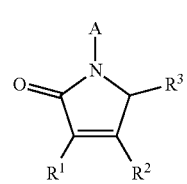

A = substituted pyrimidin-2-yl

| Compound Number | R¹ | R² | R³ | A | LC-MS (MH⁺, RT in minutes)$^a$/melting point$^c$ ° C. | 1H NMR (measured in CDCl₃ unless otherwise indicated) δ |
|---|---|---|---|---|---|---|
| DA1 | Me | Cl | OH | 4-Tert-butyl Pyrimidin-2-yl | | 1.36 (9H, s); 1.99 (3H, s); 5.44 (1H, d); 6.07 (1H, d); 7.09-7.10 (1H, d); 8.63-8.64 (1H, d) |
| DD1 | Me | OMe | OH | 4-Tert-butyl Pyrimidin-2-yl | | 8.59-8.61 (d, 1H); 7.02-7.03 (d, 1H); 6.06 (d, 1H); 5.52-5.53 (d, 1H); 4.16 (s, 3H); 1.93 (s, 3H); 1.35 (s, 9H) |
| DD2 | Me | OMe | OH | 4-(N,N-dimethylamino) Pyrimidin-2-yl | /155-157 | 1.89 (3H, s); 3.15 (6H, br s); 4.13 (3H, s); 5.87 (1H, br s); 5.99 (1H, s); 6.14-6.15 (1H, d); 8.03-8.04 (1H, d) |
| DD3 | Me | OMe | OH | 4-(N,N-dimethylamino)-5-chloro Pyrimidin-2-yl | /170-173 | 1.89 (3H, s); 3.31 (6H, s); 4.13 (3H, s); 5.41-5.42 (1H, d); 5.96 (1H, s); 8.01 (1H, s) |

$^a$Method A used for analysis unless otherwise indicated.
$^b$Method B used for analysis.

Example 30: Post-Emergence Herbicidal Activity

Seeds of a variety of test species were sown in standard soil in pots. After 8 days cultivation (post-emergence) under controlled conditions in a glasshouse (at 24/16° C., day/ night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant, NC=not captured). Results are shown in Table 5.

TABLE 5

Application post-emergence

| Compound Number | Rate (g/ha) | ABUTH | SOLNI | AMARE | SETFA | ALOMY | ECHCG | ZEAMX |
|---|---|---|---|---|---|---|---|---|
| AA1  | 1,000 | 5 |   | 5 | 5 | 3 | 5 | 1 |
| AA2  | 1,000 | 4 |   | 5 | 4 | 2 | 2 | 2 |
| AA4  | 1,000 | 1 |   | 1 | 1 | 1 | 0 | 2 |
| AA7  | 1,000 | 2 |   | 5 | 2 | 1 | 4 | 0 |
| AA8  | 1,000 | 3 |   | 5 | 4 | 1 | 4 | 0 |
| AA9  | 1,000 | 4 |   | 4 | 1 | 2 | 1 | 1 |
| AA10 | 1,000 | 0 |   | 3 | 2 | 1 | 1 | 1 |
| AA13 | 1,000 | 5 |   | 4 | 4 | 3 | 4 | 0 |
| AA16 | 1,000 | 0 |   | 0 | 3 | 1 | 1 | 1 |
| AA20 | 1,000 | 1 |   | 0 | 1 | 1 | 1 | 0 |
| AA25 | 1,000 | 1 |   | 5 | 3 | 2 | 3 | 1 |
| AA26 | 1,000 | 1 |   | 5 | 3 | 2 | 3 | 0 |
| AA31 | 1,000 |   | 5 | 5 | 3 | 1 | 2 | 0 |
| AA32 | 1,000 |   | 2 | 0 | 2 | 0 | 0 | 0 |
| AA33 | 1,000 |   | 5 | 5 | 3 | 1 | 2 | 0 |
| AA35 | 1,000 |   | 5 | 5 | 4 | 2 | 4 | 0 |
| AA36 | 1,000 |   | 3 | 4 | 1 | 1 | 2 | 0 |
| AA38 | 1,000 | 1 |   | 4 | 1 | 1 | 1 | 0 |
| AA39 | 1,000 | 3 |   | 5 | 4 | 2 | 3 | 2 |
| AA40 | 1,000 | 2 |   | 4 | 1 | 2 | 4 | 1 |
| AA41 | 1,000 | 0 |   | 0 | 0 | 0 | 3 | 2 |
| AA42 | 1,000 | 3 |   | 3 | 0 | 1 | 0 | 1 |
| AA43 | 1,000 | 2 |   | 2 | 3 | 1 | 5 | 1 |
| AA44 | 1,000 | 1 |   | 3 | 2 | 1 | 1 | 1 |
| AA45 | 1,000 | 2 |   | 3 | 2 | 2 | 1 | 1 |
| AA46 | 1,000 | 5 |   | 5 | 3 | 3 | 3 | 0 |
| AA47 | 1,000 | 1 |   | 0 | 3 | 1 | 2 | 1 |
| AA48 | 1,000 | 4 |   | 5 | 4 | 1 | 3 | 0 |
| AA49 | 1,000 | 3 |   |   | 3 | 2 | 1 | 0 |
| AA50 | 1,000 | 3 |   | 2 | 3 | 2 | 3 | 1 |
| AB1  | 1,000 | 3 |   | 5 | 4 | 2 | 3 | 0 |
| AD2  | 1,000 | 5 |   | 5 | 5 | 5 | 5 | 2 |
| AD3  | 1,000 | 1 |   | 4 | 0 | 0 | 0 | 1 |
| AD4  | 1,000 | 5 |   | 5 | 5 | 5 | 5 | 2 |
| AD5  | 1,000 | 5 |   | 5 | 4 | 4 | 4 | 2 |
| AD7  | 1,000 | 5 |   | 5 | 5 | 5 | 5 | 3 |
| AD9  | 1,000 | 5 |   | 5 | 5 | 4 | 5 | 2 |
| AD10 | 1,000 | 5 |   | 5 | 5 | 5 | 5 | 2 |
| AD11 | 1,000 | 5 |   | 5 | 5 | 4 | 5 | 3 |
| AD12 | 1,000 | 5 |   | 5 | 4 | 4 | 5 | 2 |
| AD13 | 1,000 | 5 |   | 5 | 5 | 5 | 5 | 1 |
| AD14 | 1,000 | 5 |   | 4 | 5 | 3 | 5 | 1 |
| AD15 | 1,000 | 3 |   | 5 | 5 | 3 | 4 | 2 |
| AD16 | 1,000 | 5 |   | 4 | 5 | 4 | 5 | 1 |
| AD18 | 1,000 | 4 |   | 1 | 1 | 3 | 4 | 0 |
| AD19 | 1,000 | 5 |   | 5 | 5 | 4 | 5 | 3 |
| AD20 | 1,000 | 4 |   | 5 | 5 | 4 | 4 | 0 |
| AD21 | 1,000 | 5 |   | 5 | 4 | 2 | 5 | 0 |
| AD23 | 1,000 | 5 |   | 1 | 5 | 4 | 5 | 2 |
| AD24 | 1,000 | 5 |   | 5 | 5 | 4 | 4 | 1 |
| AD25 | 1,000 | 1 |   | 2 | 2 | 1 | 1 | 1 |
| AD26 | 1,000 | 5 |   | 5 | 4 | 4 | 5 | 2 |
| AD27 | 1,000 | 5 |   | 5 | 4 | 4 | 5 | 2 |
| AD28 | 1,000 | 5 |   | 5 | 5 | 4 | 5 | 4 |
| AD29 | 1,000 | 0 |   | 0 | 0 | 1 | 0 | 1 |
| AD30 | 1,000 | 5 |   | 5 | 4 | 5 | 5 | 1 |
| AD31 | 1,000 | 5 |   | 5 | 4 | 5 | 5 | 1 |
| AD33 | 1,000 | 2 |   | 1 | 2 | 1 | 3 | 0 |
| AD34 | 1,000 | 5 |   | 5 | 5 | 5 | 5 | 0 |
| AD35 | 1,000 |   | 5 | 5 | 4 | 3 | 3 | 0 |
| AD37 | 1,000 | 4 |   | 5 | 2 | 3 | 3 | 0 |
| AD38 | 1,000 | 5 |   | 5 | 5 | 5 | 5 | 0 |
| AD39 | 1,000 | 4 |   | 2 | 4 | 4 | 4 | 0 |
| AD40 | 1,000 | 5 |   | 5 | 5 | 5 | 5 | 3 |
| AD42 | 1,000 | 5 |   | 5 | 5 | 4 | 5 | 2 |
| AD44 | 1,000 | 5 |   | 5 | 5 | 3 | 4 | 1 |
| AD45 | 1,000 | 5 |   | 5 | 3 | 4 | 5 | 1 |

TABLE 5-continued

Application post-emergence

| Compound Number | Rate (g/ha) | ABUTH | SOLNI | AMARE | SETFA | ALOMY | ECHCG | ZEAMX |
|---|---|---|---|---|---|---|---|---|
| AD47 | 1000 | 5 | | 5 | 4 | 3 | 3 | 0 |
| AD48 | 1000 | 5 | | 5 | 5 | 4 | 4 | 2 |
| AD49 | 1000 | 5 | | 5 | 5 | 2 | 2 | 2 |
| AD50 | 1000 | 5 | | 5 | 5 | 4 | 4 | 1 |
| AD51 | 1000 | 5 | | 5 | 5 | 4 | 5 | 1 |
| AD52 | 1000 | 5 | | 4 | 5 | 5 | 5 | 1 |
| AD53 | 1000 | 5 | | 5 | 5 | 5 | 5 | 5 |
| AD54 | 1000 | 5 | | 5 | 5 | 5 | 5 | 5 |
| AD55 | 1000 | 5 | | 5 | 5 | 5 | 5 | 3 |
| AD56 | 1000 | 5 | | 5 | 5 | 5 | 5 | 0 |
| AD57 | 1000 | 5 | | 5 | 5 | 4 | 5 | 1 |
| AD58 | 1000 | 5 | | 5 | 5 | 4 | 5 | 2 |
| AD59 | 1,000 | 5 | | 5 | 5 | 4 | 4 | 1 |
| AD60 | 1,000 | 5 | | 5 | 4 | 2 | 1 | 1 |
| AD61 | 1,000 | 5 | | 5 | 4 | 1 | 3 | 1 |
| AD62 | 1,000 | 4 | | 5 | 5 | 3 | 3 | 0 |
| AD63 | 1,000 | 5 | | 5 | 5 | 3 | 3 | 1 |
| AD64 | 1,000 | 4 | | 2 | 5 | 1 | 3 | 1 |
| AD65 | 1,000 | 4 | | 5 | 5 | 2 | 4 | 1 |
| AD66 | 1,000 | 4 | | 5 | 5 | 1 | 4 | 0 |
| AD67 | 1,000 | 5 | | 5 | 5 | 4 | 5 | 1 |
| AD68 | 1,000 | 3 | | 5 | 5 | 1 | 4 | 1 |
| AD69 | 1,000 | 0 | | 4 | 5 | 2 | 3 | 1 |
| AD70 | 250 | 4 | | 5 | 3 | 3 | 1 | 1 |
| AD71 | 1,000 | 4 | | 5 | 5 | 2 | 3 | 2 |
| AD72 | 1,000 | 5 | | 5 | 5 | 5 | 5 | 2 |
| AD73 | 1,000 | 5 | | 5 | 5 | 4 | 4 | 1 |
| AD74 | 1,000 | 3 | | 5 | 5 | 2 | 2 | 1 |
| AD75 | 250 | 5 | | 5 | 4 | 4 | 2 | 1 |
| AD76 | 250 | 4 | | 4 | 3 | 2 | 1 | 1 |
| AD77 | 250 | 5 | | 5 | 4 | 3 | 1 | 0 |
| AD78 | 1,000 | 4 | | 5 | 5 | 3 | 5 | 2 |
| AD79 | 1,000 | 5 | | 5 | 5 | 5 | 5 | 2 |
| AD80 | 1,000 | 4 | | 5 | 5 | 3 | 4 | 1 |
| AD81 | 250 | 5 | | 5 | 3 | 2 | 2 | 1 |
| AD82 | 1,000 | 4 | | 5 | 5 | 2 | 3 | 1 |
| AD83 | 1,000 | 5 | | 5 | 5 | 4 | 5 | 1 |
| AD84 | 1,000 | 2 | | 5 | 4 | 1 | 2 | 1 |
| AD85 | 250 | 5 | | 5 | 4 | 2 | 2 | 1 |
| AD86 | 250 | 4 | | 5 | 3 | 2 | 1 | 0 |
| AD87 | 250 | 4 | | 5 | 3 | 3 | 2 | 1 |
| AD88 | 1,000 | 5 | | 5 | 5 | 3 | 4 | 1 |
| AD89 | 1,000 | 5 | | 5 | 5 | 5 | 5 | 3 |
| AD90 | 1000 | 5 | | 5 | 5 | 5 | 5 | 2 |
| AD91 | 1000 | 0 | | 2 | 0 | 0 | 0 | 2 |
| AD92 | 1000 | 5 | | 4 | 4 | 4 | 5 | 3 |
| AD93 | 1000 | 3 | | 4 | 4 | 2 | 3 | 0 |
| AD94 | 1000 | 1 | | 0 | 1 | 1 | 1 | 0 |
| AD95 | 1000 | 5 | | 5 | 5 | 4 | 4 | 0 |
| AD96 | 1000 | 3 | | 5 | 5 | 4 | 4 | 0 |
| AD97 | 1000 | 0 | | 0 | 0 | 0 | 0 | 0 |
| AD98 | 1000 | 5 | | 5 | 4 | 4 | 4 | 1 |
| AD99 | 1000 | 5 | | 5 | 4 | 1 | 5 | 1 |
| AD100 | 1000 | 4 | | 5 | 4 | 0 | 0 | 1 |
| AD101 | 1000 | 5 | | 5 | 4 | 2 | 3 | 0 |
| AD102 | 1000 | 4 | | 5 | 4 | 3 | 3 | 1 |
| AD103 | 1000 | 4 | | 5 | 4 | 3 | 4 | 1 |
| AD104 | 1000 | 5 | | 5 | 4 | 2 | 2 | 0 |
| AD105 | 1000 | 5 | | 5 | 4 | 2 | 3 | 1 |
| AD106 | 1000 | 5 | | 5 | 4 | 2 | 4 | 0 |
| AD107 | 1000 | 5 | | 5 | 3 | 2 | 2 | 1 |
| AD108 | 1000 | 5 | | 5 | 5 | 3 | 3 | 0 |
| AD109 | 1000 | 5 | | 5 | 5 | 3 | 5 | 1 |
| AD110 | 1000 | 5 | | 5 | 2 | 2 | 1 | 0 |
| AD111 | 1000 | 5 | | 5 | 4 | 2 | 1 | 1 |
| AD112 | 1000 | 4 | | 5 | 3 | 2 | 3 | 1 |
| AD113 | 1000 | 3 | | 5 | 1 | 2 | 2 | 1 |
| AD114 | 1000 | 4 | | 5 | 3 | 2 | 1 | 0 |
| AD115 | 1000 | 5 | | 5 | 1 | 2 | 1 | 1 |
| AD116 | 1000 | 2 | | 5 | 1 | 0 | 0 | 1 |
| AD117 | 1000 | 5 | | 5 | 4 | 2 | 1 | 0 |
| AD118 | 1000 | 5 | | 5 | 4 | 2 | 2 | 0 |
| AD119 | 1000 | 2 | | 5 | 1 | 2 | 1 | 0 |
| AD120 | 1000 | 5 | | 5 | 4 | 2 | 4 | 0 |
| AD121 | 1000 | 5 | | 5 | 5 | 3 | 3 | 1 |

TABLE 5-continued

| Application post-emergence | | | | | | | | |
|---|---|---|---|---|---|---|---|---|
| Compound Number | Rate (g/ha) | ABUTH | SOLNI | AMARE | SETFA | ALOMY | ECHCG | ZEAMX |
| AD122 | 1000 | 5 | | 5 | 4 | 3 | 4 | 0 |
| AD123 | 1000 | 5 | | 5 | 5 | 3 | 3 | 1 |
| AD124 | 1000 | 2 | | 5 | 4 | 2 | 2 | 0 |
| AD125 | 1000 | 4 | | 5 | 4 | 4 | 4 | 1 |
| AD126 | 1000 | 5 | | 5 | 5 | 3 | 3 | 1 |
| AD127 | 1000 | 2 | | 5 | 4 | 1 | 4 | 4 |
| AD128 | 1000 | 5 | | 5 | 5 | 3 | 5 | 2 |
| AD129 | 1000 | 5 | | 5 | 4 | 2 | 4 | 2 |
| AD131 | 1000 | 5 | | 5 | 4 | 2 | 4 | 1 |
| AD132 | 1000 | 5 | | 5 | 5 | 2 | 4 | 2 |
| AD133 | 1000 | 5 | | 5 | 4 | 2 | 4 | 3 |
| AD134 | 1000 | 3 | | 5 | 5 | 1 | 2 | 1 |
| AE1 | 1,000 | 4 | | 5 | 3 | 3 | 5 | 0 |
| AE2 | 1000 | 4 | | 2 | 4 | 1 | 2 | 1 |
| AF1 | 1000 | 5 | | 5 | 4 | 2 | 4 | 1 |
| AF2 | 1000 | 5 | | 5 | 5 | 4 | 5 | 3 |
| AF3 | 1000 | 5 | | 5 | 5 | 3 | 5 | 1 |
| BA1 | 1,000 | 2 | | 3 | 2 | 2 | 1 | 1 |
| BB1 | 1,000 | 1 | | 0 | 2 | 0 | 1 | 0 |
| BD1 | 1,000 | 5 | | 5 | 5 | 4 | 5 | 1 |
| BD2 | 1,000 | 5 | | 5 | 5 | 4 | 5 | 2 |
| BD3 | 1,000 | 1 | | 2 | 2 | 1 | 1 | 0 |
| BD4 | 1,000 | 5 | | 4 | 5 | 4 | 4 | 0 |
| BD5 | 1000 | 5 | | 5 | 5 | 5 | 5 | 3 |
| BD6 | 1000 | 1 | | 0 | 2 | 1 | 1 | 1 |
| BD7 | 1000 | 5 | | 5 | 5 | 5 | 5 | 3 |
| BD8 | 1000 | 5 | | 5 | 5 | 4 | 5 | 2 |
| BD9 | 1000 | 2 | | 5 | 4 | 3 | 2 | 1 |
| BD10 | 1000 | 5 | | 5 | 5 | 5 | 5 | 4 |
| BD11 | 1000 | 4 | | 2 | 2 | 2 | 1 | 0 |
| BD12 | 1000 | 5 | | 5 | 5 | 4 | 5 | 2 |
| BD13 | 1000 | 5 | | 5 | 5 | 5 | 5 | 4 |
| BD14 | 1000 | 4 | | 5 | 4 | 4 | 3 | 1 |
| CA1 | 1,000 | 1 | | 3 | 2 | 1 | 1 | 1 |
| CA2 | 1,000 | 0 | | 0 | 0 | 1 | 0 | 0 |
| CA3 | 1,000 | 1 | | 1 | 0 | 0 | 0 | 0 |
| CA4 | 1,000 | 2 | | 1 | 1 | 1 | 0 | 1 |
| CB1 | 1,000 | 1 | | 1 | 0 | 1 | 1 | 1 |
| CB2 | 1,000 | 3 | | 3 | 0 | 1 | 1 | 0 |
| CD1 | 1,000 | 0 | | 0 | 0 | 0 | 0 | 0 |
| CD2 | 1,000 | 2 | | 5 | 4 | 3 | 3 | 1 |
| CD3 | 1,000 | 5 | | 5 | 5 | 5 | 5 | 3 |
| CD4 | 1,000 | 5 | | 3 | 5 | 5 | 5 | 1 |
| CD5 | 1000 | 3 | | 4 | 2 | 1 | 1 | 0 |
| CD6 | 1000 | 3 | | 3 | 2 | 2 | 0 | 0 |
| CD7 | 1000 | 2 | | 2 | 0 | 0 | 0 | 0 |
| CD8 | 1000 | 5 | | 5 | 5 | 5 | 5 | 3 |
| CE1 | 1000 | 4 | | 5 | 4 | 2 | 3 | 1 |
| CF1 | 1000 | 4 | | 2 | 4 | 1 | 4 | 1 |
| DA1 | 1000 | 4 | | 3 | 5 | 4 | 4 | 0 |
| DD1 | 1,000 | 4 | | 4 | 4 | 4 | 5 | 1 |
| DD2 | 1,000 | 0 | | 1 | 0 | 0 | 1 | 1 |
| DD3 | 1,000 | 3 | | 4 | 6 | 2 | 2 | 1 |

ABUTH = *Abutilon theophrasti*;
SOLNI = *Solanum nigrum*;
AMARE = *Amaranthus retroflexus*;
SETFA = *Setaria faberi*;
ALOMY = *Alopecurus myosuroides*;
ECHCG = *Echinochloa crus-galli*;
ZEAMX = *Zea mays*.

The invention claimed is:
1. A herbicidal compound of the formula (I)

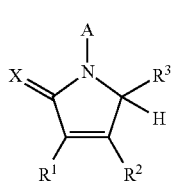

wherein
X is selected from S and O;
A is selected from

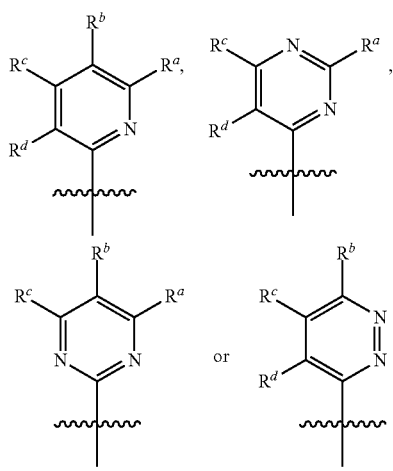

$R^a$ is selected from hydrogen and halogen;
$R^b$ is selected from hydrogen, formyl, hydroxyl, halogen, nitro, cyano, $C_1$-$C_6$ alkyl, $C_1$-$C_6$ cyanoalkyl, $C_3$-$C_6$ cycloalkyl, $C_3$-$C_6$ cyanocycloalkyl, $C_1$-$C_6$ haloalkyl, $C_1$-$C_6$ alkylthio, $C_1$-$C_6$ alkoxy, $C_1$-$C_6$ alkoxy $C_1$-$C_6$ alkyl, $C_1$-$C_6$ alkoxy $C_1$-$C_6$ alkoxy, $C_1$-$C_6$ alkthio $C_1$-$C_6$ alkyl, aryl $C_1$-$C_6$ alkylthio, $C_3$-$C_6$ cycloalkoxy, aryl $C_1$-$C_6$ alkoxy, aryl $C_1$-$C_6$ alkoxy $C_1$-$C_6$ alkoxy, $C_1$-$C_6$ cyanoalkoxy, $C_1$-$C_6$ haloalkoxy, $C_2$-$C_6$ alkenyl, $C_2$-$C_6$ alkynyl, $C_2$-$C_6$ cyanoalkenyl, $C_2$-$C_6$ cyanoalkynyl, $C_2$-$C_6$ alkenyloxy, $C_2$-$C_6$ alkynyloxy, $C_2$-$C_6$ haloalkenyl, $C_2$-$C_6$ haloalkynyl, $C_2$-$C_6$ haloalkenyloxy, $C_2$-$C_6$ haloalkynyloxy, $C_1$-$C_6$ alkoxy $C_2$-$C_6$ alkenyl, $C_1$-$C_6$ alkoxy $C_2$-$C_6$ alkynyl, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, $C_1$-$C_6$ alkylsulfonyloxy, $C_1$-$C_6$ alkylcarbonyl, $C_1$-$C_6$ haloalkylcarbonyl, a group $R^{10}O(O)C-$, $C_2$-$C_6$ alkenylcarbonyl, $C_2$-$C_6$ alkynylcarbonyl, $C_2$-$C_6$ haloalkenylcarbonyl, $C_2$-$C_6$ haloalkynylcarbonyl, $C_1$-$C_6$ alkoxycarbonyloxy, $C_1$-$C_6$ alkenyloxycarbonyloxy, $C_1$-$C_6$ alkynyloxycarbonyloxy, $C_1$-$C_6$ haloalkoxycarbonyloxy, tri $C_1$-$C_6$ alkylsilyl $C_2$-$C_6$ alkynyl, a group $R^5R^6N-$, a group $R^5C(O)N(R^6)-$, a group $R^5S(O_2)N(R^6)-$, a group $R^5R^6NC(O)-$, a group $R^5R^6NC(O)O-$, a group $R^5R^6NSO_2-$, a $C_6$-$C_{10}$ aryl group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy and $C_1$-$C_6$ alkyl $S(O_2)-$ or any two groups on adjacent carbon atoms together with the carbon atoms to which they are attached form a 3-6 membered saturated or partially unsaturated ring optionally comprising from 1 to 3 heteroatoms independently selected from S, O and N; a $C_5$-$C_{10}$ heteroaryl group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy; a $C_6$-$C_{10}$ aryloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy; a $C_6$-$C_{10}$ benzyl group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy; a $C_6$-$C_{10}$ benzyloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy; a $C_3$-$C_6$ heterocyclyl group optionally substituted by from 1 to 3 groups independently selected from $C_1$-$C_4$ alkyl; a $C_5$-$C_{10}$ heteroaryl $C_1$-$C_6$ alkoxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy; a heterocyclyl $C_1$-$C_6$ alkoxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy; and a $C_3$-$C_6$ cycloalkyl ring optionally comprising from 1 to 3 heteroatoms independently selected from S, O and N and optionally substituted with from 1 to 3 groups independently selected from halogen or $C_1$-$C_6$ alkyl; or $R^b$ and $R^c$ together with the carbon atoms to which they are attached form a 3-6 membered saturated or partially unsaturated ring optionally comprising from 1 to 3 heteroatoms independently selected from S, O and N and optionally substituted with from 1 to 3 groups independently selected from halogen or $C_1$-$C_6$ alkyl;
$R^c$ is selected from hydrogen, formyl, halogen, cyano, $C_1$-$C_6$ alkyl, $C_1$-$C_6$ cyanoalkyl, $C_3$-$C_6$ cycloalkyl, $C_3$-$C_6$ cyanocycloalkyl, $C_1$-$C_6$ haloalkyl, $C_1$-$C_6$ alkoxy, $C_1$-$C_6$ cyanoalkoxy, $C_1$-$C_6$ haloalkoxy, $C_2$-$C_6$ alkenyl, $C_2$-$C_6$ alkynyl, $C_2$-$C_6$ cyanoalkenyl, $C_2$-$C_6$ cyanoalkynyl, $C_2$-$C_6$ alkenyloxy, $C_1$-$C_6$ alkoxy $C_1$-$C_6$ alkyl, $C_2$-$C_6$ alkynyloxy, $C_2$-$C_6$ haloalkenyl, $C_2$-$C_6$ haloalkynyl, $C_2$-$C_6$ haloalkenyloxy, $C_1$-$C_6$ alkthio $C_1$-$C_6$ alkyl, $C_2$-$C_6$ haloalkynyloxy, $C_1$-$C_6$ alkylthio, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, $C_1$-$C_6$ alkylcarbonyl, $C_1$-$C_6$ haloalkylcarbonyl, a group $R^5R^6N-$ and, when $R^b$ is other than hydrogen or methyl, nitro; or $R^b$ and $R^c$ together with the carbon atoms to which they are attached form a 3-6 membered saturated or partially unsaturated ring optionally comprising from 1 to 3 heteroatoms independently selected from S, O and N and optionally substituted with from 1 to 3 groups independently selected from halogen or $C_1$-$C_6$ alkyl;
$R^d$ is selected from hydrogen, cyano and halogen;
$R^1$ is $C_1$-$C_6$ alkyl or $C_1$-$C_3$ alkoxy and $R^2$ is chlorine or bromine, $C_2$-$C_6$ alkenyloxy, $C_1$-$C_6$ haloalkyloxy or $C_1$-$C_3$ alkoxy with the proviso that $R^1$ and $R^2$ are not both $C_1$-$C_3$ alkoxy;
$R^3$ is selected from halogen, hydroxyl, or any one of the following groups

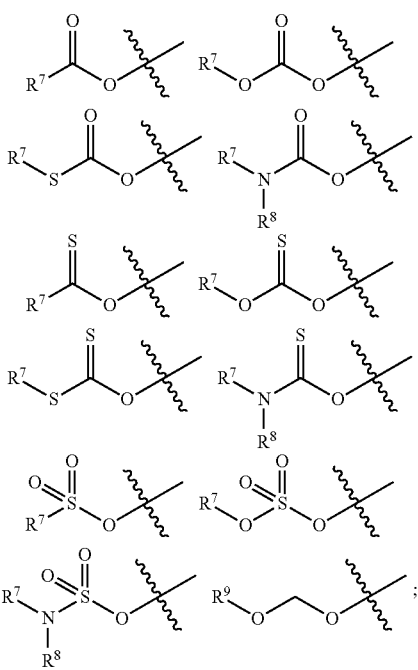

$R^5$ and $R^6$ are independently selected from hydrogen, $C_1$-$C_6$ alkyl, $C_1$-$C_6$ haloalkyl, $C_2$-$C_6$ alkenyl, $C_2$-$C_6$ alkynyl, aryl $C_1$-$C_6$ alkyl, or $R^5$ and $R^6$ together with the carbon atoms to which they are attached form a 3-6 membered saturated or partially unsaturated ring optionally comprising from 1 to 3 heteroatoms independently selected from S, O and N and optionally substituted with from 1 to 3 groups independently selected from halogen or $C_1$-$C_6$ alkyl;

$R^7$ and $R^8$ are independently selected from hydrogen, $C_1$-$C_6$ alkyl, $C_1$-$C_6$ haloalkyl, $C_2$-$C_6$ alkenyl, $C_2$-$C_6$ alkynyl; 5 to 10 membered heteroaryl which can be mono- or bicyclic comprising from 1 to 4 heteroatoms independently selected from N, O and S, optionally substituted with 1 to 3 groups independently selected from halogen, $C_1$-$C_3$ alkyl, $C_1$-$C_3$ haloalkyl and $C_1$-$C_3$ alkoxy; $C_6$-$C_{10}$ aryl optionally substituted with 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy; or $R^7$ and $R^8$ together with the carbon atoms to which they are attached form a 3-6 membered saturated or partially unsaturated ring optionally comprising from 1 to 3 heteroatoms independently selected from S, O and N and optionally substituted with from 1 to 3 groups independently selected from halogen or $C_1$-$C_6$ alkyl;

$R^9$ is selected from $C_1$-$C_6$ alkyl or benzyl optionally substituted with 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy;

$R^{10}$ is selected from hydrogen, $C_1$-$C_6$ alkyl, $C_1$-$C_6$ haloalkyl, $C_2$-$C_6$ alkenyl and $C_2$-$C_6$ alkynyl;

with the provisos that (i) if $R^b$ is methylthio, methoxy, methoxycarbonyl, fluorine or trifluoromethyl and $R^2$ is chlorine or bromine, $R^c$ cannot be hydrogen and (ii) if $R^b$ is tri $C_1$-$C_6$ alkylsilyl $C_2$-$C_6$ alkynyl, $R^2$ cannot be chlorine or bromine;

or an N-oxide or salt form thereof.

2. The compound of claim 1, wherein X is O.

3. The compound of claim 1, wherein A is

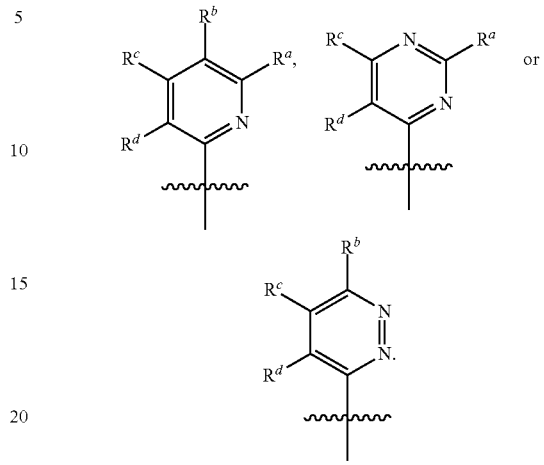

4. The compound of claim 1, wherein $R^a$ is selected from hydrogen and fluorine.

5. The compound of claim 1, wherein $R^b$ is selected from hydrogen, halogen, cyano, $C_1$-$C_6$ alkyl, $C_1$-$C_6$ haloalkyl, $C_1$-$C_6$ alkylthio, $C_1$-$C_6$ cyanoalkenyl, $C_1$-$C_6$ alkoxy, $C_1$-$C_6$ haloalkoxy, $C_1$-$C_6$ alkoxy $C_1$-$C_6$ alkoxy, $C_2$-$C_6$ alkenyl, $C_2$-$C_6$ alkynyl, $C_1$-$C_6$ alkoxy $C_2$-$C_6$ alkenyl, $C_1$-$C_6$ alkylsulfinyl, $C_1$-$C_6$ alkylsulfonyl, $C_1$-$C_6$ alkylcarbonyl, a group $R^{10}O(O)C-$, a group $R^5R^6NC(O)-$, a group $R^5C(O)N(R^6)-$, a group $R^5R^6NSO_2-$, tri $C_1$-$C_6$ alkylsilyl $C_2$-$C_6$ alkynyl, a $C_6$-$C_{10}$ aryl group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy, a $C_6$-$C_{10}$ aryloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy; a $C_5$-$C_{10}$ heteroaryl group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy; a $C_3$-$C_6$ heterocyclyl group optionally substituted by from 1 to 3 groups independently selected from $C_1$-$C_4$ alkyl; and a heterocyclyl $C_1$-$C_6$ alkoxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy.

6. The compound of claim 1, wherein $R^c$ is selected from hydrogen, halogen, cyano, $C_1$-$C_6$ alkyl, $C_1$-$C_6$ cycloalkyl, $C_1$-$C_6$ alkylcarbonyl, $C_1$-$C_6$ haloalkyl, $C_1$-$C_6$ cyanoalkyl, $C_1$-$C_6$ alkoxy, $C_1$-$C_6$ haloalkoxy, $C_2$-$C_6$ alkenyl, $C_1$-$C_6$ alkylsulfinyl, a group $R^5R^6N-$.

7. The compound of claim 1, wherein $R^d$ is selected from hydrogen, cyano, fluoro or chloro.

8. The compound of claim 1, wherein $R^1$ is methyl, ethyl, methoxy or ethoxy, with the proviso that when $R^1$ is methoxy or ethoxy, $R^2$ is not methoxy, ethoxy, allyloxy or 2,2,2-trifluoroethyloxy.

9. The compound of claim 1, wherein $R^2$ is bromo, chloro, methoxy, ethoxy, allyloxy or 2,2,2-trifluoroethyloxy with the proviso that when $R^1$ is methoxy or ethoxy, $R^2$ is not methoxy, ethoxy, allyloxy or 2,2,2-trifluoroethyloxy.

10. The compound of claim 1, wherein $R^3$ is halogen, hydroxyl or $C_1$-$C_6$ alkylcarbonyloxy.

11. A herbicidal composition comprising a compound of formula I as defined in claim 1 together with at least one agriculturally acceptable adjuvant or diluent.

12. A composition according to claim 11 which comprises a further herbicide in addition to the compound of formula I.

13. A composition according to claim 11 which further comprises a safener.

14. A method of controlling weeds in crops of useful plants, comprising applying to said weeds or to the locus of said weeds, or to said useful plants or to the locus of said useful plants, a compound of formula I as defined in claim 1.

* * * * *